US011168132B2

(12) United States Patent
Sellman et al.

(10) Patent No.: US 11,168,132 B2
(45) Date of Patent: Nov. 9, 2021

(54) TREATMENT OF POLYBACTERIAL INFECTIONS

(71) Applicant: MedImmune, LLC, Gaithersburg, MD (US)

(72) Inventors: Bret Sellman, Gaithersburg, MD (US); Jamese Johnson Hilliard, Gaithersburg, MD (US); Omari Jones, Gaithersburg, MD (US); Charles Ken Stover, Gaithersburg, MD (US)

(73) Assignee: MedImmune, LLC, Gaithersburg, MD (US)

( * ) Notice: Subject to any disclaimer, the term of this patent is extended or adjusted under 35 U.S.C. 154(b) by 0 days.

(21) Appl. No.: 15/319,958

(22) PCT Filed: Jun. 19, 2015

(86) PCT No.: PCT/US2015/036576
§ 371 (c)(1),
(2) Date: Dec. 19, 2016

(87) PCT Pub. No.: WO2015/196011
PCT Pub. Date: Dec. 23, 2015

(65) Prior Publication Data
US 2017/0129943 A1 May 11, 2017

Related U.S. Application Data

(60) Provisional application No. 62/140,849, filed on Mar. 31, 2015, provisional application No. 62/014,506, filed on Jun. 19, 2014.

(51) Int. Cl.
| | | |
|---|---|---|
| *C07K 16/12* | (2006.01) | |
| *A61K 31/496* | (2006.01) | |
| *A61K 39/40* | (2006.01) | |
| *A61K 39/00* | (2006.01) | |

(52) U.S. Cl.
CPC ........ *C07K 16/1271* (2013.01); *A61K 31/496* (2013.01); *A61K 39/40* (2013.01); *C07K 16/1214* (2013.01); *A61K 2039/505* (2013.01); *A61K 2039/507* (2013.01); *C07K 2317/31* (2013.01); *C07K 2317/51* (2013.01); *C07K 2317/515* (2013.01); *C07K 2317/56* (2013.01); *C07K 2317/565* (2013.01); *C07K 2317/622* (2013.01); *C07K 2317/76* (2013.01)

(58) Field of Classification Search
None
See application file for complete search history.

(56) References Cited

U.S. PATENT DOCUMENTS

| | | |
|---|---|---|
| 9,527,905 B2 | 12/2016 | Sellman et al. |
| 9,845,348 B2 | 12/2017 | Sellman et al. |
| 9,879,070 B2 | 1/2018 | Sellman et al. |
| 10,457,724 B2 | 10/2019 | Sellman et al. |
| 2011/0165172 A1 | 7/2011 | Yarranton |
| 2014/0072577 A1 | 3/2014 | Sellman et al. |
| 2019/0002540 A1 | 1/2019 | Sellman et al. |
| 2019/0016787 A1 | 1/2019 | Sellman et al. |
| 2019/0077851 A1 | 3/2019 | Jafri et al. |

FOREIGN PATENT DOCUMENTS

| | | |
|---|---|---|
| WO | WO 2007/145689 A1 | 12/2007 |
| WO | WO 2011/087799 A1 | 7/2011 |
| WO | WO 2012/109285 A1 | 8/2012 |
| WO | WO 2013/070615 A1 | 5/2013 |
| WO | WO 2014/074470 A1 | 5/2014 |
| WO | WO 2014/074528 A2 | 5/2014 |
| WO | WO 2014/074540 A2 | 5/2014 |
| WO | WO 2017/075188 A2 | 5/2017 |

OTHER PUBLICATIONS

Skolnick et al. (Trends in Biotechnology 18: 34-39, 2000) (Year: 2000).*
Greenspan et al. (Nature Biotechnology 7: 936-937, 1999) (Year: 1999).*
Giusti et al. (Proc.Natl. Acad. Sci. USA. May 1987 84 (9): 2926-2930) (Year: 1987).*
Winkler et al (J. Imm., 265:4505-4514, 2000) (Year: 2000).*
Chien et al. (Proc. Natl. Acad. Sci. USA. Jul. 1989 86 (14): 5532-5536) (Year: 1989).*
Caldas et al. (Mol. Immunol. May 2003 39 (15): 941-952) (Year: 2003).*
Casadevall et al. (PNAS, vol. 109 No. 31, pp. 12272-12273).*
Hilliard et al. "*Staphylococcus aureus* Alpha-Toxin Potentiates Pseudomonas AerugINOSa Infection in a Murine Pneumonia Model," Ant J Respir Crit Care Med. May 18, 2015 (May 18, 2015), vol. 191, Abstract: A3691.
International Search Report for PCT/US2015/036576 dated Sep. 16, 2015.
International Preliminary Report on Patentability for PCT/US2015/036576 dated Dec. 20, 2016.
Witten Opinion for International Application No. PCT/US2015/036576 dated Sep. 16, 2015.

(Continued)

*Primary Examiner* — Robert A Zeman
(74) *Attorney, Agent, or Firm* — Sterne, Kessler, Goldstein & Fox P.L.L.C.

(57) ABSTRACT

Provided herein are methods of preventing and treating polybacterial infections comprising administering an effective amount of an antibody or antigen-binding fragment thereof that specifically binds to an epitope produced by at least one of the bacterium in the polybacterial infection. For example, an antibody that specifically binds to *Staphylococcus aureus* alpha toxin can be administered to a patient with a polybacterial infection comprising *Staphylococcus aureus* and *Pseudomonas aeruginosa* to inhibit the growth of *Pseudomonas aeruginosa*.

10 Claims, 14 Drawing Sheets
Specification includes a Sequence Listing.

(56) References Cited

OTHER PUBLICATIONS

L. M. Mashburn et al. "*Staphylococcus aureus* Serves as an Iron Source for Pseudomonas aeruginosa during In Vivo Coculmre," Journal of Bacteriology, Jan. 15, 2005, vol. 187, No. 2, pp. 554-566.
Hendricks, K. J. et al. "Synergy between *Staphylococcus aureus* and Pseudomonas aeruginosa in a rat model of complex orthopaedic wounds," Journal of Bone and Joint Surgery, May 31, 2001, vol. 83-A, No. 6, pp. 855-861.
Supplementary Partial European Search Report for EP Application No. 15809174 completed Oct. 27, 2017.
Mashburn; L. M. et al, "*Staphylococcus aureus* Serves as an Iron Source for Pseudomonas aeruginosa during In Vivo Coculture", Journal of Bacteriology 187(2):554-66, American Society of Microbiology, United States (2005).
Peleg et al., "Hospital-Acquired Infections Due to Gram-Negative Bacteria," N Engl J Med. 362: 1804-1813, Massachusetts Medical Society, United States (2010).

* cited by examiner

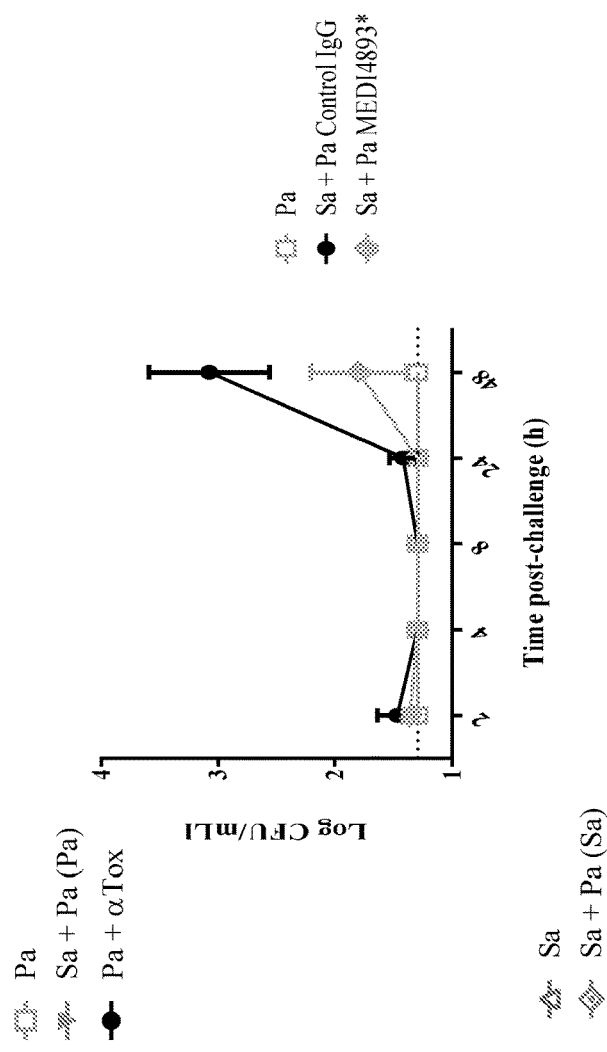
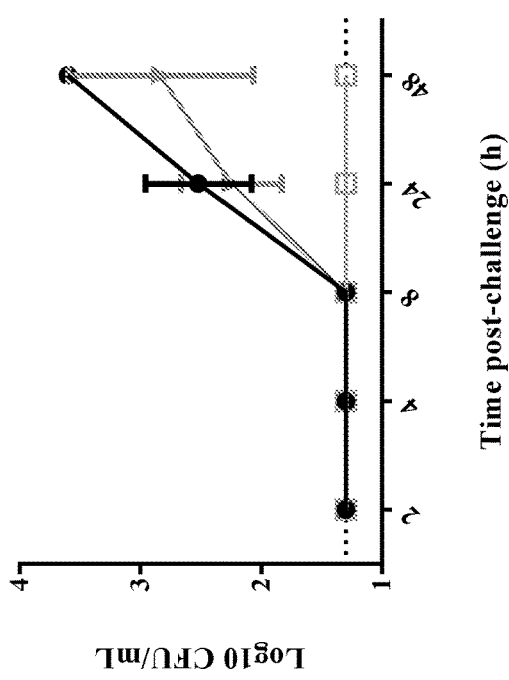
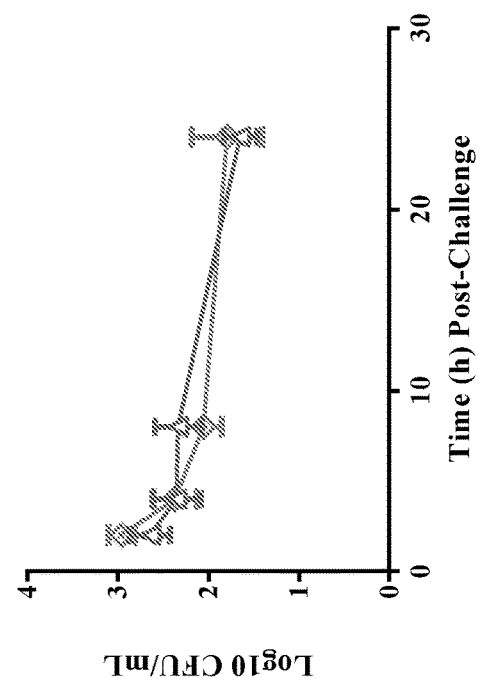
Figure 11A
Figure 11B
Figure 11C

TREATMENT OF POLYBACTERIAL INFECTIONS

CROSS-REFERENCE TO RELATED APPLICATIONS

This application is a U.S. National Stage application of International Application No. PCT/US2015/036576, filed on Jun. 19, 2015, said International Application No. PCT/US2015/036576 claims benefit under 35 U.S.C. §119(e) of the U.S. Provisional Application No. 62/014,506, filed Jun. 19, 2014 and U.S. Provisional Application No. 62/140,849, filed Mar. 31, 2015. Each of the above listed applications is incorporated by reference herein in its entirety for all purposes.

REFERENCE TO THE SEQUENCE LISTING

This application incorporates by reference a Sequence Listing submitted with this application as text file entitled ATOX_510WO1_SequenceListing, created on Jun. 19, 2015, and having a size of 90.4 kilobytes.

FIELD

The technology relates to the use of anti-bacterial antibodies or antigen-binding fragments thereof for the treatment and prevention of infections including polybacterial infections.

BACKGROUND

Opportunistic infections are infections that are more frequent and/or more severe as a result of a particularly suitable environment such as a weakened immune system. They frequently present in hospitalized and/or immunosuppressed patients. Often times, opportunistic infections are polymicrobial, i.e., involving multiple infectious agents. Two important opportunistic bacteria are *Staphylococcus aureus* and *Pseudomonas aeruginosa*.

*Staphylococcus aureus* (*S. aureus*) is a Gram-positive, facultatively aerobic, clump-forming cocci bacterium that commonly colonizes the nose and skin of healthy humans. Approximately 20-30% of the population is colonized with *S. aureus* at any given time. Mucosal and epidermal barriers (skin) normally protect against *S. aureus* infections, but opportunistic *S. aureus* infections can become serious, causing a variety of diseases or conditions, non-limiting examples of which include bacteremia, cellulitis, eyelid infections, food poisoning, joint infections, skin infections, scalded skin syndrome, toxic shock syndrome, pneumonia, osteomyelitis, endocarditis, meningitis, and abscess formation.

*Pseudomonas aeruginosa* (*P. aeruginosa*) is a Gram-negative bacterium that causes both acute and chronic infections. *P. aeruginosa* is a common cause of hospital-acquired infections in the Western world. It is a frequent causative agent of bacteremia in burn victims and immune compromised individuals. It is also the most common cause of nosocomial Gram-negative pneumonia, especially in mechanically ventilated patients, and is the most prevalent pathogen in the lungs of individuals with cystic fibrosis.

Infections with bacteria such as *S. aureus* and *P. aeruginosa* are associated with increased morbidity and mortality, and *S. aureus* and *P. aeruginosa* are commonly isolated from the same patient. In view of this, as well as the fact that multidrug resistance is increasing, there is a need for novel strategies for preventing and treating bacterial infections including polybacterial infections.

BRIEF SUMMARY

Methods of preventing and treating polybacterial infections comprising administering an effective amount of an antibody or antigen-binding fragment thereof that specifically binds to an epitope produced by at least one of the bacterium in the polybacterial infection are provided herein. For example, an antibody that specifically binds to *Staphylococcus aureus* alpha toxin can be administered to a patient with a polybacterial infection comprising *Staphylococcus aureus* and *Pseudomonas aeruginosa* to inhibit the growth of *Pseudomonas aeruginosa*.

In certain aspects, a method of treating or preventing a polybacterial infection in a patient comprises administering an antibody or antigen-binding fragment thereof that specifically binds to a *Staphylococcus aureus* (*S. aureus*) antigen, wherein the polybacterial infection comprises *S. aureus* and at least one other bacterium. In certain aspects, the *S. aureus* potentiates the growth of the at least one other bacterium in the patient. In certain aspects, the administration inhibits the growth of the at least one other bacterium. In certain aspects, the at least one other bacterium is *Pseudomonas*. In certain aspects, the *Pseudomonas* is *Pseudomonas aeruginosa* (*P. aeruginosa*).

In certain aspects, a method of treating or preventing a polybacterial infection in a patient comprises administering an antibody or antigen-binding fragment thereof that specifically binds to a *P. aeruginosa* antigen, wherein the polybacterial infections comprises *P. aeruginosa* and at least one other bacterium. In certain aspects, the *P. aeruginosa* potentiates the growth of the at least one other bacterium. In certain aspects, the administration inhibits the growth of the at least one other bacterium. In certain aspects, the at least one other bacterium is *Staphylococcus*. In certain aspects, the *Staphylococcus* is *S. aureus*.

In certain aspects, a method of inhibiting the growth of *P. aeruginosa* in a patient comprises administering to the patient an antibody or antigen-binding fragment thereof that specifically binds to a *S. aureus* antigen.

In certain aspects, a method of reducing *S. aureus* colony forming units (CFU) in a patient comprises administering to the patient an antibody or antigen-binding fragment thereof that specifically binds to a *Pseudomonas aeruginosa* antigen.

In certain aspects, an antibody or antigen-binding fragment thereof specifically binds to a *S. aureus* antigen, and the *S. aureus* antigen is alpha toxin. In certain aspects, the antibody or antigen-binding fragment thereof that binds to *S. aureus* alpha toxin binds to the same alpha toxin epitope as an antibody comprising the VH and VL sequences of SEQ ID NOs:20 and 19; SEQ ID NOs; 22 and 21; SEQ ID NOs:24 and 23; SEQ ID NOs:26 and 25; SEQ ID NOs:28 and 27; SEQ ID NOs:29 and 30; SEQ ID NOs:31 and 32; SEQ ID NOs:33 and 34; SEQ ID NOs:35 and 36; SEQ ID NOs:37 and 38; SEQ ID NOs:39 and 40; SEQ ID NOs:41 and 42; SEQ ID NOs:43 and 44; SEQ ID NOs:45 and 46; SEQ ID NOs:47 and 48; SEQ ID NOs:49 and 46; SEQ ID NOs:50 and 46; SEQ ID NOs:50 and 51; or SEQ ID NOs:67 and 51. In certain aspects, the antibody or antigen-binding fragment thereof that binds to *S. aureus* alpha toxin is an antibody or antigen-binding fragment thereof comprising (a) a VH CDR1 comprising the amino acid sequence of SEQ ID NO:7, 10, 13, or 57; (b) a VH CDR2 comprising the amino acid sequence of SEQ ID NO:8, 11, 14, 17, 58, or 63; (c) a VH CDR3 comprising the amino acid sequence of SEQ ID NO:9, 12, 15, 18, 16, 53, 54, 55, 66, 59, 60, or 64; (d) a VL CDR1 comprising the amino acid sequence of SEQ ID NO:1 or 4; (e) a VL CDR2 comprising the amino acid sequence of SEQ ID NO:2, 5, 61, or 65; and (f) a VL CDR3 comprising the amino acid sequence of SEQ ID NO:3, 6, 52, 56, or 62. In certain aspects, the antibody or antigen-binding fragment thereof that binds to S. aureus alpha toxin comprises the VH CDR1, VH CDR2, VH CDR3, VL CDR1, VL CDR2, and VL CDR3 of SEQ ID NOs:7, 8, 9, 1, 2, and 3; SEQ ID NOs:10, 11, 12, 1, 2, and 3; SEQ ID NOs:13, 14, 15, 4, 5, and 6; SEQ ID NOs:7, 17, 18, 1, 2, and 3; SEQ ID NOs:7, 8, 16, 1, 2, and 52; SEQ ID NOs:7, 8, 53, 1, 2, and 52; SEQ ID NOs; 7, 8, 54, 1, 2, and 52; SEQ ID NOs:7, 8, 55, 1, 2, and 56; SEQ ID NOs:7, 8, 55, 1, 2, and 52; SEQ ID NOs:7, 8, 66, 1, 2, and 52; SEQ ID NOs:7, 8, 53, 1, 2, and 56; SEQ ID NOs:57, 58, 59, 1, 2, and 56; SEQ ID NOs:7, 8, 60, 1, 61, and 62; SEQ ID NOs:57, 63, 59, 1, 2, and 56; SEQ ID NOs:57, 63, 64, 1, 2, and 56; SEQ ID NOs:57, 63, 64, 1, 65, and 62; or SEQ ID NOs:57, 58, 59, 1, 65, and 67. In certain aspects, the VH and the VL of the antibody or antigen-binding fragment thereof that binds to S. aureus alpha comprise to the amino acid sequences of SEQ ID NOs:20 and 19; SEQ ID NOs; 22 and 21; SEQ ID NOs:24 and 23; SEQ ID NOs:26 and 25; SEQ ID NOs:28 and 27; SEQ ID NOs:29 and 30; SEQ ID NOs:31 and 32; SEQ ID NOs:33 and 34; SEQ ID NOs:35 and 36; SEQ ID NOs:37 and 38; SEQ ID NOs:39 and 40; SEQ ID NOs:41 and 42; SEQ ID NOs:43 and 44; SEQ ID NOs:45 and 46; SEQ ID NOs:47 and 48; SEQ ID NOs:49 and 46; SEQ ID NOs:50 and 46; SEQ ID NOs:50 and 51; or SEQ ID NOs:67 and 51.

In certain aspects, the antibody or antigen-binding fragment thereof that binds to S. aureus alpha toxin binds to the same alpha toxin epitope as an antibody comprising the VH and VL sequences of SEQ ID NOs:45 and 46. In certain aspects, the antibody or antigen-binding fragment thereof that binds to S. aureus alpha toxin comprises the VH CDR1, VH CDR2, VH CDR3, VL CDR1, VL CDR2, and VL CDR3 sequences of SEQ ID NOs:57, 58, 59, 1, 2, and 56, respectively. In certain aspects, the VH and VL of the antibody or antigen-binding fragment thereof that binds to S. aureus alpha toxin comprise the amino acid sequences of SEQ ID NOs:45 and 46. In certain aspects, the antibody or antigen-binding fragment thereof that specifically binds to S. aureus alpha toxin comprises a heavy chain comprising the amino acid sequence of SEQ ID NO:68 and a light chain comprising the amino acid sequence of SEQ ID NO:69.

In certain aspects, an antibody or antigen-binding fragment thereof specifically binds to a P. aeruginosa antigen, and the P. aeruginosa antigen is Psl, PcrV, or both Psl and PcrV. In certain aspects, the antibody or antigen-binding fragment thereof binds to P. aeruginosa Psl and PcrV.

In certain aspects, the antibody or antigen-binding fragment thereof that binds to a P. aeruginosa antigen binds to the same P. aeruginosa Psl epitope as an antibody comprising the VH and VL sequences of SEQ ID NOs:79 and 72. In certain aspects, the antibody or antigen-binding fragment thereof that binds to a P. aeruginosa antigen binds to the same P. aeruginosa PcrV epitope as an antibody comprising the VH and VL sequences of SEQ ID NOs:81 and 82. In certain aspects, the antibody or antigen-binding fragment thereof that binds to a P. aeruginosa antigen binds to the same P. aeruginosa Psl epitope as an antibody comprising the VH and VL sequences of SEQ ID NOs:79 and 72 and binds to the same P. aeruginosa PcrV epitope as an antibody comprising the VH and VL sequences of SEQ ID NOs:81 and 82.

In certain aspects, the antibody or antigen-binding fragment thereof that binds to a P. aeruginosa antigen binds to the same P. aeruginosa Psl epitope as an antibody comprising the VH and VL sequences of SEQ ID NOs:96 and 97. In certain aspects, the antibody or antigen-binding fragment thereof that binds to a P. aeruginosa antigen binds to the same P. aeruginosa PcrV epitope as an antibody comprising the VH and VL sequences of SEQ ID NOs:98 and 99. In certain aspects, the antibody or antigen-binding fragment thereof that binds to a P. aeruginosa antigen binds to the same P. aeruginosa Psl epitope as an antibody comprising the VH and VL sequences of SEQ ID NOs:96 and 97 and binds to the same P. aeruginosa PcrV epitope as an antibody comprising the VH and VL sequences of SEQ ID NOs:98 and 99.

In certain aspects, the antibody or antigen-binding fragment thereof that binds to a P. aeruginosa antigen comprises the VH CDR1, VH CDR2, VH CDR3, VL CDR1, VL CDR2, and VL CDR3 sequences of SEQ ID NOs:73, 74, 80, 76, 77, and 78 or SEQ ID NOs: 73, 74, 94, 76, 77, and 95. In certain aspects, the antibody or antigen-binding fragment thereof that binds to a P. aeruginosa antigen comprises the VH CDR1, VH CDR2, VH CDR3, VL CDR1, VL CDR2, and VL CDR3 sequences of SEQ ID NOs:83, 84, 85, 86, 87, and 88. In certain aspects, the antibody or antigen-binding fragment thereof that binds to a P. aeruginosa antigen (e.g., Psl and PcrV) comprises the VH CDR1, VH CDR2, VH CDR3, VL CDR1, VL CDR2, and VL CDR3 sequences of SEQ ID NOs:73, 74, 80, 76, 77, and 78 or SEQ ID NOs: 73, 74, 94, 76, 77, and 95 and comprises the VH CDR1, VH CDR2, VH CDR3, VL CDR1, VL CDR2, and VL CDR3 sequences of SEQ ID NOs:83, 84, 85, 86, 87, and 88. In certain aspects, the VH CDR1, VH CDR2, VH CDR3, VL CDR1, VL CDR2, and VL CDR3 sequences of SEQ ID NOs:73, 74, 80, 76, 77, and 78 or SEQ ID NOs: 73, 74, 94, 76, 77, and 95 are in an ScFv. In certain aspects, the VH CDR1, VH CDR2, VH CDR3, VL CDR1, VL CDR2, and VL CDR3 sequences of SEQ ID NOs:83, 84, 85, 86, 87, and 88 are in an ScFv. In certain aspects, the VH CDR1, VH CDR2, VH CDR3, VL CDR1, VL CDR2, and VL CDR3 sequences of SEQ ID NOs:83, 84, 85, 86, 87, and 88 are in an IgG. In certain aspects, the VH CDR1, VH CDR2, VH CDR3, VL CDR1, VL CDR2, and VL CDR3 sequences of SEQ ID NOs:73, 74, 80, 76, 77, and 78 or SEQ ID NOs: 73, 74, 94, 76, 77, and 95 are in an IgG.

In certain aspects, the antibody or antigen-binding fragment thereof that binds to a P. aeruginosa antigen comprises the VH sequence of SEQ ID NO:79 and the VL sequence of SEQ ID NO:72. In certain aspects, the antibody or antigen-binding fragment thereof that binds to a P. aeruginosa antigen comprises the VH sequence of SEQ ID NO:81 and the VL sequence of SEQ ID NO:82. In certain aspects, the antibody or antigen-binding fragment thereof that binds to a P. aeruginosa antigen (e.g., Psl and PcrV) comprises the VH sequence of SEQ ID NO:79, the VL sequence of SEQ ID NO:72, the VH sequence of SEQ ID NO:81, and the VL sequence of SEQ ID NO:82. In certain aspects, the VH sequence of SEQ ID NO:79 and the VL sequence of SEQ ID NO:72 are in an ScFv. In certain aspects, the VH sequence of SEQ ID NO:81 and the VL sequence of SEQ ID NO:82 are in an ScFv. In certain aspects, the VH sequence of SEQ ID NO:81 and the VL sequence of SEQ ID NO:82 are in an IgG. In certain aspects, the VH sequence of SEQ ID NO:79 and the VL sequence of SEQ ID NO:72 are in an IgG. In certain aspects, the IgG contains the YTE mutations.

In certain aspects, the antibody or antigen-binding fragment thereof that binds to a P. aeruginosa antigen comprises the amino acid sequence of SEQ ID NO:89. In certain aspects, the antibody or antigen-binding fragment thereof that binds to a *P. aeruginosa* antigen the amino acid sequence of SEQ ID NO:90. In certain aspects, the antibody or antigen-binding fragment thereof that binds to a *P. aeruginosa* antigen comprises the amino acid sequence of SEQ ID NO:91.

In certain aspects, the antibody or antigen-binding fragment thereof that binds to a *P. aeruginosa* antigen comprises a heavy chain comprising the amino acid sequence of SEQ ID NO:93 and a light chain comprising the amino acid sequence of SEQ ID NO:92.

In certain aspects, the antibody or antigen-binding fragment thereof that binds to a *P. aeruginosa* antigen comprises the VH sequence of SEQ ID NO:96 and the VL sequence of SEQ ID NO:97. In certain aspects, the antibody or antigen-binding fragment thereof that binds to a *P. aeruginosa* antigen comprises the VH sequence of SEQ ID NO:98 and the VL sequence of SEQ ID NO:99. In certain aspects, the antibody or antigen-binding fragment thereof that binds to a *P. aeruginosa* antigen (e.g., Psl and PcrV) comprises the VH sequence of SEQ ID NO:96, the VL sequence of SEQ ID NO:97, the VH sequence of SEQ ID NO:98, and the VL sequence of SEQ ID NO:99. In certain aspects, the VH sequence of SEQ ID NO:96 and the VL sequence of SEQ ID NO:97 are in an ScFv. In certain aspects, the VH sequence of SEQ ID NO:98 and the VL sequence of SEQ ID NO:99 are in an ScFv. In certain aspects, the VH sequence of SEQ ID NO:98 and the VL sequence of SEQ ID NO:99 are in an IgG. In certain aspects, the VH sequence of SEQ ID NO:96 and the VL sequence of SEQ ID NO:97 are in an IgG. In certain aspects, the IgG contains the YTE mutations.

In certain aspects, the antibody or antigen-binding fragment thereof that specifically binds to *P. aeruginosa* Psl and PcrV comprises a heavy chain comprising the amino acid sequence of SEQ ID NO:101 and a light chain comprising the amino acid sequence of SEQ ID NO:100.

In certain aspects, the antibody or antigen-binding fragment thereof (e.g., an antibody or antigen-binding fragment thereof that binds to an *S. aureus* antigen or an antibody or antigen-binding fragment thereof that binds to a *P. aeruginosa* antigen) is administered for two or more prevention or treatment cycles.

In certain aspects, the methods provided herein comprise administering an antibody or antigen-binding fragment thereof (e.g., an antibody or antigen-binding fragment thereof that binds to an *S. aureus* antigen or an antibody or antigen-binding fragment thereof that binds to a *P. aeruginosa* antigen) and administering a second anti-bacterial agent.

In certain aspects, the polybacterial infection is an ocular infection, a lung infection, a burn infection, a wound infection, a surgical wound infection, a skin infection, a soft tissue infection, a blood infection, a bone infection, or a combination of two or more of said infections.

In certain aspects, the patient has acute pneumonia, burn injury, corneal infection, cystic fibrosis, ventilator-associated pneumonia, a skin infection, a wound infection, or a combination thereof.

In certain aspects, the patient is hospitalized.

In certain aspects, the methods provided herein comprise administering an antibody or antigen-binding fragment thereof (e.g., an antibody or antigen-binding fragment thereof that binds to an *S. aureus* antigen or an antibody or antigen-binding fragment thereof that binds to a *P. aeruginosa* antigen) and result in the outcomes shown in FIGS. 1-10 and described in Examples 1-4.

BRIEF DESCRIPTION OF THE FIGURES

FIG. 11(A) shows that LC10 reduces pulmonary CFU and dissemination. A) Groups of mice were injected with LC10 (□), or the iso-type control IgG (o) and challenged intranasally 24 h later with 1e5 CFU of *P. aeruginosa* and 5e7 CFU *S. aureus*, or *P. aeruginosa*+AT. Lungs and spleens were removed at the indicated times for CFU determination. FIG. 11(B) *S. aureus* bacterial burden in the spleens of mice in the mono (Sa) or co-infected (Sa+Pa (Sa)) mice at the indicated time points following intranasal challenge as described above. FIG. 11(C) Numbers of *P. aeruginosa* recovered from distal organs at 24 and 48 h in mono infection, co-infection and co-infection combined with prophylaxis using LC10.

DETAILED DESCRIPTION

Figure 1:
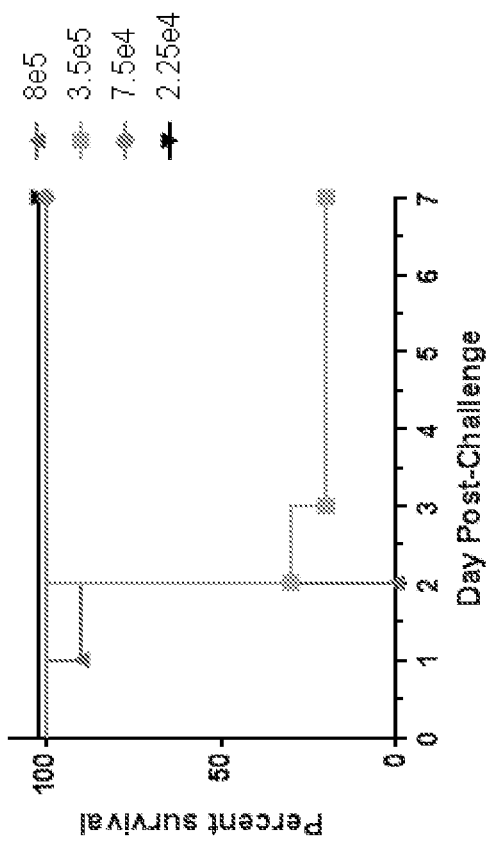
FIG. 1 shows the survival of mice inoculated with *Pseudomonas aeruginosa* strain 6077 (A) or *Staphylococcus aureus* strain SF8300 (B).
Figure 1:
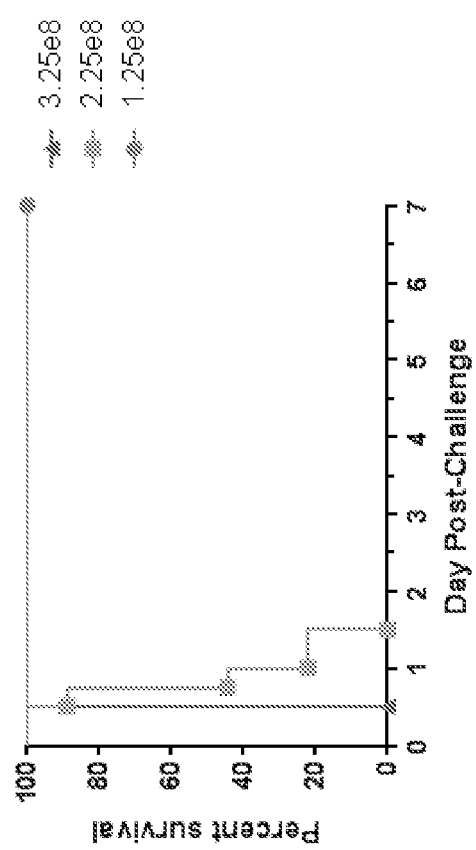

It is to be noted that the term "a" or "an" entity refers to one or more of that entity; for example, "an antibody or antigen-binding fragment thereof" is understood to represent one or more antibodies or antigen-binding fragments thereof. As such, the terms "a" (or "an"), "one or more," and "at least one" can be used interchangeably herein.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants.

The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of ways including, but not limited to, by hybridoma, phage selection, recombinant expression, and transgenic animals.

The term "humanized antibody" refers to an antibody derived from a non-human (e.g., murine) immunoglobulin, which has been engineered to contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, or hamster) that have the desired specificity, affinity, and capability (Jones et al., 1986, *Nature*, 321:522-525; Riechmann et al., 1988, *Nature*, 332:323-327; Verhoeyen et al., 1988, *Science*, 239:1534-1536). In some instances, the Fv framework region (FW) residues of a human immunoglobulin are replaced with the corresponding residues in an antibody from a non-human species that has the desired specificity, affinity, and capability.

The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539 or 5,639,641.

A "variable region" of an antibody refers to the variable region of the antibody light chain or the variable region of the antibody heavy chain, either alone or in combination. The variable regions of the heavy and light chain each consist of four framework regions (FW) connected by three complementarity determining regions (CDRs) also known as hypervariable regions. The CDRs in each chain are held together in close proximity by the FW regions and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al. (1997) *J. Molec. Biol.*

273:927-948)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g., Kabat et al., Sequences of Immunological Interest, 5th Ed. Public Health Service, National Institutes of Health, Bethesda, Md. (1991)).

The amino acid position numbering as in Kabat, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FW or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FW residue 82.

TABLE 1

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | | (Kabat Numbering) | |
| H1 | H31-H35 | H26-H35 | H26-H32 |
| | | (Chothia Numbering) | |
| H2 | H50-H65 | H50-H58 | H52-H56 |
| H3 | H95-H102 | H95-H102 | H95-H102 |

The Kabat numbering of residues can be determined for a given antibody by alignment at regions of homology of the sequence of the antibody with a "standard" Kabat numbered sequence. Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

As used herein the Fc region includes the polypeptides comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM Fc can include the J chain. For IgG, Fc comprises immunoglobulin domains Cgamma2 and Cgamma3 (Cγ2 and Cγ3) and the hinge between Cgamma1 (Cγ1) and Cgamma2 (Cγ2). Although the boundaries of the Fc region can vary, the human IgG heavy chain Fc region is usually defined to comprise residues C226 or P230 to its carboxyl-terminus, wherein the numbering is according to the EU index as set forth in Kabat (Kabat et al., Sequences of Proteins of Immunological Interest, 5th Ed. Public Health Service, National Institutes of Health, Bethesda, Md. (1991)). Fc can refer to this region in isolation, or this region in the context of an antibody, antibody fragment, or Fc fusion protein. Polymorphisms have been observed at a number of different Fc positions, including but not limited to positions 270, 272, 312, 315, 356, and 358 as numbered by the EU index, and thus slight differences between the presented sequence and sequences in the prior art may exist.

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and capability while the constant regions are homologous to the sequences in antibodies derived from another (usually human) to avoid eliciting an immune response in that species.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure.

The term "bispecific antibody" as used herein refers to an antibody that has binding sites for two different antigens within a single antibody molecule. It will be appreciated that other molecules in addition to the canonical antibody structure can be constructed with two binding specificities. It will further be appreciated that antigen binding by bispecific antibodies can be simultaneous or sequential. Triomas and hybrid hybridomas are two examples of cell lines that can secrete bispecific antibodies. Bispecific antibodies can also be constructed by recombinant means.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

An antibody is said to "competitively inhibit" binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

The term "YTE" mutations refers to a combination of the three mutations, M252Y, S254T, and T256E, wherein the numbering is according to the EU index as set forth in Kabat, introduced into the heavy chain of an IgG. See U.S. Pat. No. 7,658,921, which is herein incorporated by reference in its entirety.

Terms such as "treating" or "treatment" or "to treat" or "alleviating" or "to alleviate" refer to therapeutic measures that cure, slow down, lessen symptoms of, and/or halt progression of a diagnosed pathologic condition or disorder, e.g., infection. Thus, those in need of treatment include those already diagnosed with or suspected of having the disorder. In certain embodiments, a subject is successfully "treated" for a microbial infection according to the methods of the present disclosure if the patient shows one or more of the following: a reduction in the symptoms of microbial infection, a reduction in the number or a complete absence of the microbe in the patient (e.g., as assessed using a sample obtained from the patient), reduction in the amount or complete absence of an indicator of the microbe (e.g., alpha toxin of *S. aureus*) in the patient, and/or a reduction in the severity and/or frequency of a symptom or symptoms of the infection.

Prophylactic or preventative measures refer to measures that prevent and/or slow the development of a targeted pathological condition or disorder, e.g., infection. Thus, those in need of prophylactic or preventative measures include those prone to have the disorder and those in whom the disorder is to be prevented.

The term "pharmaceutical formulation" "pharmaceutical composition" refers to a preparation which is in such form as to permit the biological activity of the active ingredient to be effective, and which contains no additional components which are unacceptably toxic to a subject to which the formulation would be administered. The formulation can be sterile.

An "effective amount" of an antibody or immunoconjugate as disclosed herein is an amount sufficient to carry out a specifically stated purpose. An "effective amount" can be determined empirically and in a routine manner, in relation to the stated purpose.

Administration "in combination with" one or more further therapeutic agents includes simultaneous (concurrent) and consecutive administration in any order.

Anti-*Staphylococcus* Antibodies and Antigen-Binding Fragments Thereof

In certain aspects, the antibody or antigen-binding fragment thereof for use according to the methods provided herein specifically binds to a *Staphylococcus* antigen (e.g., polypeptide and/or carbohydrate).

In certain aspects, the antibody or antigen-binding fragment thereof specifically binds to a *Staphylococcus aureus* antigen (e.g., polypeptide and/or carbohydrate). *S. aureus* expresses a number of virulence factors, including capsular polysaccharides and protein toxins. One virulence factor often associated with *S. aureus* infection that is the major cytotoxic agent is alpha toxin (also known as alpha-hemolysin or Hla), a pore-forming and hemolytic exoprotein produced by most pathogenic strains of *S. aureus*. The toxin forms heptameric pores in membranes of susceptible cells such as white blood cells, platelets, erythrocytes, peripheral blood monocytes, macrophages, keratinocytes, fibroblasts and endothelial cells. Alpha toxin pore formation often leads to cell dysfunction or lysis. Accordingly, in certain aspects, the antibody or antigen-binding fragment thereof specifically binds to *Staphylococcus aureus* alpha toxin. In certain aspects, the *S. aureus* alpha toxin comprises the amino acid sequence of SEQ ID NO:70.

In certain aspects, the antibody or antigen-binding fragment thereof that specifically binds to *S. aureus* alpha toxin is an antibody or an antigen-binding fragment thereof disclosed in US 2014/0072577 (which is herein incorporated by reference in its entirety). In certain aspects, the antibody or antigen-binding fragment thereof that specifically binds to *S. aureus* alpha toxin is an antibody or an antigen-binding fragment thereof disclosed in WO 2012/109285 (which is herein incorporated by reference in its entirety).

In certain aspects, the antibody or antigen-binding fragment thereof that specifically binds to *S. aureus* alpha toxin binds to the same alpha toxin epitope as 2A3.1, 10A7.5, 12B8.19, 28F6.1, 25E9.1, QD20, QD33, QD37, QD3, QD4, QD23, QD32, 2A3GL, LC10, TVES, 3H7KAD, LC9, LC4, or LC5 (listed in Table 2 below). In certain aspects, the antibody or antigen-binding fragment thereof that specifically binds to *S. aureus* alpha toxin binds to the same alpha toxin epitope as LC10. In certain aspects, the antibody or antigen-binding fragment thereof that specifically binds to *S. aureus* alpha toxin competitively inhibits the binding of 2A3.1, 10A7.5, 12B8.19, 28F6.1, 25E9.1, QD20, QD33, QD37, QD3, QD4, QD23, QD32, 2A3GL, LC10, TVES, 3H7KAD, LC9, LC4, or LC5 to *S. aureus* alpha toxin. In certain aspects, the antibody or antigen-binding fragment thereof that specifically binds to *S. aureus* alpha toxin competitively inhibits the binding of LC10 to *S. aureus* alpha toxin.

TABLE 2

Anti-Alpha Toxin Antibody Sequence SEQ ID NOs

| Antibody | VL | VL CDR1 | VL CDR2 | VL CDR3 | VH | VH CDR1 | VH CDR2 | VH CDR3 |
|---|---|---|---|---|---|---|---|---|
| 2A3.1 | 19 | 1 | 2 | 3 | 20 | 7 | 8 | 9 |
| 10A7.5 | 21 | 1 | 2 | 3 | 22 | 10 | 11 | 12 |
| 12B8.19 | 23 | 1 | 2 | 3 | 24 | 10 | 11 | 12 |

TABLE 2-continued

Anti-Alpha Toxin Antibody Sequence SEQ ID NOs

| Antibody | VL | VL CDR1 | VL CDR2 | VL CDR3 | VH | VH CDR1 | VH CDR2 | VH CDR3 |
|---|---|---|---|---|---|---|---|---|
| 28F6.1 | 25 | 4 | 5 | 6 | 26 | 13 | 14 | 15 |
| 25E9.1 | 27 | 1 | 2 | 3 | 28 | 7 | 17 | 18 |
| QD20 | 30 | 1 | 2 | 52 | 29 | 7 | 8 | 16 |
| QD33 | 32 | 1 | 2 | 52 | 31 | 7 | 8 | 53 |
| QD37 | 34 | 1 | 2 | 52 | 33 | 7 | 8 | 54 |
| QD3 | 36 | 1 | 2 | 56 | 35 | 7 | 8 | 55 |
| QD4 | 38 | 1 | 2 | 52 | 37 | 7 | 8 | 55 |
| QD23 | 40 | 1 | 2 | 52 | 39 | 7 | 8 | 66 |
| QD32 | 42 | 1 | 2 | 56 | 41 | 7 | 8 | 53 |
| 2A3GL | 44 | 1 | 2 | 3 | 43 | 7 | 8 | 9 |
| LC10 | 46 | 1 | 2 | 56 | 45 | 57 | 58 | 59 |
| TVES | 48 | 1 | 61 | 62 | 47 | 7 | 8 | 60 |
| 3H7KAD | 46 | 1 | 2 | 56 | 49 | 57 | 63 | 59 |
| LC9 | 46 | 1 | 2 | 56 | 50 | 57 | 63 | 64 |
| LC4 | 51 | 1 | 65 | 62 | 50 | 57 | 63 | 64 |
| LC5 | 51 | 1 | 65 | 62 | 67 | 57 | 58 | 59 |

In certain aspects, the antibody or antigen-binding fragment thereof that specifically binds to S. aureus alpha toxin binds to the same alpha toxin epitope as an antibody comprising the heavy chain variable region (VH) and light chain variable region (VL) sequences of SEQ ID NOs:20 and 19; SEQ ID NOs; 22 and 21; SEQ ID NOs:24 and 23; SEQ ID NOs:26 and 25; SEQ ID NOs:28 and 27; SEQ ID NOs:29 and 30; SEQ ID NOs:31 and 32; SEQ ID NOs:33 and 34; SEQ ID NOs:35 and 36; SEQ ID NOs:37 and 38; SEQ ID NOs:39 and 40; SEQ ID NOs:41 and 42; SEQ ID NOs:43 and 44; SEQ ID NOs:45 and 46; SEQ ID NOs:47 and 48; SEQ ID NOs:49 and 46; SEQ ID NOs:50 and 46; SEQ ID NOs:50 and 51; or SEQ ID NOs:67 and 51. In certain aspects, the antibody or antigen-binding fragment thereof that specifically binds to S. aureus alpha toxin binds to the same alpha toxin epitope as an antibody comprising the VH and VL sequences of SEQ ID NOs:45 and 46.

In certain aspects, the antibody or antigen-binding fragment thereof that specifically binds to S. aureus alpha toxin competitively inhibits the binding of an antibody comprising the VH and VL sequences of SEQ ID NOs:20 and 19; SEQ ID NOs; 22 and 21; SEQ ID NOs:24 and 23; SEQ ID NOs:26 and 25; SEQ ID NOs:28 and 27; SEQ ID NOs:29 and 30; SEQ ID NOs:31 and 32; SEQ ID NOs:33 and 34; SEQ ID NOs:35 and 36; SEQ ID NOs:37 and 38; SEQ ID NOs:39 and 40; SEQ ID NOs:41 and 42; SEQ ID NOs:43 and 44; SEQ ID NOs:45 and 46; SEQ ID NOs:47 and 48; SEQ ID NOs:49 and 46; SEQ ID NOs:50 and 46; SEQ ID NOs:50 and 51; or SEQ ID NOs:67 and 51 to S. aureus alpha toxin. In certain aspects, the antibody or antigen-binding fragment thereof that specifically binds to S. aureus alpha toxin competitively inhibits the binding of an antibody comprising the VH and VL sequences of SEQ ID NOs:45 and 46 to S. aureus alpha toxin.

In certain aspects, the antibody or antigen-binding fragment thereof that specifically binds to S. aureus alpha toxin is an antibody or antigen-binding fragment thereof comprising (a) a VH CDR1 comprising the amino acid sequence of SEQ ID NO:7, 10, 13, or 57; (b) a VH CDR2 comprising the amino acid sequence of SEQ ID NO:8, 11, 14, 17, 58, or 63; (c) a VH CDR3 comprising the amino acid sequence of SEQ ID NO:9, 12, 15, 18, 16, 53, 54, 55, 59, 60, 64, or 66; (d) a VL CDR1 comprising the amino acid sequence of SEQ ID NO:1 or 4; (e) a VL CDR2 comprising the amino acid sequence of SEQ ID NO:2, 5, 61, or 65; and (f) a VL CDR3 comprising the amino acid sequence of SEQ ID NO:3, 6, 52, 56, or 62.

In certain aspects, the VH CDR1, VH CDR2, VH CDR3, VL CDR1, VL CDR2, and VL CDR3 comprise the amino acid sequences of SEQ ID NOs:7, 8, 9, 1, 2, and 3; SEQ ID NOs:10, 11, 12, 1, 2, and 3; SEQ ID NOs:13, 14, 15, 4, 5, and 6; SEQ ID NOs:7, 17, 18, 1, 2, and 3; SEQ ID NOs:7, 8, 16, 1, 2, and 52; SEQ ID NOs:7, 8, 53, 1, 2, and 52; SEQ ID NOs; 7, 8, 54, 1, 2, and 52; SEQ ID NOs:7, 8, 55, 1, 2, and 56; SEQ ID NOs:7, 8, 55, 1, 2, and 52; SEQ ID NOs:7, 8, 66, 1, 2, and 52; SEQ ID NOs:7, 8, 53, 1, 2, and 56; SEQ ID NOs:57, 58, 59, 1, 2, and 56; SEQ ID NOs:7, 8, 60, 1, 61, and 62; SEQ ID NOs:57, 63, 59, 1, 2, and 56; SEQ ID NOs:57, 63, 64, 1, 2, and 56; SEQ ID NOs:57, 63, 64, 1, 65, and 62; or SEQ ID NOs:57, 58, 59, 1, 65, and 67. In certain aspects, the VH CDR1, VH CDR2, VH CDR3, VL CDR1, VL CDR2, and VL CDR3 correspond to the amino acid sequences of SEQ ID NOs:57, 58, 59, 1, 2, and 56.

In certain aspects, the antibody or antigen-binding fragment thereof that specifically binds to S. aureus alpha toxin comprises VH having at least 75% identity to the amino acid sequence of SEQ ID NO:20, 22, 24, 26, 28, 29, 31, 33, 35, 37, 39, 41, 43, 45, 47, 49, 50, or 67 and comprises a VL having at least 75% identity to the amino acid sequence of SEQ ID NO:19, 21, 23, 25, 27, 30, 32, 34, 36, 38, 40, 42, 44, 46, 48 or 51. In certain aspects, the antibody or antigen-binding fragment thereof that specifically binds to S. aureus alpha toxin comprises a VH having at least 80% identity to the amino acid sequence of SEQ ID NO:20, 22, 24, 26, 28, 29, 31, 33, 35, 37, 39, 41, 43, 45, 47, 49, 50, or 67 and comprises a VL having at least 80% identity to the amino acid sequence of SEQ ID NO:19, 21, 23, 25, 27, 30, 32, 34, 36, 38, 40, 42, 44, 46, 48 or 51. In certain aspects, the antibody or antigen-binding fragment thereof that specifically binds to S. aureus alpha toxin comprises a VH having at least 85% identity to the amino acid sequence of SEQ ID NO:20, 22, 24, 26, 28, 29, 31, 33, 35, 37, 39, 41, 43, 45, 47, 49, 50, or 67 and comprises a VL having at least 85% identity to the amino acid sequence of SEQ ID NO:19, 21, 23, 25, 27, 30, 32, 34, 36, 38, 40, 42, 44, 46, 48 or 51. In certain aspects, the antibody or antigen-binding fragment thereof that specifically binds to S. aureus alpha toxin comprises a VH having at least 90% identity to the amino acid sequence of SEQ ID NO:20, 22, 24, 26, 28, 29, 31, 33, 35, 37, 39, 41, 43, 45, 47, 49, 50, or 67 and comprises VL having at least 90% identity to the amino acid sequence of SEQ ID NO:19, 21, 23, 25, 27, 30, 32, 34, 36, 38, 40, 42, 44, 46, 48 or 51. In certain aspects, the antibody or antigen-binding fragment thereof that specifically binds to S. aureus alpha toxin comprises a VH having at least 95% identity to the amino acid sequence of SEQ ID NO:20, 22, 24, 26, 28, 29, 31, 33, 35, 37, 39, 41, 43, 45, 47, 49, 50, or 67 and comprises a VL having at least 95% identity to the amino acid sequence of SEQ ID NO:19, 21, 23, 25, 27, 30, 32, 34, 36, 38, 40, 42, 44, 46, 48 or 51. In certain aspects, the antibody or antigen-binding fragment thereof that specifically binds to S. aureus alpha toxin comprises a VH having at least 98% identity to the amino acid sequence of SEQ ID NO:20, 22, 24, 26, 28, 29, 31, 33, 35, 37, 39, 41, 43, 45, 47, 49, 50, or 67 and comprises a VL having at least 98% identity to the amino acid sequence of SEQ ID NO:19, 21, 23, 25, 27, 30, 32, 34, 36, 38, 40, 42, 44, 46, 48 or 51. In certain aspects, the antibody or antigen-binding fragment thereof that specifically binds to S. aureus alpha toxin comprises a VH having at least 99% identity to the amino acid sequence of SEQ ID NO:20, 22, 24, 26, 28, 29, 31, 33, 35, 37, 39, 41, 43, 45, 47, 49, 50, or 67 and comprises a VL having at least 99% identity to the amino acid sequence of SEQ ID NO:19, 21, 23, 25, 27, 30, 32, 34, 36, 38, 40, 42, 44, 46, 48 or 51.

In certain aspects, the VH and VL correspond to the amino acid sequences of SEQ ID NOs:20 and 19; SEQ ID NOs: 22 and 21; SEQ ID NOs:24 and 23; SEQ ID NOs:26 and 25; SEQ ID NOs:28 and 27; SEQ ID NOs:29 and 30; SEQ ID NOs:31 and 32; SEQ ID NOs:33 and 34; SEQ ID NOs:35 and 36; SEQ ID NOs:37 and 38; SEQ ID NOs:39 and 40; SEQ ID NOs:41 and 42; SEQ ID NOs:43 and 44; SEQ ID NOs:45 and 46; SEQ ID NOs:47 and 48; SEQ ID NOs:49 and 46; SEQ ID NOs:50 and 46; SEQ ID NOs:50 and 51; or SEQ ID NOs:67 and 51. In certain aspects, the VH and VL correspond to the amino acid sequences of SEQ ID NOs:45 and 46.

In certain aspects, the antibody or antigen-binding fragment thereof that specifically binds to S. aureus alpha toxin comprises a heavy chain comprising the amino acid sequence of SEQ ID NO:68 and a light chain comprising the amino acid sequence of SEQ ID NO:69 (i.e., MEDI4893).

In certain aspects, the antibody or antigen-binding fragment thereof that specifically binds to S. aureus alpha toxin binds to a fragment of the S. aureus alpha toxin of SEQ ID NO:70 comprising (a) amino acids 261-272 of SEQ ID NO:70; (b) amino acids 173-201 of SEQ ID NO:70; (c) amino acids 261-272 of SEQ ID NO:70 and amino acids 173-201 of SEQ ID NO:70; or (d) amino acids 248-277 of SEQ ID NO:70. In certain aspects, the antibody or antigen-binding fragment thereof that specifically binds to S. aureus alpha toxin binds to a fragment of the S. aureus alpha toxin of SEQ ID NO:70 consisting of (a) amino acids 261-272 of SEQ ID NO:70; (b) amino acids 173-201 of SEQ ID NO:70; (c) amino acids 261-272 of SEQ ID NO:70 and amino acids 173-201 of SEQ ID NO:70; or (d) amino acids 248-277 of SEQ ID NO:70.

In certain aspects, the antibody or antigen-binding fragment thereof that specifically binds to S. aureus alpha toxin (a) has an affinity constant ($K_D$) for alpha toxin of about 13 nM or less; (b) binds to alpha toxin monomers, but does not inhibit binding of alpha toxin to alpha toxin receptor; (c) inhibits the formation of alpha toxin oligomers by at least 50%, 60%, 70%, 80%, 90%, or 95%; (d) reduces alpha toxin cytolytic activity by at least 50%, 60%, 70%, 80%, 90%, or 95% (e.g., as determined by cell lysis and hemolysis assays); (e) reduces cell infiltration and pro-inflammatory cytokine release; or (f) a combination thereof.

In certain embodiments, an antibody or antigen-binding fragment thereof as described herein specifically binds to an S. aureus epitope (e.g., alpha toxin) with an affinity characterized by a dissociation constant (KD) no greater than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

In certain embodiments, an anti-alpha toxin antibody or antigen-binding fragment alters the biological properties of alpha toxin, alpha toxin expressing cells, or other bacterial cells. In certain aspects, an anti-alpha toxin antibody or antigen-binding fragment neutralizes the biological activity of alpha toxin by binding to the polypeptide and inhibiting the assembly of alpha toxin monomers into a transmembrane pore (e.g., alpha toxin heptamer). Neutralization assays can be performed using methods known in the art using, in some circumstances, commercially available reagents. Neutralization of alpha toxin often is measured with an IC50 of $1\times10^{-6}$ M or less, $1\times10^{-7}$ M or less, $1\times10^{-8}$ M or less, $1\times10^{-9}$ M or less, $1\times10^{-10}$ M or less and $1\times10^{-11}$ M or less. In certain embodiments, an anti-alpha toxin antibody or fragment neutralizes the ability of alpha toxin to oligomerize and form a transmembrane pore. The term "inhibitory concentration 50%" (abbreviated as "IC50") represents the concentration of an inhibitor (e.g., an anti-alpha toxin antibody or fragment provided herein) that is required for 50% inhibition of a given activity of the molecule the inhibitor targets (e.g., alpha toxin oligomerization to form a transmembrane pore heptamer complex). A lower IC50 value generally corresponds to a more potent inhibitor.

In certain embodiments, an anti-alpha toxin antibody or fragment inhibits one or more biological activities of alpha toxin. The term "inhibition" as used herein, refers to any statistically significant decrease in biological activity, including full blocking of the activity. For example, "inhibition" can refer to a decrease of about 10%, 20%, 30%, 40%, 50%, 60%, 70%, 80%, 90%, or 100% in biological activity. In certain embodiments, an anti-alpha toxin antibody or fragment inhibits one or more biological activities of alpha toxin by at least 10%, 20%, 30%, 40%, 50%, 60%, 70%, 80%, 90%, or 100%.

In certain aspects, an anti-alpha toxin antibody or fragment can deplete alpha toxin secreted by pathogenic S. aureus. In certain aspects, an anti-alpha toxin antibody or fragment may achieve at least about 20%, at least about 30%, at least about 40%, at least about 50%, at least about 60%, at least about 70%, at least about 80%, at least about 90%, at least about 95%, or about 100% depletion of alpha toxin secreted by S. aureus.

In certain embodiments, an anti-alpha toxin antibody or fragment can inhibit in vitro stimulated alpha toxin activity (e.g., receptor binding, oligomerization) and/or proliferation of cells expressing or secreting alpha toxin. An anti-alpha toxin antibody or fragment sometimes inhibits in vitro alpha toxin activity, S. aureus pathogenicity by at least about 10%, at least about 20%, at least about 30%, at least about 40%, at least about 50% or at least about 75%. Methods for measuring cell proliferation, pathogenicity, and alpha hemolysin activity are known in the art.

In certain embodiments, an anti-alpha toxin antibody or antigen-binding fragment can inhibit the expression of one or more inducible genes that responds directly or indirectly to the environment created by S. aureus infection and/or alpha toxin expression and function. In specific embodiments, an anti-alpha toxin antibody or antigen-binding fragment inhibits the expression of one or more inducible genes that responds directly or indirectly to the environment created by *S. aureus* infection and/or alpha toxin expression and function by at least 20%, by at least 30%, by at least 40%, by at least 50%, by at least 60%, by at least 70%, by at least 80%, by at least 90%, by at least 100%, by at least 120%, by at least 140%, by at least 160%, by at least 180%, or by at least 200%

Anti-*Pseudomonas* Antibodies and Antigen-Binding Fragments Thereof

In certain aspects, the antibody or antigen-binding fragment thereof for use according to the methods provided herein specifically binds to a *Pseudomonas* antigen (e.g., polypeptide and/or carbohydrate). In certain aspects, the antibody or antigen-binding fragment thereof binds to a *Pseudomonas fluorescens*, *Pseudomonas putida*, *Pseudomonas alcaligenes*, or *Pseudomonas aeruginosa* antigen (e.g., polypeptide and/or carbohydrate). In certain aspects, the antibody or antigen-binding fragment thereof specifically binds to a *Pseudomonas aeruginosa* antigen (e.g., polypeptide and/or carbohydrate).

In certain aspects, the antibody or antigen-binding fragment thereof specifically binds to *P. aeruginosa* Psl exopolysaccharide. Psl exopolysaccharide is a repeating pentasaccharide polymer consisting of D-mannose, L-rhamnose, and D-glucose. Psl1 is reported to be anchored to the surface of *P. aeruginosa* and is thought to be important in facilitating colonization of host tissues and in establishing/maintaining biofilm formation.

In certain aspects, the antibody or antigen-binding fragment thereof that specifically binds to *P. aeruginosa* Psl is an antibody or an antigen-binding fragment thereof disclosed in WO 2012/170807, WO 2013/070615, or WO 2014/074528 (each of which is herein incorporated by reference in its entirety).

In certain aspects, the antibody or antigen-binding fragment thereof that specifically binds to *P. aeruginosa* Psl binds to the same *P. aeruginosa* Psl epitope as Cam-003, Cam-004, Cam-005, WapR-001, WapR-002, WapR-003, WapR-004, WapR -007, WapR-016, or WapR-004RAD (as disclosed in WO 2012/170807, which is herein incorporated by reference in its entirety). In certain aspects, the antibody or antigen-binding fragment thereof that specifically binds to *P. aeruginosa* Psl competitively inhibits the binding of Cam-003, Cam-004, Cam-005, WapR-001, WapR-002, WapR -003, WapR-004, WapR-007, WapR-016, or WapR-004RAD to *P. aeruginosa* Psl.

In certain aspects, the antibody or antigen-binding fragment thereof that specifically binds to *P. aeruginosa* Psl is an antibody or antigen-binding fragment thereof comprising VH CDR1, VH CDR2, VH, VL CDR1, VL CDR2, and VL CDR3 sequences comprising the VH CDR1, VH CDR2, VH, VL CDR1, VL CDR2, and VL CDR3 sequences of Cam-003, Cam-004, Cam-005, WapR-001, WapR-002, WapR-003, WapR -004, WapR-007, WapR-016, or WapR-004RAD.

In certain aspects, the antibody or antigen-binding fragment thereof that specifically binds to *P. aeruginosa* Psl comprises a heavy chain variable domain (VH) and a light chain variable region (VL) having at least 75% identity to the VH and VL of Cam-003, Cam-004, Cam-005, WapR-001, WapR-002, WapR-003, WapR-004, WapR -007, WapR-016, or WapR-004RAD. In certain aspects, the antibody or antigen-binding fragment thereof that specifically binds to *P. aeruginosa* Psl comprises a VH and a VL having at least 80% identity to the VH and VL of Cam-003, Cam-004, Cam-005, WapR -001, WapR-002, WapR-003, WapR-004, WapR-007, WapR-016, or WapR-004RAD. In certain aspects, the antibody or antigen-binding fragment thereof that specifically binds to *P. aeruginosa* Psl comprises a VH and a VL having at least 85% identity to the VH and VL of Cam-003, Cam-004, Cam-005, WapR-001, WapR-002, WapR-003, WapR-004, WapR-007, WapR-016, or WapR-004RAD. In certain aspects, the antibody or antigen-binding fragment thereof that specifically binds to *P. aeruginosa* Psl comprises a VH and a VL having at least 90% identity to the VH and VL of Cam-003, Cam-004, Cam-005, WapR-001, WapR-002, WapR-003, WapR-004, WapR-007, WapR-016, or WapR -004RAD. In certain aspects, the antibody or antigen-binding fragment thereof that specifically binds to *P. aeruginosa* Psl comprises a VH and a VL having at least 95% identity to the VH and VL of Cam-003, Cam-004, Cam-005, WapR-001, WapR-002, WapR-003, WapR-004, WapR-007, WapR-016, or WapR-004RAD. In certain aspects, the antibody or antigen-binding fragment thereof that specifically binds to *P. aeruginosa* Psl comprises a VH and a VL having at least 98% identity to the VH and VL of Cam-003, Cam-004, Cam-005, WapR-001, WapR-002, WapR-003, WapR-004, WapR-007, WapR -016, or WapR-004RAD. In certain aspects, the antibody or antigen-binding fragment thereof that specifically binds to *P. aeruginosa* Psl comprises a VH and a VL having at least 99% identity to the VH and VL of Cam-003, Cam-004, Cam-005, WapR-001, WapR-002, WapR-003, WapR-004, WapR-007, WapR-016, or WapR-004RAD. In certain aspects, the antibody or antigen-binding fragment thereof that specifically binds to *P. aeruginosa* Psl comprises a VH and a VL having the sequences of the VH and VL of Cam-003, Cam-004, Cam-005, WapR-001, WapR-002, WapR-003, WapR-004, WapR -007, WapR-016, or WapR-004RAD.

In certain aspects, the antibody or antigen-binding fragment thereof that specifically binds to *P. aeruginosa* Psl binds to the same *P. aeruginosa* Psl epitope as WapR-004, WapR-004RAD, or Ps10096. In certain aspects, the antibody or antigen-binding fragment thereof that specifically binds to *P. aeruginosa* competitively inhibits the binding of WapR-004, WapR-004RAD, or Ps10096 to *P. aeruginosa* Psl. The sequences of the WapR-004, WapR-004RAD, and Ps10096 are provided in Table 3 below.

TABLE 3

Anti-*P. aeruginosa* Psl Antibody Sequence SEQ ID NOs

| Antibody | VL | VL CDR1 | VL CDR2 | VL CDR3 | VH | VH CDR1 | VH CDR2 | VH CDR3 |
|---|---|---|---|---|---|---|---|---|
| WapR-004 | 72 | 76 | 77 | 78 | 71 | 73 | 74 | 75 |
| WapR-004RAD | 72 | 76 | 77 | 78 | 79 | 73 | 74 | 80 |
| Ps10096 | 97 | 76 | 77 | 95 | 96 | 73 | 74 | 94 |

In certain aspects, the antibody or antigen-binding fragment thereof that specifically binds to P. aeruginosa Psl binds to the same epitope as an antibody comprising the VH and VL sequences of SEQ ID NOs:71 and 72; SEQ ID NOs:79 and 72; or SEQ ID NOs:96 and 97. In certain aspects, the antibody or antigen-binding fragment thereof that specifically binds to P. aeruginosa Psl binds to the same epitope as an antibody comprising the VH and VL sequences of SEQ ID NOs:79 and 72. In certain aspects, the antibody or antigen-binding fragment thereof that specifically binds to P. aeruginosa Psl binds to the same epitope as an antibody comprising the VH and VL sequences of SEQ ID NOs:96 and 97.

In certain aspects, the antibody or antigen-binding fragment thereof that specifically binds to P. aeruginosa Psl competitively inhibits the binding of an antibody comprising the VH and VL sequences of SEQ ID NOs:71 and 72; SEQ ID NOs:79 and 72; or SEQ ID NOs:96 and 97 to P. aeruginosa Psl. In certain aspects, the antibody or antigen-binding fragment thereof that specifically binds to P. aeruginosa Psl toxin competitively inhibits the binding of an antibody comprising the VH and VL sequences of SEQ ID NOs:79 and 72 to P. aeruginosa Psl. In certain aspects, the antibody or antigen-binding fragment thereof that specifically binds to P. aeruginosa Psl toxin competitively inhibits the binding of an antibody comprising the VH and VL sequences of SEQ ID NOs:96 and 97 to P. aeruginosa Psl.

In certain aspects, the VH CDR1, VH CDR2, VH CDR3, VL CDR1, VL CDR2, and VL CDR3 correspond to the amino acid sequences of SEQ ID NOs:73, 74, 75, 76, 77, and 78; or SEQ ID NOs:73, 74, 80, 76, 77, and 78. In certain aspects, the VH CDR1, VH CDR2, VH CDR3, VL CDR1, VL CDR2, and VL CDR3 correspond to the amino acid sequences of SEQ ID NOs:73, 74, 80, 76, 77, and 78. In certain aspects, the VH CDR1, VH CDR2, VH CDR3, VL CDR1, VL CDR2, and VL CDR3 correspond to the amino acid sequences of SEQ ID NOs:73, 74, 94, 76, 77, and 95.

In certain aspects, the antibody or antigen-binding fragment thereof that specifically binds to P. aeruginosa Psl comprises a VH having at least 75% identity to the amino acid sequence of SEQ ID NO:71 or 79 and comprises a VL having at least 75% identity to the amino acid sequence of SEQ ID NO:72. In certain aspects, the antibody or antigen-binding fragment thereof that specifically binds to P. aeruginosa Psl comprises a VH having at least 75% identity to the amino acid sequence of SEQ ID NO:71 or 79 and comprises a VL having at least 75% identity to the amino acid sequence of SEQ ID NO:72. In certain aspects, the antibody or antigen-binding fragment thereof that specifically binds to P. aeruginosa Psl comprises a VH having at least 80% identity to the amino acid sequence of SEQ ID NO:71 or 79 and comprises a VL having at least 80% identity to the amino acid sequence of SEQ ID NO:72. In certain aspects, the antibody or antigen-binding fragment thereof that specifically binds to P. aeruginosa Psl comprises a VH having at least 85% identity to the amino acid sequence of SEQ ID NO:71 or 79 and comprises a VL having at least 85% identity to the amino acid sequence of SEQ ID NO:72. In certain aspects, the antibody or antigen-binding fragment thereof that specifically binds to P. aeruginosa Psl comprises a VH having at least 90% identity to the amino acid sequence of SEQ ID NO:71 or 79 and comprises a VL having at least 90% identity to the amino acid sequence of SEQ ID NO:72. In certain aspects, the antibody or antigen-binding fragment thereof that specifically binds to P. aeruginosa Psl comprises a VH having at least 95% identity to the amino acid sequence of SEQ ID NO:71 or 79 and comprises a VL having at least 95% identity to the amino acid sequence of SEQ ID NO:72. In certain aspects, the antibody or antigen-binding fragment thereof that specifically binds to P. aeruginosa Psl comprises a VH having at least 98% identity to the amino acid sequence of SEQ ID NO:71 or 79 and comprises a VL having at least 98% identity to the amino acid sequence of SEQ ID NO:72. In certain aspects, the antibody or antigen-binding fragment thereof that specifically binds to P. aeruginosa Psl comprises a VH having at least 99% identity to the amino acid sequence of SEQ ID NO:71 or 79 and comprises a VL having at least 99% identity to the amino acid sequence of SEQ ID NO:72. In certain aspects, the VH and VL comprise the amino acid sequences of SEQ ID NOs:71 and 72; or SEQ ID NOs:79 and 72. In certain aspects, the VH and VL comprise the amino acid sequences of SEQ ID NOs:79 and 72.

In certain aspects, the antibody or antigen-binding fragment thereof that specifically binds to P. aeruginosa Psl comprises a VH having at least 75% identity to the amino acid sequence of SEQ ID NO:96 and comprises a VL having at least 75% identity to the amino acid sequence of SEQ ID NO:97. In certain aspects, the antibody or antigen-binding fragment thereof that specifically binds to P. aeruginosa Psl comprises a VH having at least 75% identity to the amino acid sequence of SEQ ID NO:96 and comprises a VL having at least 75% identity to the amino acid sequence of SEQ ID NO:97. In certain aspects, the antibody or antigen-binding fragment thereof that specifically binds to P. aeruginosa Psl comprises a VH having at least 80% identity to the amino acid sequence of SEQ ID NO:96 and comprises a VL having at least 80% identity to the amino acid sequence of SEQ ID NO:97. In certain aspects, the antibody or antigen-binding fragment thereof that specifically binds to P. aeruginosa Psl comprises a VH having at least 85% identity to the amino acid sequence of SEQ ID NO:96 and comprises a VL having at least 85% identity to the amino acid sequence of SEQ ID NO:97. In certain aspects, the antibody or antigen-binding fragment thereof that specifically binds to P. aeruginosa Psl comprises a VH having at least 90% identity to the amino acid sequence of SEQ ID NO:96 and comprises a VL having at least 90% identity to the amino acid sequence of SEQ ID NO:97. In certain aspects, the antibody or antigen-binding fragment thereof that specifically binds to P. aeruginosa Psl comprises a VH having at least 95% identity to the amino acid sequence of SEQ ID NO:96 and comprises a VL having at least 95% identity to the amino acid sequence of SEQ ID NO:97. In certain aspects, the antibody or antigen-binding fragment thereof that specifically binds to P. aeruginosa Psl comprises a VH having at least 98% identity to the amino acid sequence of SEQ ID NO:96 and comprises a VL having at least 98% identity to the amino acid sequence of SEQ ID NO:97. In certain aspects, the antibody or antigen-binding fragment thereof that specifically binds to P. aeruginosa Psl comprises a VH having at least 99% identity to the amino acid sequence of SEQ ID NO:96 and comprises a VL having at least 99% identity to the amino acid sequence of SEQ ID NO:97. In certain aspects, the VH and VL comrpise the amino acid sequences of SEQ ID NOs:96 and 97.

In certain aspects, the antibody or antigen-binding fragment thereof that specifically binds to P. aeruginosa Psl is a germ-line optimized Wap-004-RAD. In certain aspects, the germ-line optimized Wap-004-RAD is Ps10096, Ps10170, Ps10225, Ps10304, Ps10337, Ps1348, Ps10567, Ps10573, Ps10574, Ps10582, Ps10584, Ps10585, Ps10588, or Ps10589 (as described in WO 2014/074528, which is herein incorporated by reference in its entirety). In certain aspects, the germ-line optimized Wap-004-RAD is Ps10096, Ps10225, Ps10337, Ps10567, or Ps10588. In certain aspects, the germ-line optimized Wap-004-RAD is Ps10096.

In certain aspects, the antibody or antigen-binding fragment thereof specifically binds to *P. aeruginosa* PcrV. PcrV is a relatively conserved component of the type III secretion system. PcrV appears to be an integral component of the translocation apparatus of the type III secretion system mediating the delivery of the type III secretory toxins into target eukaryotic cells. Active and passive immunization against PcrV improve acute lung injury and mortality of mice infected with cytotoxic *P. aeruginosa*. The major effect of immunization against PcrV is due to the blockade of translocation of the type III secretory toxins into eukaryotic cells. In certain aspects, the *P. aeruginosa* PcRv comprises the amino acid sequence of GenBank Accession No. AAC45935 or AA091771.

In certain aspects, the antibody or antigen-binding fragment thereof that specifically binds to *P. aeruginosa* PcrV is an antibody or an antigen-binding fragment thereof disclosed in WO 2013/070615 or WO 2014/074528 (which are herein incorporated by reference in their entireties).

In certain aspects, the antibody or antigen-binding fragment thereof that specifically binds to *P. aeruginosa* PcrV binds to the same *P. aeruginosa* PcrV epitope as 29D2, V2L2, V2L2-GL, V2L2-P4M, V2L2-MFS, V2L2-MD, or V2L2-MR (as provided in WO 2013/070615 and/or WO 2014/074528, each of which is herein incorporated by reference in its entirety). In certain aspects, the antibody or antigen-binding fragment thereof that specifically binds to *P. aeruginosa* competitively inhibits the binding of 29D2, V2L2, V2L2-GL, V2L2-P4M, V2L2-MFS, V2L2-MD, or V2L2-MR to *P. aeruginosa* PcrV.

In certain aspects, the antibody or antigen-binding fragment thereof that specifically binds to *P. aeruginosa* PcrV is an antibody or antigen-binding fragment thereof comprising VH CDR1, VH CDR2, VH, VL CDR1, VL CDR2, and VL CDR3 sequences comprising the VH CDR1, VH CDR2, VH, VL CDR1, VL CDR2, and VL CDR3 sequences of 29D2, V2L2, V2L2-GL, V2L2-P4M, V2L2-MFS, V2L2-MD, or V2L2-MR.

In certain aspects, the antibody or antigen-binding fragment thereof that specifically binds to *P. aeruginosa* PcrV comprises a VH and a VL having at least 75% identity to the VH and VL of 29D2, V2L2, V2L2-GL, V2L2-P4M, V2L2-MFS, V2L2-MD, or V2L2-MR. In certain aspects, the antibody or antigen-binding fragment thereof that specifically binds to *P. aeruginosa* PcrV comprises a VH and a VL having at least 80% identity to the VH and VL of 29D2, V2L2, V2L2-GL, V2L2-P4M, V2L2-MFS, V2L2-MD, or V2L2-MR. In certain aspects, the antibody or antigen-binding fragment thereof that specifically binds to *P. aeruginosa* PcrV comprises a VH and a VL having at least 85% identity to the VH and VL of 29D2, V2L2, V2L2-GL, V2L2-P4M, V2L2-MFS, V2L2-MD, or V2L2-MR. In certain aspects, the antibody or antigen-binding fragment thereof that specifically binds to *P. aeruginosa* PcrV comprises a VH and a VL having at least 90% identity to the VH and VL of 29D2, V2L2, V2L2-GL, V2L2-P4M, V2L2-MFS, V2L2-MD, or V2L2-MR. In certain aspects, the antibody or antigen-binding fragment thereof that specifically binds to *P. aeruginosa* PcrV comprises a VH and a VL having at least 95% identity to the VH and VL of 29D2, V2L2, V2L2-GL, V2L2-P4M, V2L2-MFS, V2L2-MD, or V2L2-MR. In certain aspects, the antibody or antigen-binding fragment thereof that specifically binds to *P. aeruginosa* PcrV comprises a VH and a VL having at least 98% identity to the VH and VL of 29D2, V2L2, V2L2-GL, V2L2-P4M, V2L2-MFS, V2L2-MD, or V2L2-MR. In certain aspects, the antibody or antigen-binding fragment thereof that specifically binds to *P. aeruginosa* PcrV comprises a VH and a VL having at least 99% identity to the VH and VL of 29D2, V2L2, V2L2-GL, V2L2-P4M, V2L2-MFS, V2L2-MD, or V2L2-MR.

In certain aspects, the antibody or antigen-binding fragment thereof that specifically binds to *P. aeruginosa* PcrV comprises a VH and a VL having the sequences of the VH and VL of 29D2, V2L2, V2L2-GL, V2L2-P4M, V2L2-MFS, V2L2-MD, or V2L2-MR.

In certain aspects, the antibody or antigen-binding fragment thereof that specifically binds to *P. aeruginosa* PcrV binds to the same *P. aeruginosa* PcrV epitope as V2L2. In certain aspects, the antibody or antigen-binding fragment thereof that specifically binds to *P. aeruginosa* competitively inhibits the binding of V2L2 to *P. aeruginosa* PcrV. The sequences of V2L2 and V2L2-MD are provided in Table 4 below.

TABLE 4

Anti-*P. aeruginosa* PcrV Antibody Sequence SEQ ID NOs

| Antibody | VL | VL CDR1 | VL CDR2 | VL CDR3 | VH | VH CDR1 | VH CDR2 | VH CDR3 |
|---|---|---|---|---|---|---|---|---|
| V2L2 | 82 | 86 | 87 | 88 | 81 | 83 | 84 | 85 |
| V2L2-MD | 99 | 86 | 87 | 88 | 98 | 83 | 84 | 85 |

In certain aspects, the antibody or antigen-binding fragment thereof that specifically binds to *P. aeruginosa* PcrV binds to the same PcrV epitope as an antibody comprising the VH and VL sequences of SEQ ID NOs:81 and 82 or SEQ ID NOs: 98 and 99. In certain aspects, the antibody or antigen-binding fragment thereof that specifically binds to *P. aeruginosa* PcrV competitively inhibits the binding of an antibody comprising the VH and VL sequences of SEQ ID NOs:81 and 82 or SEQ ID NOs: 98 and 99 to *P. aeruginosa* PcrV.

In certain aspects, the antibody or antigen-binding fragment thereof that specifically binds to *P. aeruginosa* PcrV is an antibody or antigen-binding fragment thereof comprising the VH CDR1, VH CDR2, VH CDR3, VL CDR1, VL CDR2, and VL CDR3 sequences of SEQ ID NOs:83-88.

In certain aspects, the antibody or antigen-binding fragment thereof that specifically binds to *P. aeruginosa* PcrV comprises a VH having at least 75% identity to the amino acid sequence of SEQ ID NO:81 and comprises a VL having at least 75% identity to the amino acid sequence of SEQ ID NO:82. In certain aspects, the antibody or antigen-binding fragment thereof that specifically binds to *P. aeruginosa* PcrV comprises a VH having at least 80% identity to the amino acid sequence of SEQ ID NO:81 and comprises a VL having at least 80% identity to the amino acid sequence of SEQ ID NO:82. In certain aspects, the antibody or antigen-binding fragment thereof that specifically binds to *P. aeruginosa* PcrV comprises a VH having at least 85% identity to the amino acid sequence of SEQ ID NO:81 and comprises a VL having at least 85% identity to the amino acid sequence of SEQ ID NO:82. In certain aspects, the antibody or antigen-binding fragment thereof that specifically binds to *P. aeruginosa* PcrV comprises a VH having at least 90% identity to the amino acid sequence of SEQ ID NO:81 and comprises a VL having at least 90% identity to the amino acid sequence of SEQ ID NO:82. In certain aspects, the antibody or antigen-binding fragment thereof that specifically binds to *P. aeruginosa* PcrV comprises a VH having at least 95% identity to the amino acid sequence of SEQ ID NO:81 and comprises a VL having at least 95% identity to the amino acid sequence of SEQ ID NO:82. In certain aspects, the antibody or antigen-binding fragment thereof that specifically binds to *P. aeruginosa* PcrV comprises a VH having at least 98% identity to the amino acid sequence of SEQ ID NO:81 and comprises a VL having at least 99% identity to the amino acid sequence of SEQ ID NO:82. In certain aspects, the antibody or antigen-binding fragment thereof that specifically binds to *P. aeruginosa* PcrV comprises a VH having at least 99% identity to the amino acid sequence of SEQ ID NO:81 and comprises a VL having at least 99% identity to the amino acid sequence of SEQ ID NO:82. In certain aspects, the VH and VL comprise the amino acid sequences of SEQ ID NOs:81 and 82.

In certain aspects, the antibody or antigen-binding fragment thereof that specifically binds to *P. aeruginosa* PcrV comprises a VH having at least 75% identity to the amino acid sequence of SEQ ID NO:98 and comprises a VL having at least 75% identity to the amino acid sequence of SEQ ID NO:99. In certain aspects, the antibody or antigen-binding fragment thereof that specifically binds to *P. aeruginosa* PcrV comprises a VH having at least 80% identity to the amino acid sequence of SEQ ID NO:98 and comprises a VL having at least 80% identity to the amino acid sequence of SEQ ID NO:99. In certain aspects, the antibody or antigen-binding fragment thereof that specifically binds to *P. aeruginosa* PcrV comprises a VH having at least 85% identity to the amino acid sequence of SEQ ID NO:98 and comprises a VL having at least 85% identity to the amino acid sequence of SEQ ID NO:99. In certain aspects, the antibody or antigen-binding fragment thereof that specifically binds to *P. aeruginosa* PcrV comprises a VH having at least 90% identity to the amino acid sequence of SEQ ID NO:98 and comprises a VL having at least 90% identity to the amino acid sequence of SEQ ID NO:99. In certain aspects, the antibody or antigen-binding fragment thereof that specifically binds to *P. aeruginosa* PcrV comprises a VH having at least 95% identity to the amino acid sequence of SEQ ID NO:98 and comprises a VL having at least 95% identity to the amino acid sequence of SEQ ID NO:99. In certain aspects, the antibody or antigen-binding fragment thereof that specifically binds to *P. aeruginosa* PcrV comprises a VH having at least 98% identity to the amino acid sequence of SEQ ID NO:98 and comprises a VL having at least 99% identity to the amino acid sequence of SEQ ID NO:99. In certain aspects, the antibody or antigen-binding fragment thereof that specifically binds to *P. aeruginosa* PcrV comprises a VH having at least 99% identity to the amino acid sequence of SEQ ID NO:98 and comprises a VL having at least 99% identity to the amino acid sequence of SEQ ID NO:99. In certain aspects, the VH and VL comprise the amino acid sequences of SEQ ID NOs:98 and 99.

In certain aspects, the antibody or antigen-binding fragment thereof that specifically binds to *P. aeruginosa* PcrV is a germ-line optimized V2L2. In certain aspects, the germ-line optimized V2L2 is V2L2 germlined Mab (V2L2-GL), or a V2L2-GL optimized Mab (e.g., V2L2-P4M, V2L2-MFS, V2L2-MD, or V2L2-MR) (as described in WO 2014/074528, which is herein incorporated by reference in its entirety).

In certain aspects, the antibody or antigen-binding fragment thereof that specifically binds to *P. aeruginosa* PcrV can disrupt the activity of the type III toxin secretion system.

In certain aspects, the antibody or antigen-binding fragment thereof is a bispecific antibody or antigen-binding fragment thereof that specifically binds to *P. aeruginosa* Psl and PcrV. In certain aspects, the antibody or antigen-binding fragment thereof that specifically binds to *P. aeruginosa* Psl and PcrV is an antibody or an antigen-binding fragment thereof disclosed in WO 2013/070615 and/or WO 2014/074528 (which are herein incorporated by reference in their entireties).

In certain aspects, the antibody or antigen-binding fragment thereof that specifically binds to *P. aeruginosa* Psl and PcrV binds to the same Psl epitope as an antibody comprising the VH and VL sequences of SEQ ID NOs:79 and 72 or SEQ ID NOs: 96 and 97. In certain aspects, the antibody or antigen-binding fragment thereof that specifically binds to *P. aeruginosa* Psl and PcrV binds to the same PcrV epitope as an antibody comprising the VH and VL sequences of SEQ ID NOs:81 and 82 or SEQ ID NOs: 98 and 99. In certain aspects, the antibody or antigen-binding fragment thereof that specifically binds to *P. aeruginosa* Psl and PcrV binds to the same Psl epitope as an antibody comprising the VH and VL sequences corresponding of SEQ ID NOs:79 and 72 or SEQ ID NOs: 96 and 97 and to the same PcrV epitope as an antibody comprising the VH and VL sequences of SEQ ID NOs:81 and 82 or SEQ ID NOs: 98 and 99.

In certain aspects, the antibody or antigen-binding fragment thereof that specifically binds to *P. aeruginosa* Psl and PcrV competitively inhibits the binding of an antibody comprising the VH and VL sequences of SEQ ID NOs:79 and 72 or SEQ ID NOs: 96 and 97 to *P. aeruginosa* Psl. In certain aspects, the antibody or antigen-binding fragment thereof that specifically binds to *P. aeruginosa* Psl and PcrV competitively inhibits the binding of an antibody comprising the VH and VL sequences of SEQ ID NOs:81 and 82 or SEQ ID NOs: 98 and 99 to *P. aeruginosa* PcrV. In certain aspects, the antibody or antigen-binding fragment thereof that specifically binds to *P. aeruginosa* Psl and PcrV competitively inhibits the binding of an antibody comprising the VH and VL sequences of SEQ ID NOs:79 and 72 or SEQ ID NOs: 96 and 97 to *P. aeruginosa* Psl and competitively inhibits the binding of an antibody comprising the VH and VL sequences of SEQ ID NOs:81 and 82 or SEQ ID NOs: 98 and 99 to *P. aeruginosa* PcrV.

In certain aspects, the antibody or antigen-binding fragment thereof that specifically binds to *P. aeruginosa* Psl and PcrV comprises the VH CDR1, VH CDR2, VH CDR3, VL CDR1, VL CDR2, and VL CDR3 sequences of SEQ ID NOs:73, 74, 80, 76, 77, and 78 or SEQ ID NOs: 73, 74, 94, 76, 77, and 95. In certain aspects, the antibody or antigen-binding fragment thereof that specifically binds to *P. aeruginosa* Psl and PcrV comprises the VH CDR1, VH CDR2, VH CDR3, VL CDR1, VL CDR2, and VL CDR3 sequences of SEQ ID NOs:83-88. In certain aspects, the antibody or antigen-binding fragment thereof that specifically binds to *P. aeruginosa* Psl and PcrV comprises the VH CDR1, VH CDR2, VH CDR3, VL CDR1, VL CDR2, and VL CDR3 sequences of SEQ ID NOs:73, 74, 80, 76, 77, and 78 or SEQ ID NOs: 73, 74, 94, 76, 77, and 95 and VH CDR1, VH CDR2, VH CDR3, VL CDR1, VL CDR2, and VL CDR3 sequences that correspond to the amino acid sequences of SEQ ID NOs:83-88.

In certain aspects, the antibody or antigen-binding fragment thereof that specifically binds to *P. aeruginosa* Psl and PcrV comprises a VH having at least 75% identity to the amino acid sequence of SEQ ID NO:79 and comprises a VL having at least 75% identity to the amino acid sequence of SEQ ID NO:72. In certain aspects, the antibody or antigen-binding fragment thereof that specifically binds to *P. aeruginosa* Psl and PcrV comprises a VH having at least 80% identity to the amino acid sequence of SEQ ID NO:79 and comprises a VL having at least 80% identity to the amino acid sequence of SEQ ID NO:72. In certain aspects, the antibody or antigen-binding fragment thereof that specifically binds to *P. aeruginosa* Psl and PcrV comprises a VH having at least 85% identity to the amino acid sequence of SEQ ID NO:79 and comprises a VL having at least 85% identity to the amino acid sequence of SEQ ID NO:72. In certain aspects, the antibody or antigen-binding fragment thereof that specifically binds to *P. aeruginosa* Psl and PcrV comprises a VH having at least 90% identity to the amino acid sequence of SEQ ID NO:79 and comprises a VL having at least 90% identity to the amino acid sequence of SEQ ID NO:72. In certain aspects, the antibody or antigen-binding fragment thereof that specifically binds to *P. aeruginosa* Psl and PcrV comprises a VH having at least 95% identity to the amino acid sequence of SEQ ID NO:79 and comprises a VL having at least 95% identity to the amino acid sequence of SEQ ID NO:72. In certain aspects, the antibody or antigen-binding fragment thereof that specifically binds to *P. aeruginosa* Psl and PcrV comprises a VH having at least 98% identity to the amino acid sequence of SEQ ID NO:79 and comprises a VL having at least 98% identity to the amino acid sequence of SEQ ID NO:72. In certain aspects, the antibody or antigen-binding fragment thereof that specifically binds to *P. aeruginosa* Psl and PcrV comprises a VH having at least 99% identity to the amino acid sequence of SEQ ID NO:79 and comprises a VL having at least 99% identity to the amino acid sequence of SEQ ID NO:72. In certain aspects, the antibody or antigen-binding fragment thereof that specifically binds to *P. aeruginosa* Psl and PcrV comprises a VH and a VL having the amino acid sequences of SEQ ID NOs:79 and 72.

In certain aspects, the antibody or antigen-binding fragment thereof that specifically binds to *P. aeruginosa* Psl and PcrV comprises a VH having at least 75% identity to the amino acid sequence of SEQ ID NO:96 and comprises a VL having at least 75% identity to the amino acid sequence of SEQ ID NO:97. In certain aspects, the antibody or antigen-binding fragment thereof that specifically binds to *P. aeruginosa* Psl and PcrV comprises a VH having at least 80% identity to the amino acid sequence of SEQ ID NO:96 and comprises a VL having at least 80% identity to the amino acid sequence of SEQ ID NO:97. In certain aspects, the antibody or antigen-binding fragment thereof that specifically binds to *P. aeruginosa* Psl and PcrV comprises a VH having at least 85% identity to the amino acid sequence of SEQ ID NO:96 and comprises a VL having at least 85% identity to the amino acid sequence of SEQ ID NO:97. In certain aspects, the antibody or antigen-binding fragment thereof that specifically binds to *P. aeruginosa* Psl and PcrV comprises a VH having at least 90% identity to the amino acid sequence of SEQ ID NO:96 and comprises a VL having at least 90% identity to the amino acid sequence of SEQ ID NO:97. In certain aspects, the antibody or antigen-binding fragment thereof that specifically binds to *P. aeruginosa* Psl and PcrV comprises a VH having at least 95% identity to the amino acid sequence of SEQ ID NO:96 and comprises a VL having at least 95% identity to the amino acid sequence of SEQ ID NO:97. In certain aspects, the antibody or antigen-binding fragment thereof that specifically binds to *P. aeruginosa* Psl and PcrV comprises a VH having at least 98% identity to the amino acid sequence of SEQ ID NO:96 and comprises a VL having at least 98% identity to the amino acid sequence of SEQ ID NO:97. In certain aspects, the antibody or antigen-binding fragment thereof that specifically binds to *P. aeruginosa* Psl and PcrV comprises a VH having at least 99% identity to the amino acid sequence of SEQ ID NO:96 and comprises a VL having at least 99% identity to the amino acid sequence of SEQ ID NO:97. In certain aspects, the antibody or antigen-binding fragment thereof that specifically binds to *P. aeruginosa* Psl and PcrV comprises a VH and a VL having the amino acid sequences of SEQ ID NOs:96 and 97.

In certain aspects, the antibody or antigen-binding fragment thereof that specifically binds to *P. aeruginosa* Psl and PcrV comprises a VH having at least 75% identity to the amino acid sequence of SEQ ID NO:81 and comprises a VL having at least 75% identity to the amino acid sequence of SEQ ID NO:82. In certain aspects, the antibody or antigen-binding fragment thereof that specifically binds to *P. aeruginosa* Psl and PcrV comprises a VH having at least 80% identity to the amino acid sequence of SEQ ID NO:81 and comprises a VL having at least 80% identity to the amino acid sequence of SEQ ID NO:82. In certain aspects, the antibody or antigen-binding fragment thereof that specifically binds to *P. aeruginosa* Psl and PcrV comprises a VH having at least 85% identity to the amino acid sequence of SEQ ID NO:81 and comprises a VL having at least 85% identity to the amino acid sequence of SEQ ID NO:82. In certain aspects, the antibody or antigen-binding fragment thereof that specifically binds to *P. aeruginosa* Psl and PcrV comprises a VH having at least 90% identity to the amino acid sequence of SEQ ID NO:81 and comprises a VL having at least 90% identity to the amino acid sequence of SEQ ID NO:82. In certain aspects, the antibody or antigen-binding fragment thereof that specifically binds to *P. aeruginosa* Psl and PcrV comprises a VH having at least 95% identity to the amino acid sequence of SEQ ID NO:81 and comprises a VL having at least 95% identity to the amino acid sequence of SEQ ID NO:82. In certain aspects, the antibody or antigen-binding fragment thereof that specifically binds to *P. aeruginosa* Psl and PcrV comprises a VH having at least 98% identity to the amino acid sequence of SEQ ID NO:81 and comprises a VL having at least 98% identity to the amino acid sequence of SEQ ID NO:82. In certain aspects, the antibody or antigen-binding fragment thereof that specifically binds to *P. aeruginosa* Psl and PcrV comprises a VH having at least 99% identity to the amino acid sequence of SEQ ID NO:81 and comprises a VL having at least 99% identity to the amino acid sequence of SEQ ID NO:82. In certain aspects, the antibody or antigen-binding fragment thereof that specifically binds to *P. aeruginosa* Psl and PcrV comprises a VH and a VL having the amino acid sequences of SEQ ID NOs:81 and 82.

In certain aspects, the antibody or antigen-binding fragment thereof that specifically binds to *P. aeruginosa* Psl and PcrV comprises a VH having at least 75% identity to the amino acid sequence of SEQ ID NO:98 and comprises a VL having at least 75% identity to the amino acid sequence of SEQ ID NO:99. In certain aspects, the antibody or antigen-binding fragment thereof that specifically binds to *P. aeruginosa* Psl and PcrV comprises a VH having at least 80% identity to the amino acid sequence of SEQ ID NO:98 and comprises a VL having at least 80% identity to the amino acid sequence of SEQ ID NO:99. In certain aspects, the antibody or antigen-binding fragment thereof that specifically binds to P. aeruginosa Psl and PcrV comprises a VH having at least 85% identity to the amino acid sequence of SEQ ID NO:98 and comprises a VL having at least 85% identity to the amino acid sequence of SEQ ID NO:99. In certain aspects, the antibody or antigen-binding fragment thereof that specifically binds to P. aeruginosa Psl and PcrV comprises a VH having at least 90% identity to the amino acid sequence of SEQ ID NO:98 and comprises a VL having at least 90% identity to the amino acid sequence of SEQ ID NO:99. In certain aspects, the antibody or antigen-binding fragment thereof that specifically binds to P. aeruginosa Psl and PcrV comprises a VH having at least 95% identity to the amino acid sequence of SEQ ID NO:98 and comprises a VL having at least 95% identity to the amino acid sequence of SEQ ID NO:99. In certain aspects, the antibody or antigen-binding fragment thereof that specifically binds to P. aeruginosa Psl and PcrV comprises a VH having at least 98% identity to the amino acid sequence of SEQ ID NO:98 and comprises a VL having at least 98% identity to the amino acid sequence of SEQ ID NO:99. In certain aspects, the antibody or antigen-binding fragment thereof that specifically binds to P. aeruginosa Psl and PcrV comprises a VH having at least 99% identity to the amino acid sequence of SEQ ID NO:98 and comprises a VL having at least 99% identity to the amino acid sequence of SEQ ID NO:99. In certain aspects, the antibody or antigen-binding fragment thereof that specifically binds to P. aeruginosa Psl and PcrV comprises a VH and a VL having the amino acid sequences of SEQ ID NOs:98 and 99.

In certain aspects, the antibody or antigen-binding fragment thereof that specifically binds to P. aeruginosa Psl and PcrV comprises a VH having at least 75% identity to the amino acid sequence of SEQ ID NO:79, a VH having at least 75% identity to the amino acid sequence of SEQ ID NO:81, a VL having at least 75% identity to the amino acid sequence of SEQ ID NO:72, and a VL having at least 75% identity to the amino acid sequence of SEQ ID NO:82. In certain aspects, the antibody or antigen-binding fragment thereof that specifically binds to P. aeruginosa Psl and PcrV comprises a VH having at least 80% identity to the amino acid sequence of SEQ ID NO:79, a VH having at least 80% identity to the amino acid sequence of SEQ ID NO:81, a VL having at least 80% identity to the amino acid sequence of SEQ ID NO:72, and a VL having at least 80% identity to the amino acid sequence of SEQ ID NO:82. In certain aspects, the antibody or antigen-binding fragment thereof that specifically binds to P. aeruginosa Psl and PcrV comprises a VH having at least 90% identity to the amino acid sequence of SEQ ID NO:79, a VH having at least 90% identity to the amino acid sequence of SEQ ID NO:81, a VL having at least 90% identity to the amino acid sequence of SEQ ID NO:72, and a VL having at least 90% identity to the amino acid sequence of SEQ ID NO:82. In certain aspects, the antibody or antigen-binding fragment thereof that specifically binds to P. aeruginosa Psl and PcrV comprises a VH having at least 95% identity to the amino acid sequence of SEQ ID NO:79, a VH having at least 95% identity to the amino acid sequence of SEQ ID NO:81, a VL having at least 95% identity to the amino acid sequence of SEQ ID NO:72, and a VL having at least 95% identity to the amino acid sequence of SEQ ID NO:82. In certain aspects, the antibody or antigen-binding fragment thereof that specifically binds to P. aeruginosa Psl and PcrV comprises a VH having at least 98% identity to the amino acid sequence of SEQ ID NO:79, a VH having at least 98% identity to the amino acid sequence of SEQ ID NO:81, a VL having at least 98% identity to the amino acid sequence of SEQ ID NO:72, and a VL having at least 98% identity to the amino acid sequence of SEQ ID NO:82. In certain aspects, the antibody or antigen-binding fragment thereof that specifically binds to P. aeruginosa Psl and PcrV comprises a VH having at least 99% identity to the amino acid sequence of SEQ ID NO:79, a VH having at least 99% identity to the amino acid sequence of SEQ ID NO:81, a VL having at least 99% identity to the amino acid sequence of SEQ ID NO:72, and a VL having at least 99% identity to the amino acid sequence of SEQ ID NO:82. In certain aspects, the antibody or antigen-binding fragment thereof that specifically binds to P. aeruginosa Psl and PcrV comprises a VH comprising the amino acid sequence of SEQ ID NO:79, a VH comprising the amino acid sequence of SEQ ID NO:81, a VL comprising the amino acid sequence of SEQ ID NO:72, and a VL comprising the amino acid sequence of SEQ ID NO:82.

In certain aspects, the antibody or antigen-binding fragment thereof that specifically binds to P. aeruginosa Psl and PcrV comprises a VH having at least 75% identity to the amino acid sequence of SEQ ID NO:96, a VH having at least 75% identity to the amino acid sequence of SEQ ID NO:98, a VL having at least 75% identity to the amino acid sequence of SEQ ID NO:97, and a VL having at least 75% identity to the amino acid sequence of SEQ ID NO:99. In certain aspects, the antibody or antigen-binding fragment thereof that specifically binds to P. aeruginosa Psl and PcrV comprises a VH having at least 80% identity to the amino acid sequence of SEQ ID NO:96, a VH having at least 80% identity to the amino acid sequence of SEQ ID NO:98, a VL having at least 80% identity to the amino acid sequence of SEQ ID NO:97, and a VL having at least 80% identity to the amino acid sequence of SEQ ID NO:99. In certain aspects, the antibody or antigen-binding fragment thereof that specifically binds to P. aeruginosa Psl and PcrV comprises a VH having at least 90% identity to the amino acid sequence of SEQ ID NO:96, a VH having at least 90% identity to the amino acid sequence of SEQ ID NO:98, a VL having at least 90% identity to the amino acid sequence of SEQ ID NO:97, and a VL having at least 90% identity to the amino acid sequence of SEQ ID NO:99. In certain aspects, the antibody or antigen-binding fragment thereof that specifically binds to P. aeruginosa Psl and PcrV comprises a VH having at least 95% identity to the amino acid sequence of SEQ ID NO:96, a VH having at least 95% identity to the amino acid sequence of SEQ ID NO:98, a VL having at least 95% identity to the amino acid sequence of SEQ ID NO:97, and a VL having at least 95% identity to the amino acid sequence of SEQ ID NO:99. In certain aspects, the antibody or antigen-binding fragment thereof that specifically binds to P. aeruginosa Psl and PcrV comprises a VH having at least 98% identity to the amino acid sequence of SEQ ID NO:96, a VH having at least 98% identity to the amino acid sequence of SEQ ID NO:98, a VL having at least 98% identity to the amino acid sequence of SEQ ID NO:97, and a VL having at least 98% identity to the amino acid sequence of SEQ ID NO:99. In certain aspects, the antibody or antigen-binding fragment thereof that specifically binds to P. aeruginosa Psl and PcrV comprises a VH having at least 99% identity to the amino acid sequence of SEQ ID NO:96, a VH having at least 99% identity to the amino acid sequence of SEQ ID NO:98, a VL having at least 99% identity to the amino acid sequence of SEQ ID NO:97, and a VL having at least 99% identity to the amino acid sequence of SEQ ID NO:99. In certain aspects, the antibody or antigen-binding fragment thereof that specifically binds to P. aeruginosa Psl and PcrV comprises a VH comprising the amino acid sequence of SEQ ID NO:96, a VH comprising the amino acid sequence of SEQ ID NO:98, a VL comprising the amino acid sequence of SEQ ID NO:97, and a VL comprising the amino acid sequence of SEQ ID NO:99.

In certain aspects, the antibody or antigen-binding fragment thereof that specifically binds to P. aeruginosa Psl and PcrV comprises an ScFv comprising the VH and VL sequences of the WapR-004RAD (SEQ ID NOs:79 and 72) and/or V2L2 antibody (SEQ ID NOs:81 and 82). In certain aspects, the antibody or antigen-binding fragment thereof that specifically binds to P. aeruginosa Psl and PcrV comprises an ScFv comprising the VH and VL sequences of WapR-004RAD (SEQ ID NOs:79 and 72) and V2L2 IgG. In certain aspects, the antibody or antigen-binding fragment thereof that specifically binds to P. aeruginosa Psl and PcrV comprises an ScFv comprising the VH and VL sequences of V2L2 (SEQ ID NOs:81 and 82) and WapR-004RAD IgG. In certain aspects, the antibody or antigen-binding fragment thereof that specifically binds to P. aeruginosa Psl and PcrV comprises the VH-CDR1, VH-CDR2, VH-CDR3, VL-CDR1, VL-CDR2, and VL-CDR3 sequences of WapR-004RAD (i.e., SEQ ID NOs:73, 74, 80, 76, 77, and 78, respectively). In certain aspects, the antibody or antigen-binding fragment thereof that specifically binds to P. aeruginosa Psl and PcrV comprises the VH-CDR1, VH-CDR2, VH-CDR3, VL-CDR1, VL-CDR2, and VL-CDR3 sequences of V2L2 (i.e., SEQ ID NOs:83, 84, 85, 86, 87, and 88, respectively). In certain aspects, the antibody or antigen-binding fragment thereof that specifically binds to P. aeruginosa Psl and PcrV comprises the VH-CDR1, VH-CDR2, VH-CDR3, VL-CDR1, VL-CDR2, and VL-CDR3 sequences of WapR-004RAD (i.e., SEQ ID NOs:73, 74, 80, 76, 77, and 78, respectively) and the VH-CDR1, VH-CDR2, VH-CDR3, VL-CDR1, VL-CDR2, and VL-CDR3 sequences of V2L2 (i.e., SEQ ID NOs:83, 84, 85, 86, 87, and 88, respectively). In certain aspects, the antibody or antigen-binding fragment thereof that specifically binds to P. aeruginosa Psl and PcrV comprises the amino acids of SEQ ID NO:89 (W4-RAD ScFv in Bs3), SEQ ID NO:90 (W4-RAD ScFv-V2L2 in Bs2), or SEQ ID NO:91 (W4-RAD ScFv in Bs4).

In certain aspects, the antibody or antigen-binding fragment thereof that specifically binds to P. aeruginosa Psl and PcrV comprises the amino acid sequence of SEQ ID NO:92 (the light chain of Bs4-V2L2-2C). In certain aspects, the antibody or antigen-binding fragment thereof that specifically binds to P. aeruginosa Psl and PcrV comprises the amino acid sequence of SEQ ID NO:93 (the heavy chain of Bs4-V2L2-2C). In certain aspects, the antibody or antigen-binding fragment thereof that specifically binds to P. aeruginosa Psl and PcrV comprises the amino acid sequence of SEQ ID NO:92 (the light chain of Bs4-V2L2-2C) and the amino acid sequence of SEQ ID NO:93 (the heavy chain of Bs4-V2L2-2C).

In certain aspects, the antibody or antigen-binding fragment thereof that specifically binds to P. aeruginosa Psl and PcrV is Bs2-V2L2, Bs3-V2L2, Bs4-V2L2, Bs2-V2L2-2C, Bs3-V2L2-2C, Bs4-V2L2-2C (also referred to as Bs4-WT), Bs4-V2L2-2C-YTE, or Bs2-W4-RAD-2C (as disclosed in WO 2013/070615 or WO 2014/074528, which are herein incorporated by reference in their entireties).

In certain aspects, the antibody or antigen-binding fragment thereof that specifically binds to P. aeruginosa Psl and PcrV comprises an ScFv comprising the VH and VL sequences of Ps10096 (SEQ ID NOs:96 and 97) and/or V2L2-MD (SEQ ID NOs:98 and 99). In certain aspects, the antibody or antigen-binding fragment thereof that specifically binds to P. aeruginosa Psl and PcrV comprises an ScFv comprising the VH and VL sequences of Ps10096 (SEQ ID NOs:96 and 97) and V2L2-MD IgG. In certain aspects, the antibody or antigen-binding fragment thereof that specifically binds to P. aeruginosa Psl and PcrV comprises an ScFv comprising the VH and VL sequences of V2L2-MD (SEQ ID NOs:98 and 99) and Ps10096 IgG. In certain aspects, the antibody or antigen-binding fragment thereof that specifically binds to P. aeruginosa Psl and PcrV comprises the VH-CDR1, VH-CDR2, VH-CDR3, VL-CDR1, VL-CDR2, and VL-CDR3 sequences of Ps10096 (i.e., SEQ ID NOs:73, 74, 94, 76, 77, and 95, respectively). In certain aspects, the antibody or antigen-binding fragment thereof that specifically binds to P. aeruginosa Psl and PcrV comprises the VH-CDR1, VH-CDR2, VH-CDR3, VL-CDR1, VL-CDR2, and VL-CDR3 sequences of V2L2-MD (i.e., SEQ ID NOs: 83, 84, 85, 86, 87, and 88, respectively). In certain aspects, the antibody or antigen-binding fragment thereof that specifically binds to P. aeruginosa Psl and PcrV comprises the VH-CDR1, VH-CDR2, VH-CDR3, VL-CDR1, VL-CDR2, and VL-CDR3 sequences of Ps10096 (i.e., SEQ ID NOs:73, 74, 94, 76, 77, and 95, respectively) and the VH-CDR1, VH-CDR2, VH-CDR3, VL-CDR1, VL-CDR2, and VL-CDR3 sequences of V2L2-MD (i.e., SEQ ID NOs:83, 84, 85, 86, 87, and 88, respectively).

In certain aspects, the antibody or antigen-binding fragment thereof that specifically binds to P. aeruginosa Psl and PcrV is a BS4-GLO (as described in WO 2014/074528, which is herein incorporated by reference in its entirety). In certain aspects, the antibody or antigen-binding fragment thereof that specifically binds to P. aeruginosa Psl and PcrV comprises anti-Psl scFv Ps10096 and anti-PcrV V2L2-MD VH and VL. In certain aspects, the antibody or antigen-binding fragment thereof that specifically binds to P. aeruginosa Psl and PcrV comprises an anti-PcrV ScFv and an anti-Psl VH and VL.

In certain aspects, the antibody or antigen-binding fragment thereof that specifically binds to P. aeruginosa Psl and PcrV comprises a light chain comprising the amino acid sequence of SEQ ID NO:100 and a heavy chain comprising the amino acid sequence of SEQ ID NO:101.

In certain embodiments, an antibody or antigen-binding fragment thereof as described herein specifically binds to an P. aeruginosa epitope (e.g., Psl, PcrV, or Psl and PcrV) with an affinity characterized by a dissociation constant (KD) no greater than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

In certain aspects, the antibody or antigen-binding fragment thereof that specifically binds to Pseudomonas Psl and/or PcrV, (a) inhibits attachment of Pseudomonas aeruginosa to epithelial cells, (b) promotes, mediates, or enhances opsonophagocytic killing (OPK) of P. aeruginosa, (c) inhibits attachment of P. aeruginosa to epithelial cells, and/or (d) disrupts the activity of the type III toxin secretion system.

Pharmaceutical Compositions

In certain embodiments, an anti-*Staphylococcus* and/or anti-*Pseudomonas* antibody or antigen-binding fragment provided herein can be formulated with a pharmaceutically acceptable carrier as pharmaceutical (therapeutic) compositions, and can be administered by a variety of methods known in the art. The route and/or mode of administration may vary depending upon the desired results. As used herein, the pharmaceutical formulations comprising an anti-*Staphylococcus* and/or anti-*Pseudomonas* antibody or antigen-binding fragment are referred to as formulations of the technology. The term "pharmaceutically acceptable carrier" means one or more non-toxic materials that do not interfere with the effectiveness of the biological activity of the active ingredients. Such preparations routinely contain salts, buffering agents, preservatives, compatible carriers, and optionally other therapeutic agents. Such pharmaceutically acceptable preparations also routinely contain compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being comingled with the antibodies and antigen-binding fragments thereof of the present technology, and with each other, in a manner such that there is no interaction which would substantially impair the desired pharmaceutical efficacy.

Therapeutic compositions of the present technology can be formulated for a particular dosage. Dosage regimens can be adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Therapeutic compositions of the present technology can be formulated for particular routes of administration, such as oral, nasal, pulmonary, topical (including buccal and sublingual), rectal, vaginal, and/or parenteral administration. The formulations can conveniently be presented in unit dosage form and can be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect.

Treatment and Prevention Methods

As provided herein, polybacterial infections can be treated or prevented by administering an antibody or an antigen-binding fragment thereof that binds to an epitope of at least one bacterium in the polybacterial infection.

Accordingly, certain aspects are directed to methods of treating or preventing a polybacterial infection in a patient in need thereof comprising administering to the patient, an antibody or antigen-binding fragment thereof that specifically binds to a *Staphylococcus aureus* antigen, wherein the polybacterial infection comprises *S. aureus* and at least one other bacterium. One embodiment is directed to a method of treating or preventing a polybacterial infection in a patient in need thereof comprising administering to the patient, an antibody or antigen-binding fragment thereof that specifically binds to a *Staphylococcus aureus* antigen, wherein the polybacterial infection comprises *S. aureus* and at least one other bacterium, wherein the *S. aureus* potentiates the growth of the at least one other bacterium. In one embodiment, *S. aureus* alpha toxin potentiates the growth of the at least one other bacterium. Administration of the anti-*S. aureus* antibody or antigen-binding fragment thereof (e.g., an anti-alpha toxin antibody or antigen-binding fragment thereof) can inhibit the growth of at least one other bacterium. Administration of the anti-*S. aureus* antibody or antigen-binding fragment thereof (e.g., an anti-alpha toxin antibody or antigen-binding fragment thereof) can increase survival. Administration of the anti-*S. aureus* antibody or antigen-binding fragment thereof (e.g., an anti-alpha toxin antibody or antigen-binding fragment thereof) can decrease mortality.

One embodiment is directed to a method of treating or preventing a polybacterial infection in a patient in need thereof comprising administering to the patient, an antibody or antigen-binding fragment thereof that specifically binds to a *Staphylococcus aureus* antigen, wherein the polybacterial infection comprises *S. aureus* and *Pseudomonas* (e.g., *P. aeruginosa*). One embodiment is directed to a method of treating or preventing a polybacterial infection in a patient in need thereof comprising administering to the patient, an antibody or antigen-binding fragment thereof that specifically binds to a *Staphylococcus aureus* antigen, wherein the polybacterial infection comprises *S. aureus* and *Pseudomonas* (e.g., *P. aeruginosa*), wherein the *S. aureus* potentiates the growth of the *Pseudomonas* (e.g., *P. aeruginosa*). In one embodiment, *S. aureus* alpha toxin potentiates the growth of the *Pseudomonas* (e.g., *P. aeruginosa*). Administration of the anti-*S. aureus* antibody or antigen-binding fragment thereof (e.g., an anti-alpha toxin antibody or antigen-binding fragment thereof) can inhibit the growth of the *Pseudomonas* (e.g., *P. aeruginosa*). Administration of the anti-*S. aureus* antibody or antigen-binding fragment thereof (e.g., an anti-alpha toxin antibody or antigen-binding fragment thereof) can increase survival. Administration of the anti-*S. aureus* antibody or antigen-binding fragment thereof (e.g., an anti-alpha toxin antibody or antigen-binding fragment thereof) can decrease mortality.

Certain aspects are directed to methods of treating or preventing a polybacterial infection in a patient in need thereof comprising administering to the patient, an antibody or antigen-binding fragment thereof that specifically binds to a *Pseudomonas aeruginosa* antigen, wherein the polybacterial infection comprises *P. aeruginosa* and at least one other bacterium. One embodiment is directed to a method of treating or preventing a polybacterial infection in a patient in need thereof comprising administering to the patient, an antibody or antigen-binding fragment thereof that specifically binds to a *P. aeruginosa* antigen, wherein the polybacterial infection comprises *P. aeruginosa* and at least one other bacterium, wherein the *P. aeruginosa* potentiates the growth of the at least one other bacterium. Administration of the anti-*P. aeruginosa* antibody or antigen-binding fragment (e.g., an antibody or antigen-binding fragment thereof that binds to Psl, PcrV, or Psl and PcrV) thereof can inhibit the growth of at least one other bacterium. Administration of the anti-*P. aeruginosa* antibody or antigen-binding fragment (e.g., an antibody or antigen-binding fragment thereof that binds to Psl, PcrV, or Psl and PcrV) thereof can increase survival. Administration of the anti-*P. aeruginosa* antibody or antigen-binding fragment (e.g., an antibody or antigen-binding fragment thereof that binds to Psl, PcrV, or Psl and PcrV) thereof can decrease mortatlity.

One embodiment is directed to a method of treating or preventing a polybacterial infection in a patient in need thereof comprising administering to the patient, an antibody or antigen-binding fragment thereof that specifically binds to a *P. aeruginosa* antigen, wherein the polybacterial infection comprises *P. aeruginosa* and *Staphylococcus* (e.g., *S. aureus*). One embodiment is directed to a method of treating or preventing a polybacterial infection in a patient in need thereof comprising administering to the patient, an antibody or antigen-binding fragment thereof that specifically binds to a *P. aeruginosa* antigen, wherein the polybacterial infection comprises *P. aeruginosa* and *Staphylococcus* (e.g., *S. aureus*), wherein the *P. aeruginosa* potentiates the growth of the *Staphylococcus* (e.g., *S. aureus*). Administration of the anti-*P. aeruginosa* antibody or antigen-binding fragment thereof (e.g., an antibody or antigen-binding fragment thereof that binds to Psl, PcrV, or Psl and PcrV) can inhibit the growth of the *Staphylococcus* (e.g., *S. aureus*). Administration of the anti-*P. aeruginosa* antibody or antigen-binding fragment thereof (e.g., an antibody or antigen-binding fragment thereof that binds to Psl, PcrV, or Psl and PcrV) can increase survival. Administration of the anti-*P. aeruginosa* antibody or antigen-binding fragment thereof (e.g., an antibody or antigen-binding fragment thereof that binds to Psl, PcrV, or Psl and PcrV) can decrease mortality.

Certain aspects are directed to methods of inhibiting the growth of *Pseudomonas* (e.g., *P. aeruginosa*) in a patient comprising administering an antibody or antigen-binding fragment thereof to a patient in need thereof, wherein the antibody or antigen-binding fragment thereof specifically binds to a *Staphylococcus aureus* antigen (e.g., alpha toxin). In certain aspects, the antibody or antigen-binding fragment thereof specifically binds to a *Staphylococcus aureus* antigen (e.g., alpha toxin) inhibits the growth of *Pseudomonas* (e.g., *P. aeruginosa*) by 25%. In certain aspects, the antibody or antigen-binding fragment thereof specifically binds to a *Staphylococcus aureus* antigen (e.g., alpha toxin) inhibits the growth of *Pseudomonas* (e.g., *P. aeruginosa*) by 50%. In certain aspects, the antibody or antigen-binding fragment thereof specifically binds to a *Staphylococcus aureus* antigen (e.g., alpha toxin) inhibits the growth of *Pseudomonas* (e.g., *P. aeruginosa*) by 75%. In certain aspects, the antibody or antigen-binding fragment thereof specifically binds to a *Staphylococcus aureus* antigen (e.g., alpha toxin) inhibits the growth of *Pseudomonas* (e.g., *P. aeruginosa*) by 80%. In certain aspects, the antibody or antigen-binding fragment thereof specifically binds to a *Staphylococcus aureus* antigen (e.g., alpha toxin) inhibits the growth of *Pseudomonas* (e.g., *P. aeruginosa*) by 85%. In certain aspects, the antibody or antigen-binding fragment thereof specifically binds to a *Staphylococcus aureus* antigen (e.g., alpha toxin) inhibits the growth of *Pseudomonas* (e.g., *P. aeruginosa*) by 90%.

The number of colony forming units (CFU) in a samples obtained from a patient with a polybacterial infection can provide an indication of the severity of the infection. In certain aspects, administration of an antibody or antigen-binding fragment thereof specifically binds to a *Staphylococcus aureus* antigen (e.g., alpha toxin) decreases *Pseudomonas* (e.g., *P. aeruginosa*) CFU in a sample obtained from a patient by at least 50%. In certain aspects, administration of an antibody or antigen-binding fragment thereof specifically binds to a *Staphylococcus aureus* antigen (e.g., alpha toxin) decreases *Pseudomonas* (e.g., *P. aeruginosa*) CFU in a sample obtained from a patient by at least 75%. In certain aspects, administration of an antibody or antigen-binding fragment thereof specifically binds to a *Staphylococcus aureus* antigen (e.g., alpha toxin) decreases *Pseudomonas* (e.g., *P. aeruginosa*) CFU in a sample obtained from a patient by at least 80%. In certain aspects, administration of an antibody or antigen-binding fragment thereof specifically binds to a *Staphylococcus aureus* antigen (e.g., alpha toxin) decreases *Pseudomonas* (e.g., *P. aeruginosa*) CFU in a sample obtained from a patient by at least 85%. In certain aspects, administration of an antibody or antigen-binding fragment thereof specifically binds to a *Staphylococcus aureus* antigen (e.g., alpha toxin) decreases *Pseudomonas* (e.g., *P. aeruginosa*) CFU in a sample obtained from a patient by at least 90%. In certain aspects, administration of an antibody or antigen-binding fragment thereof specifically binds to a *Staphylococcus aureus* antigen (e.g., alpha toxin) decreases *Pseudomonas* (e.g., *P. aeruginosa*) CFU in a sample obtained from a patient by at least 95%. In certain aspects, administration of an antibody or antigen-binding fragment thereof specifically binds to a *Staphylococcus aureus* antigen (e.g., alpha toxin) decreases *Pseudomonas* (e.g., *P. aeruginosa*) CFU in a sample obtained from a patient by at least 96%. In certain aspects, administration of an antibody or antigen-binding fragment thereof specifically binds to a *Staphylococcus aureus* antigen (e.g., alpha toxin) decreases *Pseudomonas* (e.g., *P. aeruginosa*) CFU in a sample obtained from a patient by at least 97%. In certain aspects, administration of an antibody or antigen-binding fragment thereof specifically binds to a *Staphylococcus aureus* antigen (e.g., alpha toxin) decreases *Pseudomonas* (e.g., *P. aeruginosa*) CFU in a sample obtained from a patient by at least 98%. In certain aspects, administration of an antibody or antigen-binding fragment thereof specifically binds to a *Staphylococcus aureus* antigen (e.g., alpha toxin) decreases *Pseudomonas* (e.g., *P. aeruginosa*) CFU in a sample obtained from a patient by at least 99%. In certain aspects, administration of an antibody or antigen-binding fragment thereof specifically binds to a *Staphylococcus aureus* antigen (e.g., alpha toxin) eliminates *Pseudomonas* (e.g., *P. aeruginosa*) CFU in a sample obtained from a patient.

Certain aspects are directed to methods of inhibiting the growth of *Staphylococcus* (e.g., *S. aureus*) in a patient comprising administering an antibody or antigen-binding fragment thereof to a patient in need thereof, wherein the antibody or antigen-binding fragment thereof specifically binds to a *Pseudomonas aeruginosa* antigen (e.g., Pcs1, PcrV, or Psl and PcrV). In certain aspects, the antibody or antigen-binding fragment thereof specifically binds to a *Pseudomonas aeruginosa* antigen (e.g., Pcs1, PcrV, or Psl and PcrV) inhibits growth of *Staphylococcus* (e.g., *S. aureus*) by 25%. In certain aspects, the antibody or antigen-binding fragment thereof specifically binds to a *Pseudomonas aeruginosa* antigen (e.g., Pcs1, PcrV, or Psl and PcrV) inhibits growth of *Staphylococcus* (e.g., *S. aureus*) by 50%. In certain aspects, the antibody or antigen-binding fragment thereof specifically binds to a *Pseudomonas aeruginosa* antigen (e.g., Pcs1, PcrV, or Psl and PcrV) inhibits growth of *Staphylococcus* (e.g., *S. aureus*) by 75%. In certain aspects, the antibody or antigen-binding fragment thereof specifically binds to a *Pseudomonas aeruginosa* antigen (e.g., Pcs1, PcrV, or Psl and PcrV) inhibits growth of *Staphylococcus* (e.g., *S. aureus*) by 80%. In certain aspects, the antibody or antigen-binding fragment thereof specifically binds to a *Pseudomonas aeruginosa* antigen (e.g., Pcs1, PcrV, or Psl and PcrV) inhibits growth of *Staphylococcus* (e.g., *S. aureus*) by 85%. In certain aspects, the antibody or antigen-binding fragment thereof specifically binds to a

*Pseudomonas aeruginosa* antigen (e.g., Pcs1, PcrV, or Psl and PcrV) inhibits growth of *Staphylococcus* (e.g., *S. aureus*) by 90%.

In certain aspects, administration of an antibody or antigen-binding fragment thereof specifically binds to a *Pseudomonas aeruginosa* antigen (e.g., Pcs1, PcrV, or Psl and PcrV) decreases *Staphylococcus* (e.g., *S. aureus*) CFU in a sample obtained from a patient by at least 50%. In certain aspects, administration of an antibody or antigen-binding fragment thereof specifically binds to a *Pseudomonas aeruginosa* antigen (e.g., Pcs1, PcrV, or Psl and PcrV) decreases *Staphylococcus* (e.g., *S. aureus*) CFU in a sample obtained from a patient by at least 75%. In certain aspects, administration of an antibody or antigen-binding fragment thereof specifically binds to a *Pseudomonas aeruginosa* antigen (e.g., Pcs1, PcrV, or Psl and PcrV) decreases *Staphylococcus* (e.g., *S. aureus*) CFU in a sample obtained from a patient by at least 80%. In certain aspects, administration of an antibody or antigen-binding fragment thereof specifically binds to a *Pseudomonas aeruginosa* antigen (e.g., Pcs1, PcrV, or Psl and PcrV) decreases *Staphylococcus* (e.g., *S. aureus*) CFU in a sample obtained from a patient by at least 85%. In certain aspects, administration of an antibody or antigen-binding fragment thereof specifically binds to a *Pseudomonas aeruginosa* antigen (e.g., Pcs1, PcrV, or Psl and PcrV) decreases *Staphylococcus* (e.g., *S. aureus*) CFU in a sample obtained from a patient by at least 90%. In certain aspects, administration of an antibody or antigen-binding fragment thereof specifically binds to a *Pseudomonas aeruginosa* antigen (e.g., Pcs1, PcrV, or Psl and PcrV) decreases *Staphylococcus* (e.g., *S. aureus*) CFU in a sample obtained from a patient by at least 95%. In certain aspects, administration of an antibody or antigen-binding fragment thereof specifically binds to a *Pseudomonas aeruginosa* antigen (e.g., Pcs1, PcrV, or Psl and PcrV) decreases *Staphylococcus* (e.g., *S. aureus*) CFU in a sample obtained from a patient by at least 96%. In certain aspects, administration of an antibody or antigen-binding fragment thereof specifically binds to a *Pseudomonas aeruginosa* antigen (e.g., Pcs1, PcrV, or Psl and PcrV) decreases *Staphylococcus* (e.g., *S. aureus*) CFU in a sample obtained from a patient by at least 97%. In certain aspects, administration of an antibody or antigen-binding fragment thereof specifically binds to a *Pseudomonas aeruginosa* antigen (e.g., Pcs1, PcrV, or Psl and PcrV) decreases *Staphylococcus* (e.g., *S. aureus*) CFU in a sample obtained from a patient by at least 98%. In certain aspects, administration of an antibody or antigen-binding fragment thereof specifically binds to a *Pseudomonas aeruginosa* antigen (e.g., Pcs1, PcrV, or Psl and PcrV) decreases *Staphylococcus* (e.g., *S. aureus*) CFU in a sample obtained from a patient by at least 99%. In certain aspects, administration of an antibody or antigen-binding fragment thereof specifically binds to a *Pseudomonas aeruginosa* antigen (e.g., Pcs1, PcrV, or Psl and PcrV) eliminates *Staphylococcus* (e.g., *S. aureus*) CFU in a sample obtained from a patient.

In certain aspects, the polybacterial infection is an ocular infection, a lung infection, a burn infection, a wound infection, a surgical wound infection, a skin infection, a soft tissue infection, a blood infection, a bone infection, or a combination of two or more of said infections.

In certain aspects, the patient suffers from acute pneumonia, burn injury, corneal infection, cystic fibrosis, ventilator-associated pneumonia, a skin infection, a wound infection, or a combination thereof.

Methods of preparing and administering anti-bacterial antibodies or antigen-binding fragments thereof (e.g. anti-*Staphylococcus*, anti-*S. aureus*, anti-alpha toxin, anti-*Pseudomonas*, anti-*P. aeruginosa*, anti-Psl, anti-PcrV, or anti-Psl and PcrV antibodies, or antigen-binding fragments thereof) are well known to or are readily determined by those skilled in the art. The route of administration of the anti-bacterial antibodies or antigen-binding fragments thereof can be, for example, oral, parenteral, by inhalation or topical. The term parenteral as used herein includes, e.g., intravenous, intraarterial, intraperitoneal, intramuscular, or subcutaneous administration. A suitable form for administration would be a solution for injection, in particular for intravenous or intraarterial injection or drip. However, in other methods compatible with the teachings herein, anti-bacterial antibodies or antigen-binding fragments thereof can be delivered directly to the site of the adverse cellular population e.g., infection thereby increasing the exposure of the diseased tissue to the therapeutic agent. For example, anti-bacterial antibodies or antigen-binding fragment thereof can be directly administered to ocular tissue, burn injury, or lung tissue.

Anti-bacterial antibodies or antigen-binding fragments thereof (e.g. anti-*Staphylococcus*, anti-*S. aureus*, anti-alpha toxin, anti-*Pseudomonas*, anti-*P. aeruginosa*, anti-Psl, anti-PcrV, or anti-Psl and PcrV antibodies, or antigen-binding fragments thereof) can be administered in a pharmaceutically effective amount for the in vivo treatment of polybacterial infections (e.g., infections comprising *Staphylococcus* and/or *Pseudomonas* bacteria). In this regard, it will be appreciated that the antibodies or antigen-binding fragments thereof are formulated so as to facilitate administration and promote stability of the active agent.

In certain embodiments, anti-bacterial antibodies or antigen-binding fragments thereof (e.g. anti-*Staphylococcus*, anti-*S. aureus*, anti-alpha toxin, anti-*Pseudomonas*, anti-*P. aeruginosa*, anti-Psl, anti-PcrV, or anti-Psl and PcrV antibodies or antigen-binding fragments thereof) can be used in combination with other anti-bacterial agents such as antibiotics. Antibiotics include, for example, beta-lactam antibiotics (such as cephalexin), sulfa drugs (like co-trimoxazole/trimethoprim-sulfamethoxazole), tetracyclines (like doxycycline and minocycline), clindamycin, vancomycin, linezolid, daptomycin, teicoplanin, quinupristin/dalfopristin (synercid), tigecycline, ciprofloxacin, meropenem, tobramycin, and aztreonam. In certain embodiments, the antibiotic is ciprofloxacin.

EXAMPLES

Example 1: *Staphylococcus aureus* Potentiates Infection with *Pseudomonas aeruginosa*

Mice were inoculated with either *Pseudomonas aeruginosa* strain 6077 or *Staphylococcus aureus* strain SF8300 and their survival was assessed. Mice (n=10) were briefly anesthetized in 3% isoflurane/$O_2$, and 50 µl of bacteria (at various concentrations) was deposited on the tip of the nares. Mortality was monitored for seven days. As shown in FIG. 1A, all mice treated with 7.5e4 colony forming units (CFU) of *P. aeruginosa* survived over the seven day period, but no mice treated with 8.00e5 CFU survived. In addition, all mice treated with 1.25e8 CFU *S. aureus* survived over the seven day period, but no mice treated with either 2.25e8 or 3.25e8 CFU *S. aureus* survived (FIG. 1B).

Figure 2:
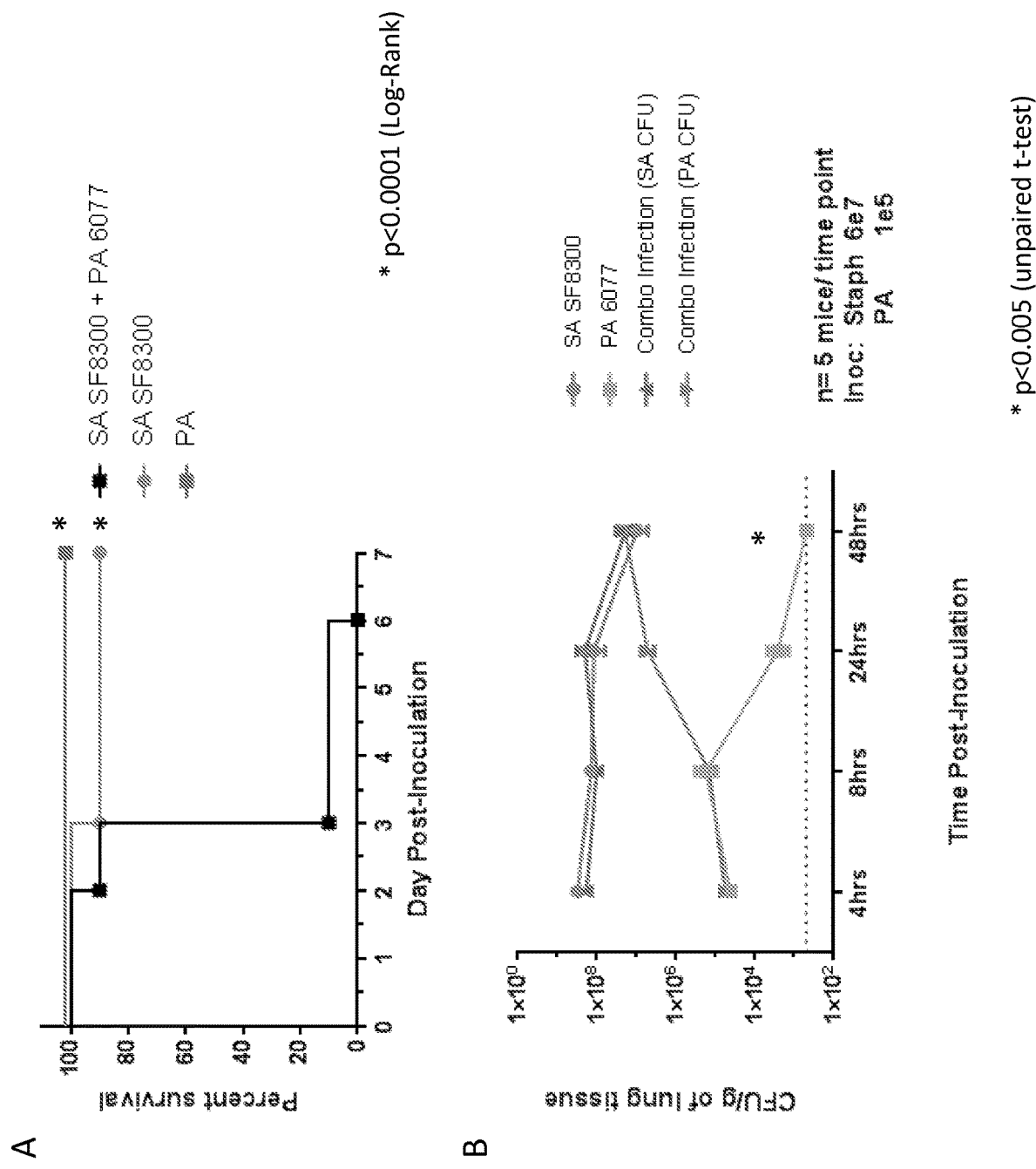
FIG. 2A shows the survival of mice inoculated with *P. aeruginosa* ("PA 6077"), *S. aureus* ("SA SF8300") ("Combo Infection").
FIG. 2B shows the colony forming units (CFU) of *P. aeruginosa* ("PA CFU") and *S. aureus* ("SA CFU") from the lungs of mice inoculated with *P. aeruginosa* and/or *S. aureus*.

In order to investigate, co-infection kinetics, mice were inoculated with a mixture of *P. aeruginosa* and *S. aureus* at a final concentration of 5.5e7 CFU per mouse of *S. aureus* and 1.1e5 CFU per mouse of *P. aeruginosa*. Mortality was monitored for seven days. As shown in FIG. 1, these doses were well below the lethal doses when administered individually. Therefore, the majority of the mice treated with either P. aeruginosa or S. aureus survived (FIG. 2A). However, none of the mice treated with the combination survived (FIG. 2A).

Figure 3:
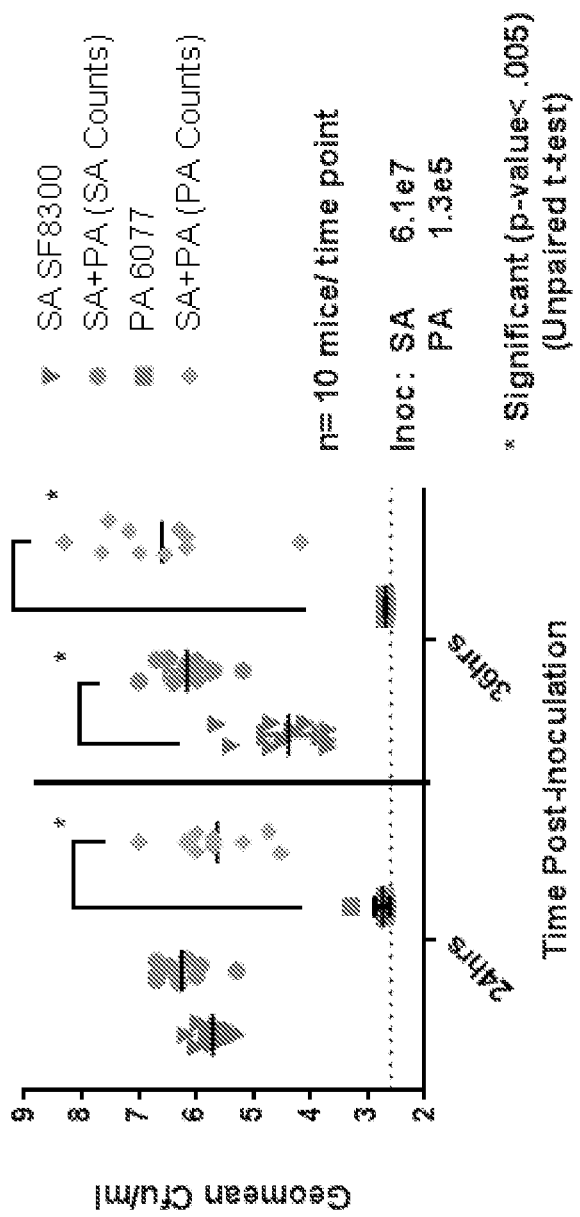
FIG. 3 shows the CFU of *P. aeruginosa* ("PA Counts") and *S. aureus* ("SA Counts") measured in mice inoculated with *P. aeruginosa* ("PA"), *S. aureus* ("SA"), or both (SA+PA).
Figure 4:
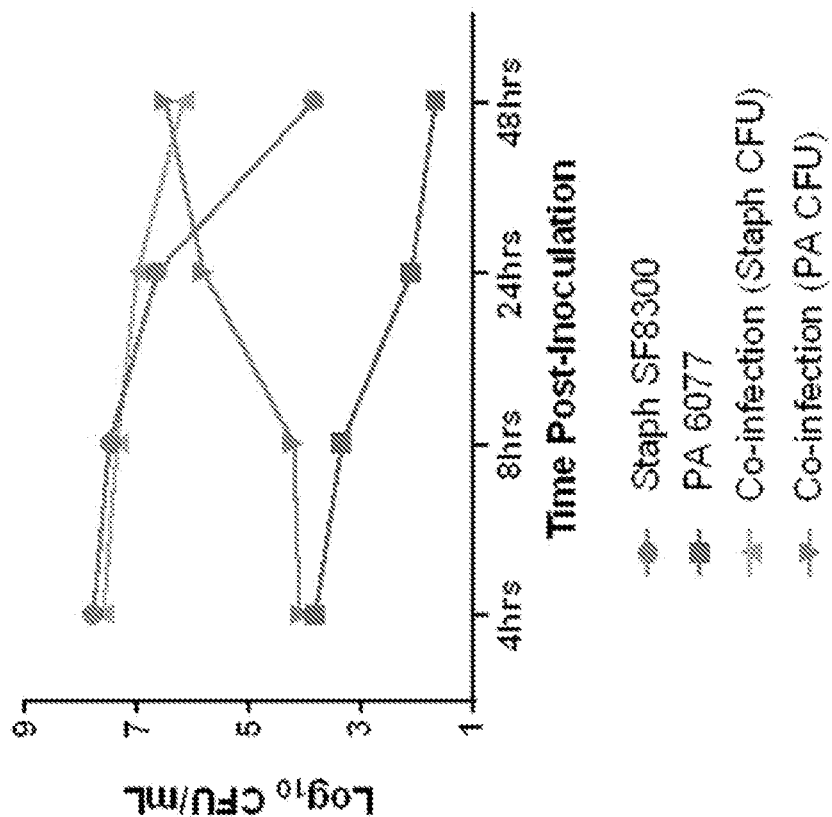
FIG. 4 shows the CFU per mL of lung homogenate in inoculated mice. Mice were inoculated with wild-type *S. aureus* ("SA SF8300 WT") alone (circles) or in combination with *P. aeruginosa* ("PA 6077") (triangles), where levels of *S. aureus* were measured at 4, 8, 24 and 48 hours post-inoculation. Mice were also inoculated with *P. aeruginosa* ("PA 6077") alone (squares) or in combination with wild-type *S. aureus* ("SA SF8300 WT"), where levels of *P. aeruginosa* ("PA") were measured at 4, 8, 24 and 48 hours post-inoculation.

P. aeruginosa and S. aureus colonization in the mice was also examined. In these experiments, mice were inoculated with a combination of P. aeruginosa and S. aureus as described above, and five mice/group were euthanized at various times. Their lungs were removed, and following homogenization in 1 mL phosphate buffered saline (PBS), aliquots were plated on mannitol-salt agar in order to quantitate S. aureus or on pseudomonoas isolation agar in order to quantitate P. aeruginosa. Levels of P. aeruginosa were significantly higher in mice inoculated with both P. aeruginosa and S. aureus than in mice inoculated with only P. aeruginosa (FIG. 2B). In addition, levels of P. aeruginosa were significantly higher in mice inoculated with both P. aeruginosa and S. aureus than in mice inoculated with only P. aeruginosa at both 24 hours and 36 hours post-inoculation (FIG. 3). In an additional experiment, colonization in mice inoculated with 6.1e7 CFU S. aureus and/or 1.3e5 CFU P. aeruginosa was also examined. In these experiments, levels of S. aureus were significantly higher in mice inoculated with both P. aeruginosa and S. aureus than in mice inoculated with only S. aureus 48 hours post-inoculation (FIG. 4).

These data demonstrate that S. aureus potentiates growth of P. aeruginosa. Furthermore, these data also demonstrate that S. aureus and P. aeruginosa combination of normally sub-lethal challenge doses increase lethality in a lung infection model. A summary of titration of P. aeruginosa and S. aureus challenge doses in a lung co-infection model is shown below where the intranasal challenge involved the P. aeruginosa strain: 6077 (exoU): LD100=~1e6 and the S. aureus strain: SF8300 (cMRSA): LD100=~2e8.

| P. aeruginosa challenge (CFU/mouse) | S. aureus challenge (CFU/mouse) | Survival (7 days) |
|---|---|---|
| 1e5 | 0 | 100% |
| 0 | 5e7 | 80-100% |
| 1e5 | 5e7 | 0-10% |
| 1e5 | 2.5e7 | 40% |
| 1e4 | 5e7 | 100% |
| 1e3 | 5e7 | 100% |
| 1e2 | 5e7 | 100% |

Example 2: S. aureus Alpha Toxin Potentiates Infection with P. aeruginosa

In order to determine if S. aureus alpha toxin was necessary for S. aureus to potentiate P. aeruginosa growth, experiments were conducted with an S. aureus strain containing a deletion in the gene encoding for alpha toxin (also known as alpha-hemolysin (hla)). In these experiments, mice were inoculated with either wild-type (WT) or mutant (Δhla) S. aureus alone (single infection) or in combination with P. aeruginosa (mixed infection). Levels of S. aureus and P. aeruginosa were then measured at 24 hours and 36 hours after inoculation. S. aureus levels were lower in mice receiving inoculations with S. aureus lacking alpha toxin (Δhla) than with wild-type S. aureus. In addition, P. aeruginosa levels were lower in mice receiving inoculations with S. aureus lacking alpha toxin (Δhla) than with wild-type S. aureus.

Figure 5:
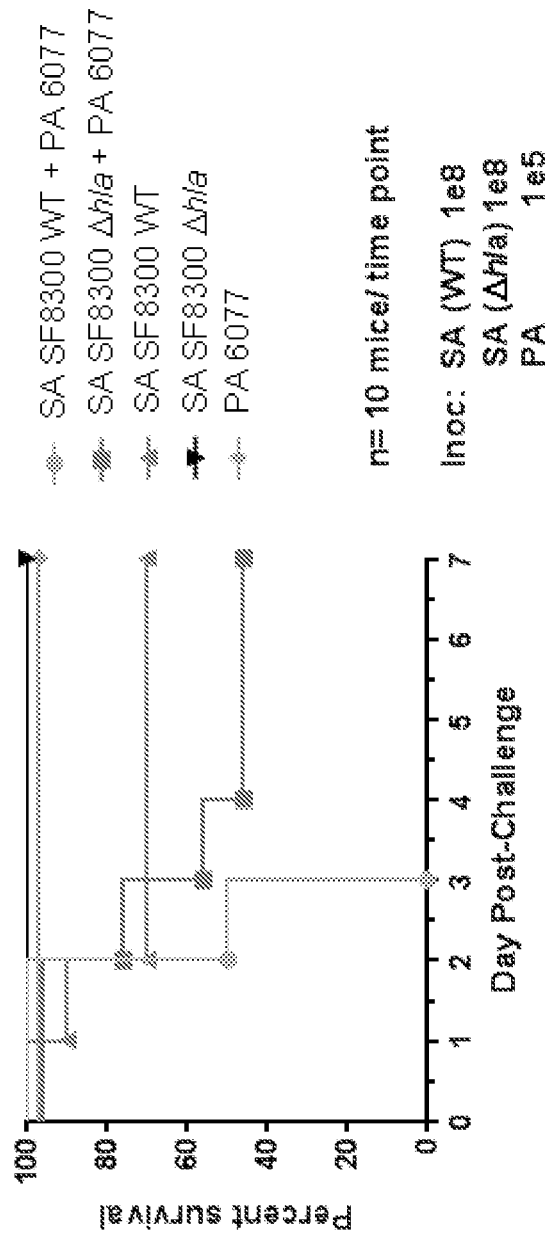
FIG. 5 shows the survival of mice inoculated with wild-type *S. aureus* ("SA SF8300 WT"), *S. aureus* containing a deletion in the gene encoding for alpha toxin ("SA SF8300 Δhla"), *P. aeruginosa* ("PA 6077"), or a combination thereof.

The effect of S. aureus alpha toxin on the survival of mice was also evaluated. Mice were inoculated with 1e8 CFU wild-type S. aureus, 1e8 CFU S. aureus lacking alpha toxin, 1e5 CFU P. aeruginosa, or a combination thereof. As shown in FIG. 5, none of the mice that received both wild-type S. aureus and P. aeruginosa survived. On the other hand all of the mice that received either P. aeruginosa or S. aureus lacking alpha toxin survived (FIG. 5). Notably, a greater number of mice that received S. aureus lacking alpha toxin in combination with P. aeruginosa survived than mice that received wild-type S. aureus in combination with P. aeruginosa (FIG. 5).

Figure 6:
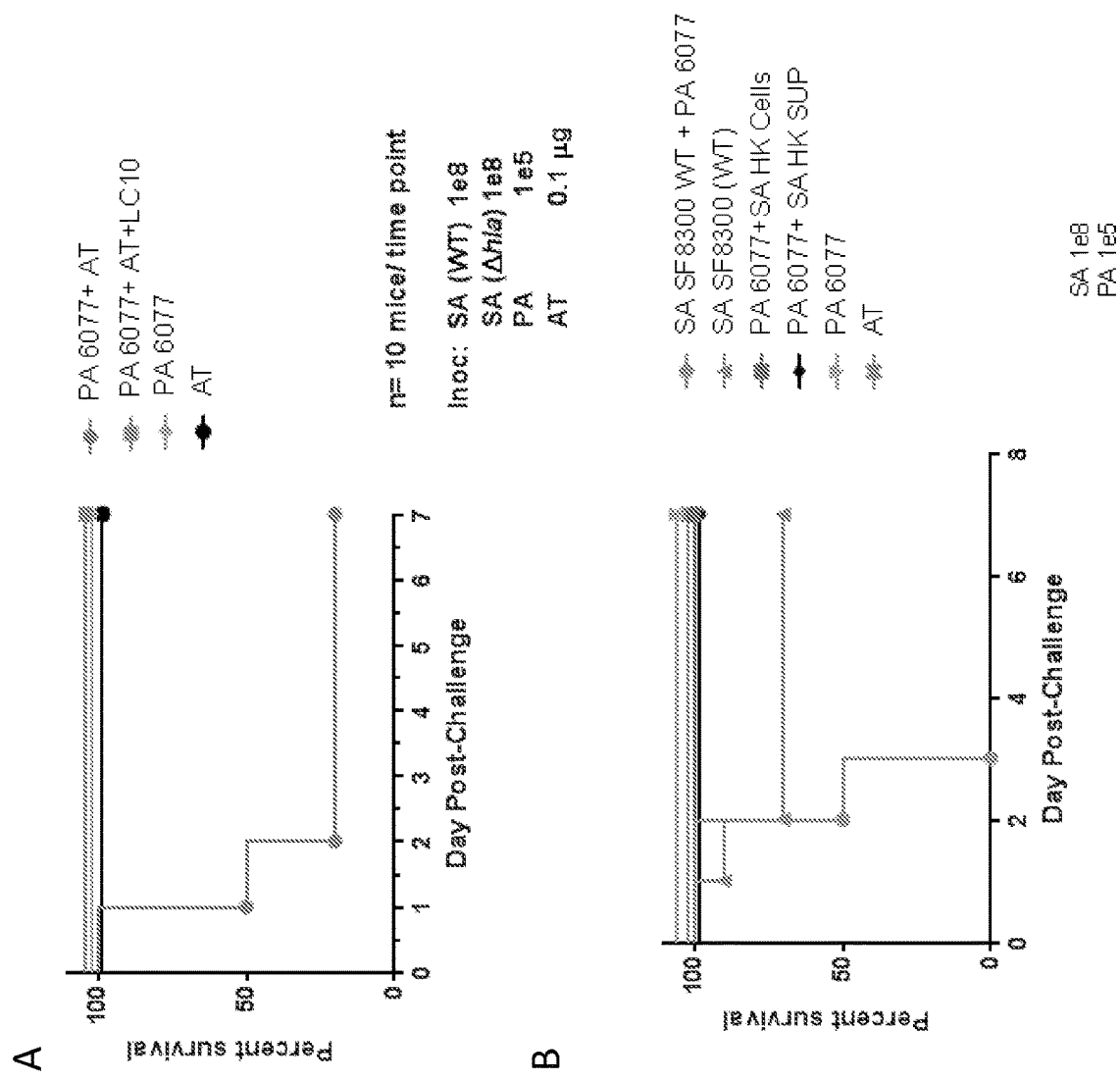
FIG. 6A shows the survival of mice that received *S. aureus* alpha toxin ("AT"), *P. aeruginosa* ("PA 6077"), *P. aeruginosa* in combination with alpha toxin, or *P. aeruginosa* in combination with alpha toxin and an anti-alpha toxin antibody (LC10).
FIG. 6B also shows the survival of mice that received *S. aureus* alpha toxin ("AT"), and *P. aeruginosa* ("PA 6077"), and also shows the survival of mice that received wild-type *S. aureus* ("SA SF8300 WT"), wild-type *S. aureus* ("SA SF8300 WT") in combination with *P. aeruginosa* ("PA 6077"), or *P. aeruginosa* ("PA 6077") with a cell pellet obtained from heat-killed *S. aureus* ("SA HK Cells") or supernatant obtained from heat-killed *S. aureus* ("SA HK SUP").

In order to determine if S. aureus alpha toxin is sufficient to potentiate the growth of P. aeruginosa, mice were inoculated with 1e5 CFU P. aeruginosa, 0.1 μg alpha toxin, or a combination thereof. Those mice inoculated with only P. aeruginosa or alpha toxin survived, but many mice inoculated with the combination did not (FIG. 6A). Thus, native alpha toxin enhances mortality when combined with P. aeruginosa. Administration of an anti-alpha toxin antibody, LC10, 24 hours prior to the inoculation was sufficient to reverse this effect. Mice receiving the combination of P. aeruginosa and alpha toxin after receiving LC10 survived (FIG. 6A).

Additional experiments demonstrated that heat-killed S. aureus were not able to potentiate growth of P. aeruginosa. Mice inoculated with 1e5 CFU P. aeruginosa in combination with either the cell pellet or supernatant obtained from heat-killed S. aureus survived (FIG. 6B).

Figure 7:
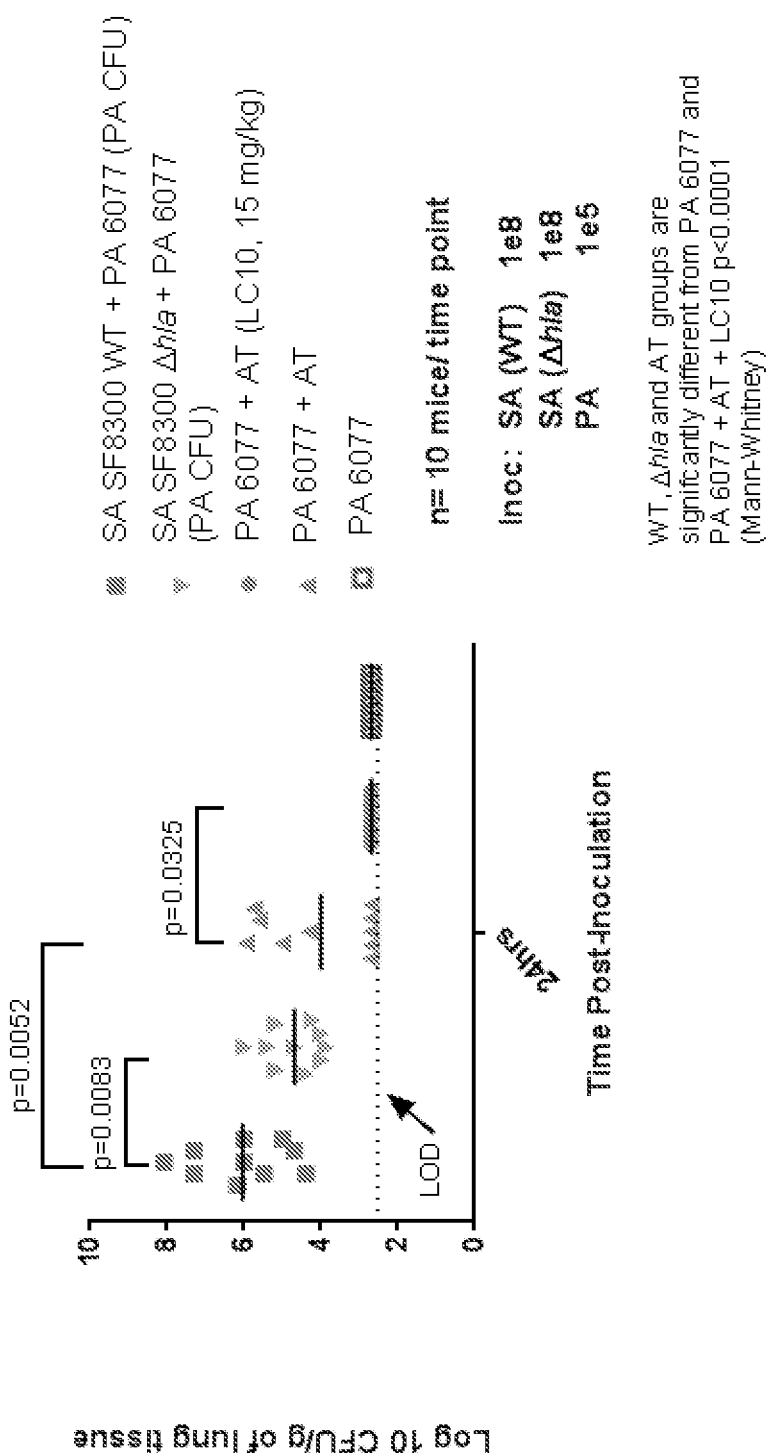
FIG. 7 shows the level of *P. aeruginosa* in mice treated with *P. aeruginosa* ("PA 6077") alone or in combination with wild-type *S. aureus* ("SA SF8300 WT), *S. aureus* containing a deletion in the gene encoding for alpha toxin ("SA SF8300 Δhla"), alpha toxin (AT), or both alpha toxin and the anti-alpha toxin antibody LC10.

Analysis of P. aeruginosa levels in treated mice revealed similar results. In particular, mice inoculated with 1e5 CFU P. aeruginosa alone showed low levels of P. aeruginosa growth (FIG. 7). However, co-inoculating with any of 1e8 CFU S. aureus, 1e8 CFU S. aureus lacking alpha toxin, or 0.1 mg alpha toxin increased P. aeruginosa (FIG. 7). Administration of 15 mg/kg of LC10 along with the 0.1 mg alpha toxin prevented the increase in P. aeruginosa (FIG. 7).

These data indicate that the alpha toxin of S. aureus is important for the ability of S. aureus to potentiate growth of P. aeruginosa and is sufficient to potentiate growth of P. aeruginosa. Moreover, an anti-S. aureus alpha toxin antibody suppresses the alpha toxin-medicated P. aeruginosa growth.

Figure 8:
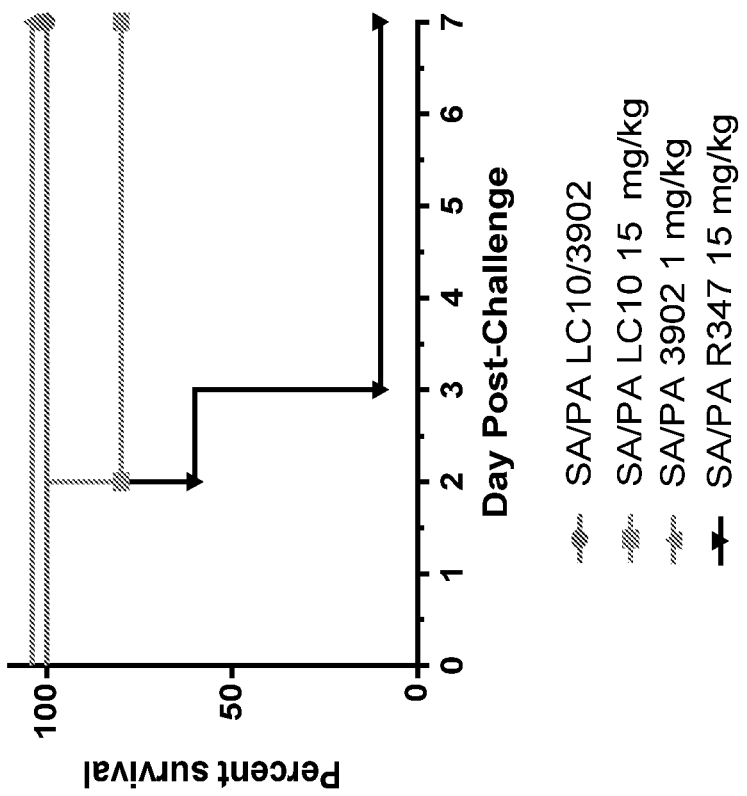
FIG. 8 shows the survival of mice that received either a control antibody ("R347"), an anti-*S. aureus* alpha toxin antibody ("LC10"), an anti-*P. aeruginosa* antibody ("3902"), or a combination of an anti-*S. aureus* alpha toxin antibody ("LC10") and an anti-*P. aeruginosa* antibody ("3902"), and were then inoculated with *S. aureus* ("SA") and *P. aeruginosa* ("PA").

Example 3: The Combination of Anti-Alpha Toxin and Anti-P. aeruginosa Antibodies Promotes Survival in a S. aureus and P. aeruginosa Polymicrobial Infection Model In order to determine if antibodies could increase survival of mice co-inoculated with P. aeruginosa and S. aureus, mice were given 15 mg/kg LC10 (an anti-S. aureus alpha toxin antibody) in combination with 1 mg/kg MEDI3902 (a bispecific antibody that binds to P. aeruginosa Psl and PcrV), or 15 mg/kg isotype control antibody (R347). The antibodies were administered 24 hours prior to inoculation with 1e5 CFU P. aeruginosa and/or 1e8 CFU S. aureus. Mice inoculated with only S. aureus or P. aeruginosa survived (FIG. 8). However, mice inoculated with both S. aureus and P. aeruginosa did not survive when they received the control antibody (FIG. 8). Administration of the LC10 and MEDI3902 antibodies was able to rescue mice receiving both S. aureus and P. aeruginosa (FIG. 8).

Similar experiments were performed in which the amounts of S. aureus and P. aeruginosa in the inoculations were varied. The inoculations contained 5e7 CFU S. aureus and 1.1e5 CFU P. aeruginosa. The combination of LC10 and MEDI3902 antibodies dramatically increased survival of mice over seven days as compared to the control antibody (R347).

Figure 9:
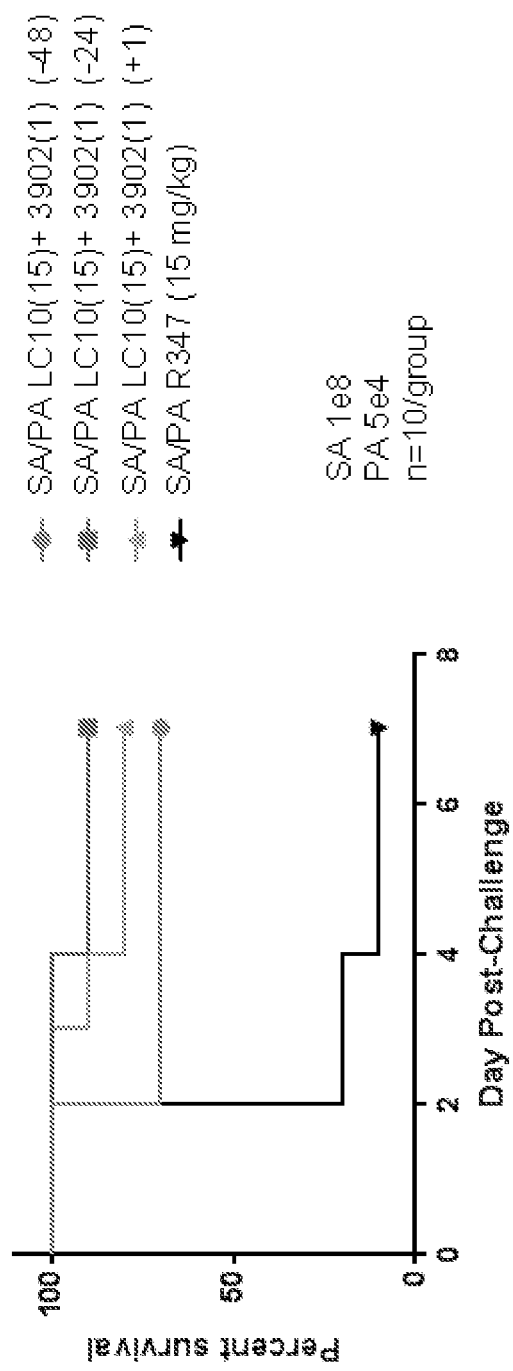
FIG. 9 shows the survival of mice that received a combination of 15 mg/kg anti-*S. aureus* alpha toxin antibody ("LC10") and 1 mg/kg anti-*P. aeruginosa* antibody ("3902") or 15 mg/kg control antibody ("R347") 48 hours before, 24 hours before, or 1 hour after inoculation with *S. aureus* ("SA") and *P. aeruginosa* ("PA").

In order to assess the important of the timing of administration of the protective anti-*S. aureus* and *P. aeruginosa* antibodies, mice were given 15 mg/kg LC10 and 1 mg/kg MEDI3902 or 15 mg/kg R347 at three different times: 48-hours prior to inoculation, 24-hours prior to inoculation, or 1 hour after inoculation. All mice were inoculated with 5e7-1e8 CFU *S. aureus* and 5e4 CFU *P. aeruginosa*. Administration at any of the three times tested was sufficient to increase survival of mice over seven days as compared to administration of the control antibody (FIG. 9).

These data demonstrate that the combination of anti-*S. aureus* and *P. aeruginosa* antibodies prevents infections by mixed *S. aureus* and *P. aeruginosa* colonies.

Figure 10:
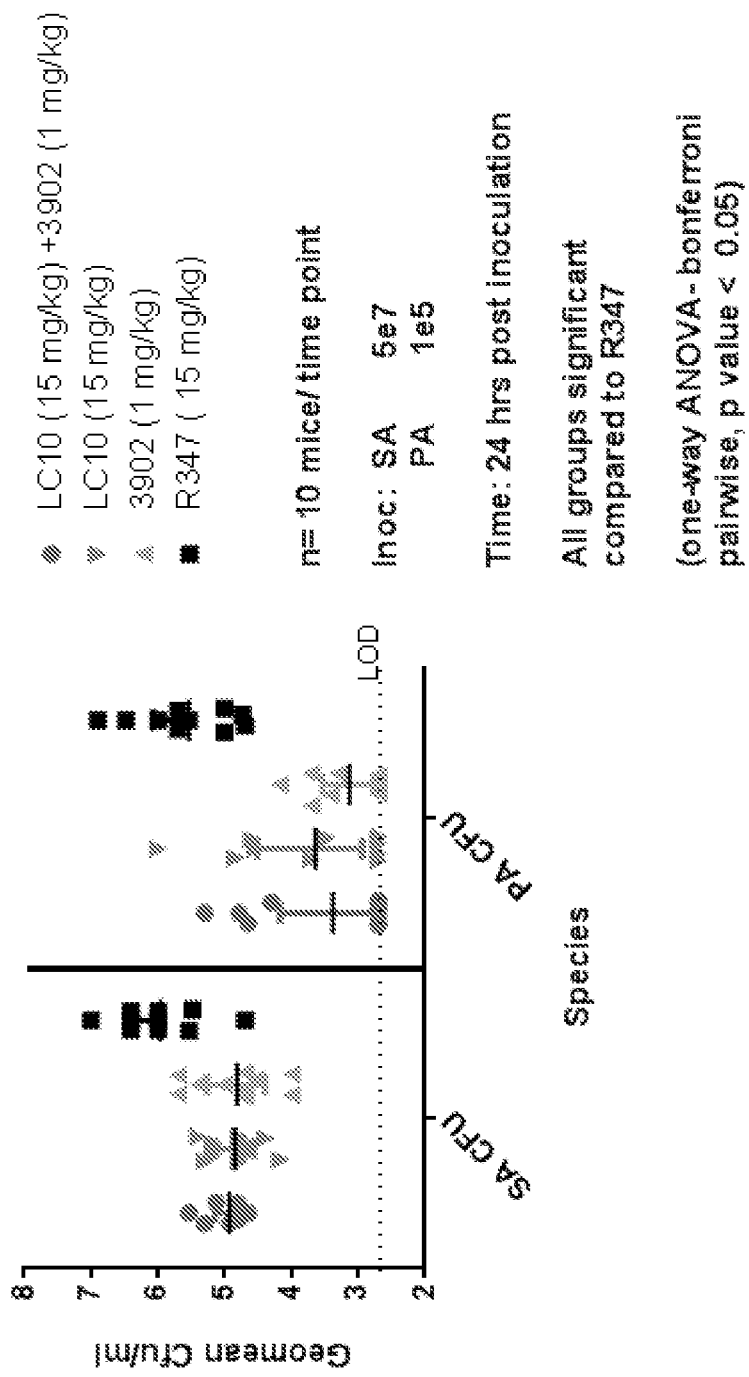
FIG. 10 shows the levels of *S. aureus* ("SA CFU") and *P. aeruginosa* ("PA CFU") in mice receiving either 15 mg/kg anti-*S. aureus* alpha toxin antibody ("LC10"), 1 mg/kg anti-*P. aeruginosa* antibody ("3902"), or 15 mg/kg control antibody ("R347").

Example 4: Anti-Alpha Toxin Antibody is Sufficient to Inhibit the Growth *P. aeruginosa* in a *S. aureus* and *P. aeruginosa* Co-Infection Model In order to examine the effects of individual antibodies on the growth of mixed colonies of *S. aureus* and *P. aeruginosa*, mice were given either (i) a combination of 15 mg/kg LC10 and 1 mg/kg MEDI3902, (ii) 15 mg/kg LC10, (iii) 1 mg/kg MEDI3902, or (iv) 15 mg/kg control antibody (R347). The antibodies were administered 24 hours before the mice were inoculated with 5e7 CFU *S. aureus* and 1e5 CFU *P. aeruginosa*. Lungs were harvested 24 hours after infection, and the homogenates were plated on selective agar to assess *S. aureus* and *P. aeruginosa* growth. Surprisingly, administration of the anti-*S. aureus* alpha toxin antibody decreased both *S. aureus* and *P. aeruginosa* growth, and administration of the anti-*P. aeruginosa* antibody decreased both *S. aureus* and *P. aeruginosa* growth (FIG. 10).

These data demonstrate that anti-*S. aureus* alpha toxin antibodies can inhibit growth of *P. aeruginosa* in a mixed colony containing both *S. aureus* and *P. aeruginosa*. In addition, anti-*P. aeruginosa* antibodies reduce *S. aureus* CFU in an *S. aureus*/*P. aeruginosa* co-infection model.

Example 5: Proliferation and Systemic Dissemination of *P. aeruginosa* Correlates with AT Dependent Loss of Airway Barrier Integrity AT binding to its receptor, ADAM10, on epithelial cell surface results in vascular leakage due to reorganization of junctional proteins and cell lysis (Bubeck Nat Med ADAM10 gp junction). Epithelial necrosis was observed in lung sections from mice infected with *S. aureus* or treated with AT. Additionally, an increase in airway hemoglobin was observed in mice infected with *S. aureus* or AT, indicating the presence of red blood cells. Therefore we hypothesized that AT may promote Gram-negative dissemination by perturbation of the epithelial barrier. In the mixed-infection with either *S. aureus* or purified AT, the spleen contained significantly larger numbers of *P. aeruginosa* in comparison to animals infected with *P. aeruginosa* alone (FIG. 11A). There was no difference in *S. aureus* bacterial burden in the spleens of mice in the mono or co-infected mouse groups (FIG. 11B). Prophylaxis with LC10 significantly decreased the numbers of *P. aeruginosa* recovered from distal organs at 24 and 48 h (FIG. 11C). These data demonstrate that AT promotes systemic dissemination of *P. aeruginosa* during a mixed infection.

Figure 12:
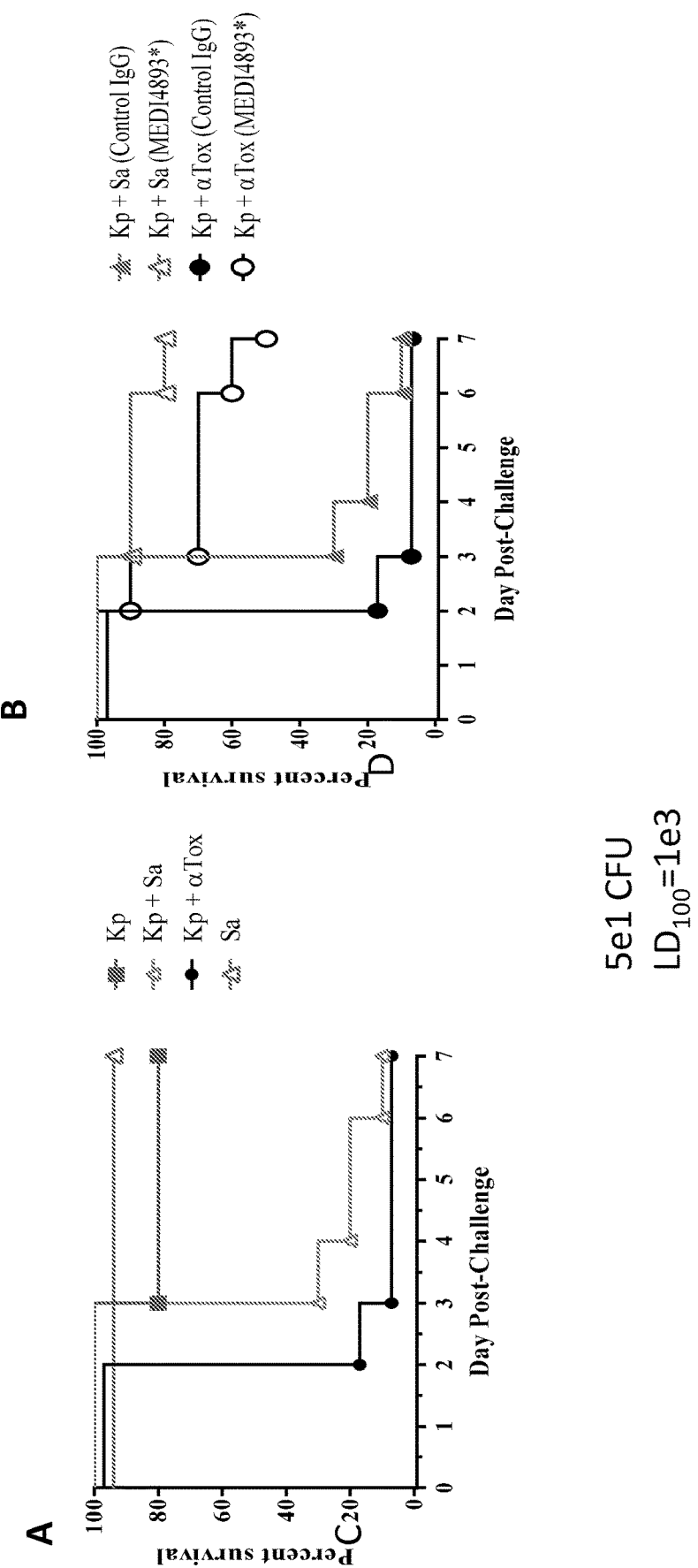
FIG. 12 shows that α-Toxin also potentiates *Klebsiella pneumoniae* and *Acinetobacter baumannii* virulence in lung infection model. A) Groups of mice were infected intranasally with *K. pneumonia* 5e1 (■), *K. pneumoniae* 5e1+*S. aureus* (5e7) (▲), *K. pneumoniae* 5e1+AT (●), *S. aureus* (Δ). Survival was monitored for 7 days B) Animals were injected with LC10 (Δ), or the iso-type IgG (▲) and challenged intranasally 24 h later as described above with *K. pneumoniae*+*S. aureus*, or *K. pneumoniae*+AT LC10 (o), or the iso-type IgG (●). CFU recovery from the lungs (C) and spleens (D) 24 h post-challenge. E) Groups of mice were infected intranasally with *A. baumannii* (8e5) (■), *A. baumannii* 8e5+*S. aureus* (5e7) (▲), *A. baumannii* 8e5+AT (●), *S. aureus* (Δ). Animals were injected with LC10 (Δ), or the iso-type IgG (▲) and challenged intranasally 24 h later with *A. baumannii*+*S. aureus*, or *A. baumannii*+AT LC10 (o), or the iso-type IgG (●). CFU recovery from the lungs (F) and spleens (G) 24 h post-challenge.
Figure 12:
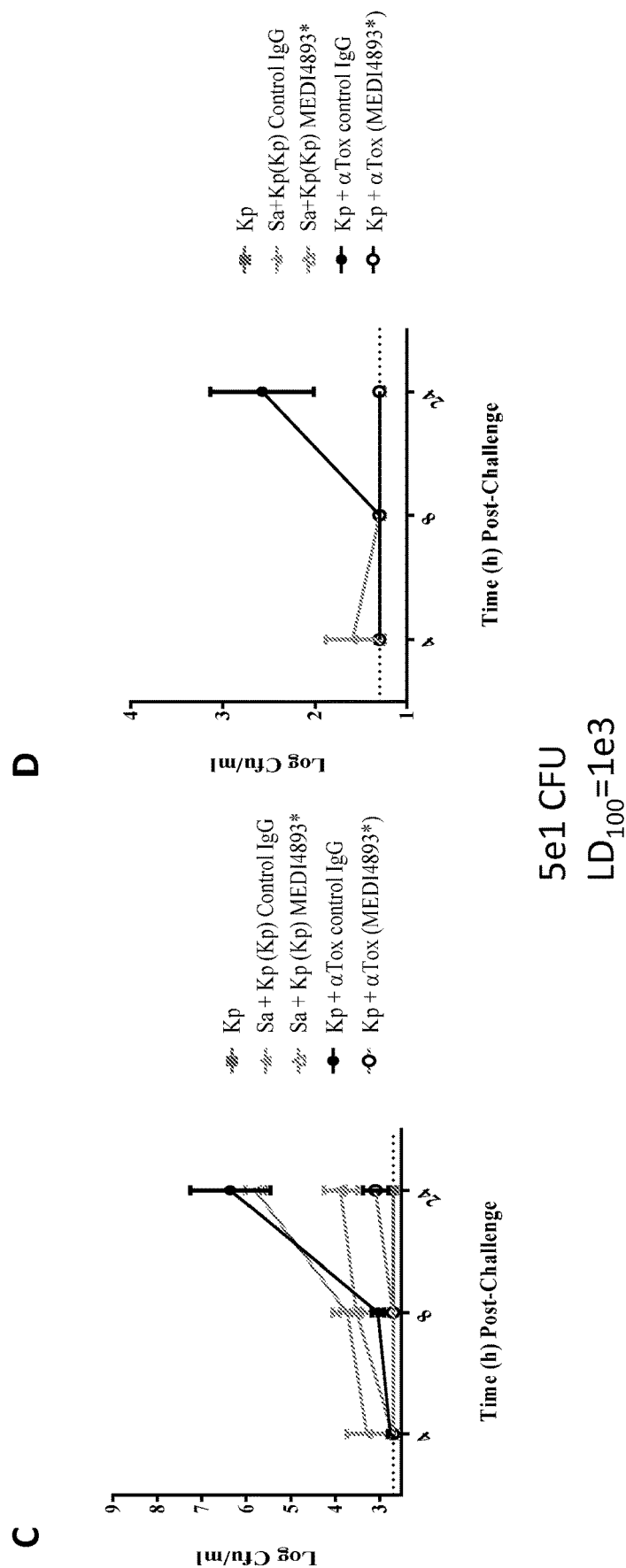
Figure 12:
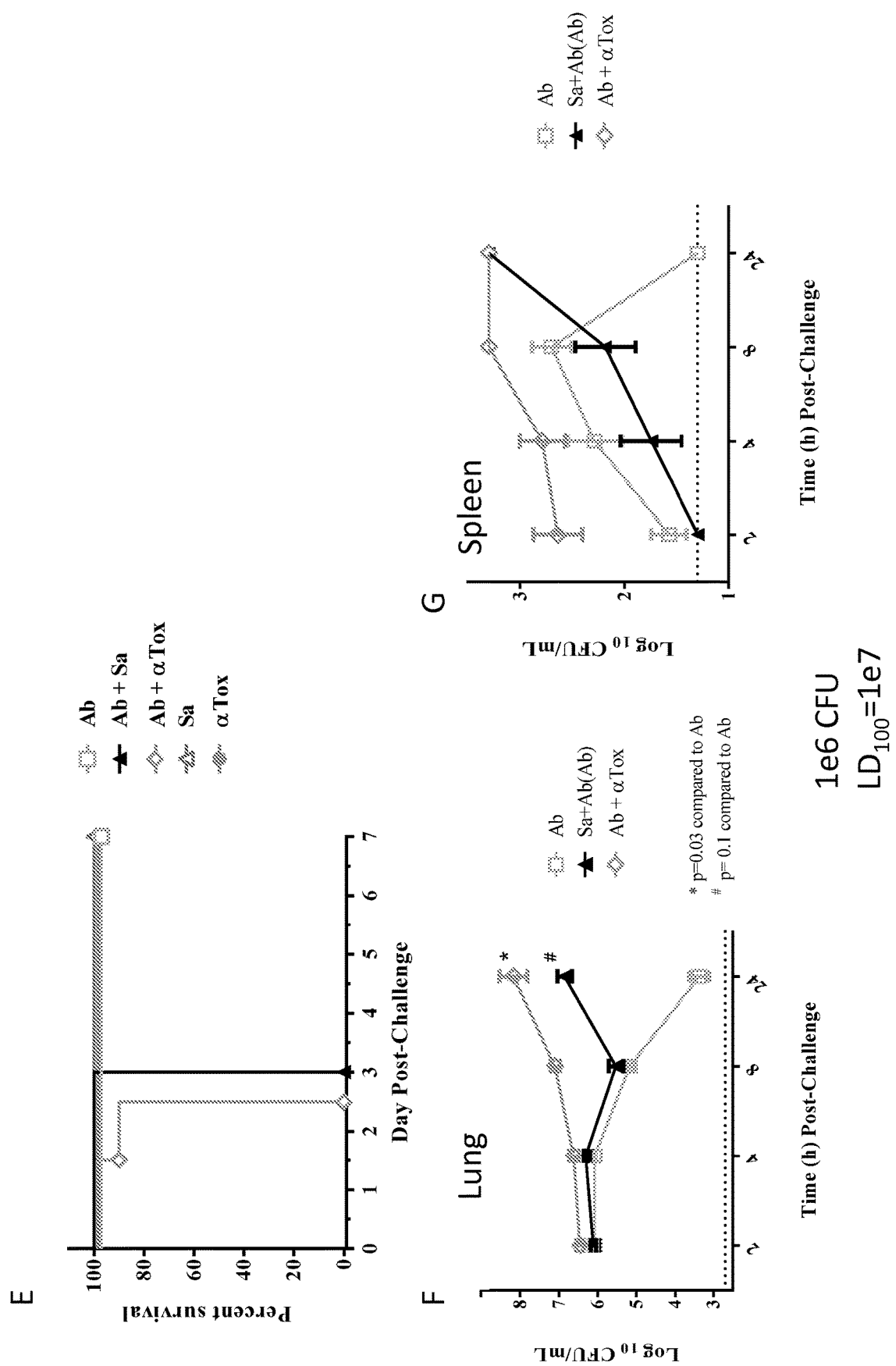

Example 6: *S. aureus* AT Potentiates Infection with Diverse Gram-Negative Bacteria To determine if the effect of AT is specific to *P. aeruginosa* or could be observed during SA co-infection with other Gram-negative organisms, SA co-infections were performed with either *K. pneumoniae* or *A. baumannii*. Sub-lethal IN challenge doses of 5e1 CFU/mouse *K. pneumoniae* or 1e6 CFU/mouse *A. baumannii* (⅟20 and ⅟10 LD100 respectively) with 5e7 CFU/mouse *S. aureus* resulted in 90-100% lethality and increased Gram-negative bacterial burden in the lung and distal tissues compared to Gram-negative mono-infections (FIGS. 12B,C,E,F). Similar to results with Pa, LC10 prophylaxis and co-infection with Δhla prevented lethality and reduced Gram-negative bacterial burden suggesting AT plays a key role in the potentiation of co-infections with these pathogens as well. Consistent with this hypothesis, co-administration of a sub-lethal AT dose along with either Kp or Ab was sufficient to potentiate growth of the Gram-negative pathogen and, to induce a lethal infection. These data show that *S. aureus* AT expression potentiates respiratory infection with a range of Gram-negative opportunistic bacterial pathogens.

Those skilled in the art will recognize, or be able to ascertain using no more than routine experimentation, many equivalents to the specific aspects of the disclosure described herein. Such equivalents are intended to be encompassed by the following claims.

Various publications are cited herein, the disclosures of which are incorporated by reference in their entireties.

Although the foregoing invention has been described in some detail by way of illustration and example for purposes of clarity of understanding, it will be obvious that certain changes and modifications can be practiced within the scope of the appended claims.

What is claimed is:

1. A method of treating a polybacterial infection comprising administering an IgG antibody that specifically binds to *Staphylococcus aureus* (*S. aureus*) alpha toxin and comprises the VH and VL amino acid sequences of SEQ ID NOs:45 and 46, respectively, to a patient with a polybacterial infection comprising *S. aureus* and a gram-negative bacteria selected from one or more of *P. aeruginosa*, *K. pneumonia*, and *A. baumannii;* wherein said polybacterial infection is an ocular infection comprising the *S. aureus* and the *P. aeruginosa*, *K. pneumoniae* or *A. baumannii*, a lung infection comprising the *S. aureus* and the *P. aeruginosa*, *K. pneumoniae* or *A. baumannii*, a burn infection comprising the *S. aureus* and the *P. aeruginosa*, *K. pneumoniae* or *A. baumannii*, a wound infection comprising the *S. aureus* and the *P. aeruginosa*, *K. pneumoniae* or *A. baumannii*, a surgical wound infection comprising the *S. aureus* and the *P. aeruginosa*, *K. pneumoniae* or *A. baumannii*, a skin infection comprising the *S. aureus* and the *P. aeruginosa*, *K. pneumoniae* or *A. baumannii*, a soft tissue infection comprising the *S. aureus* and the *P. aeruginosa*, *K. pneumoniae* or *A. baumannii*, a blood infection comprising the *S. aureus* and the *P. aeruginosa, K. pneumoniae* or *A. baumannii*,
a bone infection comprising the *S. aureus* and the *P. aeruginosa, K. pneumoniae* or *A. baumannii*, or
a combination of two or more of said infections, wherein each of said two or more infections comprises the *S. aureus* and the *P. aeruginosa, K. pneumoniae* or *A. baumannii*.

2. The method of claim 1, wherein the polybacterial infection is a nosocomial polybacterial infection.

3. The method of claim 1, wherein the IgG antibody comprises the YTE substitutions of M252Y, S254T, and T256E, wherein the numbering is according to the EU index.

4. A method of treating a polybacterial infection comprising administering an antibody that specifically binds to *Staphylococcus aureus* (*S. aureus*) alpha toxin and comprises a heavy chain comprising the amino acid sequence of SEQ ID NO:68 and a light chain comprising the amino acid sequence of SEQ ID NO:69 to a patient with a polybacterial infection comprising *S. aureus* and a gram-negative bacteria selected from one or more of *P. aeruginosa, K pneumonia*, and *A. baumannii*;
wherein said polybacterial infection is
an ocular infection comprising the *S. aureus* and the *P. aeruginosa, K. pneumoniae* or *A. baumannii*,
a lung infection comprising the *S. aureus* and the *P. aeruginosa, K. pneumoniae* or *A. baumannii*,
a burn infection comprising the *S. aureus* and the *P. aeruginosa, K. pneumoniae* or *A. baumannii*,
a wound infection comprising the *S. aureus* and the *P. aeruginosa, K. pneumoniae* or *A. baumannii*,
a surgical wound infection comprising the *S. aureus* and the *P. aeruginosa, K. pneumoniae* or *A. baumannii*,
a skin infection comprising the *S. aureus* and the *P. aeruginosa, K. pneumoniae* or *A. baumannii*,
a soft tissue infection comprising the *S. aureus* and the *P. aeruginosa, K. pneumoniae* or *A. baumannii*,
a blood infection comprising the *S. aureus* and the *P. aeruginosa, K. pneumoniae* or *A. baumannii*,
a bone infection comprising the *S. aureus* and the *P. aeruginosa, K. pneumoniae* or *A. baumannii*, or
a combination of two or more of said infections, wherein each of said two or more infections comprises the *S. aureus* and the *P. aeruginosa, K. pneumoniae* or *A. baumannii*.

5. The method of claim 4, wherein the polybacterial infection is a nosocomial polybacterial infection.

6. A method of treating a polybacterial infection comprising administering an IgG antibody that specifically binds to *S. aureus* alpha toxin and comprises the VH and VL amino acid sequences of SEQ ID Nos. 45 and 46, respectively, to a patient with a polybacterial infection comprising *S. aureus* and at least one other gram-negative bacterium selected from one or more of *P. aeruginosa, K. pneumoniae* or *A. baumannii*, wherein the *S. aureus* and the at least one other gram-negative bacterium are in the same location.

7. The method of claim 6, wherein the antibody or antigen-binding fragment thereof is an antibody comprising a heavy chain comprising the amino acid sequence of SEQ ID NO:68 and a light chain comprising the amino acid sequence of SEQ ID NO:69.

8. The method of claim 7, wherein the polybacterial infection is a nosocomial polybacterial infection.

9. The method of claim 6, wherein the polybacterial infection is a nosocomial polybacterial infection.

10. The method of claim 6, wherein the IgG antibody comprises the YTE substitutions of M252Y, S254T, and T256E, wherein the numbering is according to the EU index.

* * * * *

SEQUENCE LISTING

```
<160> NUMBER OF SEQ ID NOS: 101

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ala Ser Gln Ser Ile Ser Ser Trp Leu Ala
1               5                   10
```

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Ala Ser Ser Leu Glu Ser
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Gln Tyr Asn Ser Tyr Trp Thr
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Gln Gly Ile Arg Asn Asp Leu Gly
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Ala Ser Ser Leu Gln Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Gln Asp Tyr Asn Tyr Pro Trp Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 7

Ser Tyr Asp Met His
1               5

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Ile Gly Thr Ala Gly Asp Thr Tyr Tyr Pro Gly Ser Val Lys Gly
1               5                   10                  15

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Asn Tyr Ser Ser Thr Gly Gly Tyr Tyr Gly Met Asp Val
1               5                   10

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Tyr Asp Met His
1               5

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Ile Gly Thr Asp Gly Asp Thr Tyr Tyr Pro Gly Ser Val Lys Gly
1               5                   10                  15

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Arg Tyr Ser Ser Ser Asn His Tyr Asn Gly Met Asp Val
1               5                   10

<210> SEQ ID NO 13
<211> LENGTH: 5
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 13

Ser Tyr Ala Met Thr
1               5

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Ile Ser Gly Ser Gly Gly Ser Thr Tyr Tyr Ala Asp Ser Val Lys
1               5                   10                  15

Gly

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Gly Arg Gln Val Glu Asp Tyr Tyr Tyr Tyr Gly Met Asp Val
1               5                   10                  15

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Arg Tyr Ser Pro Thr Gly His Tyr Met Gly Met Asp Val
1               5                   10

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Val Ile Asp Thr Ala Gly Asp Thr Tyr Tyr Pro Gly Ser Val Lys Gly
1               5                   10                  15

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18
```

Asp Arg Tyr Ser Gly Asn Phe His Tyr Asn Gly Met Asp Val
1               5                   10

<210> SEQ ID NO 19
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Trp Thr
                85                  90                  95

Phe Gly Gln Gly Thr Lys Val Glu Ile Lys
            100                 105

<210> SEQ ID NO 20
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
50                  55                  60

Gly Arg Phe Thr Ile Ser Arg Glu Asn Ala Lys Asn Ser Leu Tyr Leu
65                  70                  75                  80

Gln Leu Asn Ser Leu Arg Ala Gly Asp Thr Ala Val Tyr Phe Cys Ala
                85                  90                  95

Arg Asp Asn Tyr Ser Ser Thr Gly Gly Tyr Tyr Gly Met Asp Val Trp
            100                 105                 110

Gly Gln Gly Thr Thr Val Thr Val Ser Ser
        115                 120

<210> SEQ ID NO 21
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Trp Thr
                85                  90                  95

Phe Gly Gln Gly Thr Lys Val Glu Ile Lys
            100                 105

<210> SEQ ID NO 22
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Asp Met His Trp Val Arg Gln Ala Thr Gly Lys Gly Leu Glu Trp Val
        35                  40                  45

Ser Val Ile Gly Thr Asp Gly Asp Thr Tyr Tyr Pro Gly Ser Val Lys
50                  55                  60

Gly Arg Phe Ile Ile Ser Arg Glu Asn Ala Lys Asn Ser Leu Tyr Leu
65                  70                  75                  80

Glu Met Asn Ser Leu Arg Ala Gly Asp Thr Ala Val Tyr Tyr Cys Ala
                85                  90                  95

Arg Asp Arg Tyr Ser Ser Asn His Tyr Asn Gly Met Asp Val Trp
            100                 105                 110

Gly Gln Gly Thr Thr Val Thr Val Ser Ser
        115                 120

<210> SEQ ID NO 23
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Val Leu Ile
        35                  40                  45

Tyr Lys Ala Ser Ser Leu Glu Ser Gly Val Pro Ser Arg Phe Ser Gly

```
                    50                  55                  60
Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Trp Thr
                 85                  90                  95

Phe Gly Gln Gly Thr Lys Val Glu Ile Lys
            100                 105

<210> SEQ ID NO 24
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Asp Met His Trp Val Arg Gln Ala Thr Gly Lys Gly Leu Glu Trp Val
        35                  40                  45

Ser Val Ile Gly Thr Asp Gly Asp Thr Tyr Tyr Pro Gly Ser Val Lys
    50                  55                  60

Gly Arg Phe Ile Ile Ser Arg Glu Asn Ala Lys Asn Ser Leu Tyr Leu
 65                  70                  75                  80

Glu Met Asn Ser Leu Arg Ala Gly Asp Thr Ala Val Tyr Tyr Cys Ala
                 85                  90                  95

Arg Asp Arg Tyr Ser Ser Ser Asn His Tyr Asn Gly Met Asp Val Trp
            100                 105                 110

Gly Gln Gly Thr Thr Val Thr Val Ser Ser
        115                 120

<210> SEQ ID NO 25
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Tyr Asn Tyr Pro Trp
                 85                  90                  95

Thr Phe Gly Gln Gly Thr Lys Val Glu Ile Lys
            100                 105
```

<210> SEQ ID NO 26
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Val Ile Ser Gly Ser Gly Gly Ser Thr Tyr Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Arg Gln Val Glu Asp Tyr Tyr Tyr Tyr Gly Met
            100                 105                 110

Asp Val Trp Gly Gln Gly Thr Thr Val Thr Val Ser Ser
        115                 120                 125

<210> SEQ ID NO 27
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Trp Thr
                85                  90                  95

Phe Gly Gln Gly Thr Lys Val Glu Ile Lys
            100                 105

<210> SEQ ID NO 28
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Glu Ser Gly Gly Gly Leu Val Gln Pro Gly Gly
1               5                   10                  15

```
Ser Leu Arg Leu Ser Cys Thr Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Val Ile Asp Thr Ala Gly Asp Thr Tyr Tyr Pro Gly Ser Val Lys
 50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Val
            85                  90                  95

Arg Asp Arg Tyr Ser Gly Asn Phe His Tyr Asn Gly Met Asp Val Trp
        100                 105                 110

Gly Gln Gly Thr Thr Val Thr Val Ser Ser
        115                 120

<210> SEQ ID NO 29
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
 50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
            85                  90                  95

Arg Asp Arg Tyr Ser Pro Thr Gly His Tyr Met Gly Met Asp Val Trp
        100                 105                 110

Gly Gln Gly Thr Thr Val Thr Val Ser Ser
        115                 120

<210> SEQ ID NO 30
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
 50                  55                  60
```

```
Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asp Thr Tyr Trp Thr
                 85                  90                  95

Phe Gly Gln Gly Thr Lys Val Glu Ile Lys
            100                 105

<210> SEQ ID NO 31
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
 50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                 85                  90                  95

Arg Asp Arg Tyr Ser Arg Thr Gly His Tyr Met Gly Met Asp Val Trp
            100                 105                 110

Gly Gln Gly Thr Thr Val Thr Val Ser Ser
        115                 120

<210> SEQ ID NO 32
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asp Thr Tyr Trp Thr
                 85                  90                  95

Phe Gly Gln Gly Thr Lys Val Glu Ile Lys
            100                 105

<210> SEQ ID NO 33
```

<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Tyr Ser Arg Thr Gly His Tyr Met Gly Met Ser Leu Trp
            100                 105                 110

Gly Gln Gly Thr Thr Val Thr Val Ser Ser
        115                 120

<210> SEQ ID NO 34
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Tyr Trp Thr
                85                  90                  95

Phe Gly Gln Gly Thr Lys Val Glu Ile Lys
            100                 105

<210> SEQ ID NO 35
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Asn Tyr Ser Arg Thr Gly His Tyr Met Gly Met Asp Val Trp
            100                 105                 110

Gly Gln Gly Thr Thr Val Thr Val Ser Ser
        115                 120

<210> SEQ ID NO 36
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Lys Gln Tyr Ala Asp Tyr Trp Thr
                85                  90                  95

Phe Gly Gln Gly Thr Lys Val Glu Ile Lys
            100                 105

<210> SEQ ID NO 37
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                    85                  90                  95

Arg Asp Asn Tyr Ser Arg Thr Gly His Tyr Met Gly Met Asp Val Trp
                100                 105                 110

Gly Gln Gly Thr Thr Val Thr Val Ser Ser
            115                 120

<210> SEQ ID NO 38
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Tyr Trp Thr
                85                  90                  95

Phe Gly Gln Gly Thr Lys Val Glu Ile Lys
            100                 105

<210> SEQ ID NO 39
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Asp Met His Trp Val Arg Gln Ala Thr Gly Lys Gly Leu Glu Trp Val
            35                  40                  45

Ser Gly Ile Gly Thr Ala Gly Asp Thr Tyr Tyr Pro Gly Ser Val Lys
50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Tyr Ser Pro Thr Gly His Tyr Met Gly Met Ser Leu Trp
                100                 105                 110

Gly Gln Gly Thr Thr Val Thr Val Ser Ser
            115                 120

<210> SEQ ID NO 40
<211> LENGTH: 106

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40
```

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Tyr Trp Thr
                85                  90                  95

Phe Gly Gln Gly Thr Lys Val Glu Ile Lys
            100                 105

```
<210> SEQ ID NO 41
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Tyr Ser Arg Thr Gly His Tyr Met Gly Met Asp Val Trp
            100                 105                 110

Gly Gln Gly Thr Thr Val Thr Val Ser Ser
        115                 120

```
<210> SEQ ID NO 42
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42
```

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp

```
                20                  25                  30
Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Lys Gln Tyr Ala Asp Tyr Trp Thr
                85                  90                  95

Phe Gly Gln Gly Thr Lys Val Glu Ile Lys
                100                 105

<210> SEQ ID NO 43
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Asp Met His Trp Val Arg Gln Ala Thr Gly Lys Gly Leu Glu Trp Val
            35                  40                  45

Ser Gly Ile Gly Thr Ala Gly Asp Thr Tyr Tyr Pro Gly Ser Val Lys
 50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                85                  90                  95

Arg Asp Asn Tyr Ser Ser Thr Gly Gly Tyr Tyr Gly Met Asp Val Trp
                100                 105                 110

Gly Gln Gly Thr Thr Val Thr Val Ser Ser
            115                 120

<210> SEQ ID NO 44
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Trp Thr
```

```
                        85                  90                  95

Phe Gly Gln Gly Thr Lys Val Glu Ile Lys
            100                 105

<210> SEQ ID NO 45
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Asp Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Tyr Ser Pro Thr Gly His Tyr Tyr Gly Met Asp Val Trp
            100                 105                 110

Gly Gln Gly Thr Thr Val Thr Val Ser Ser
        115                 120

<210> SEQ ID NO 46
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Lys Gln Tyr Ala Asp Tyr Trp Thr
                85                  90                  95

Phe Gly Gln Gly Thr Lys Val Glu Ile Lys
            100                 105

<210> SEQ ID NO 47
<211> LENGTH: 122
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Asn Tyr Ser Pro Thr Gly Gly Tyr Tyr Gly Met Asp Val Trp
            100                 105                 110

Gly Gln Gly Thr Thr Val Thr Val Ser Ser
        115                 120

<210> SEQ ID NO 48
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Lys Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Glu Ser Tyr Trp Thr
                85                  90                  95

Phe Gly Gln Gly Thr Lys Val Glu Ile Lys
            100                 105

<210> SEQ ID NO 49
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Asp Met His Trp Val Arg Gln Ala Thr Gly Lys Gly Leu Glu Trp Val
        35                  40                  45

```
Ser Gly Ile Gly Thr Arg Gly Asp Thr Tyr Tyr Pro Asp Ser Val Lys
        50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                85                  90                  95

Arg Asp Arg Tyr Ser Pro Thr Gly His Tyr Tyr Gly Met Asp Val Trp
            100                 105                 110

Gly Gln Gly Thr Thr Val Thr Val Ser Ser
            115                 120

<210> SEQ ID NO 50
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser His
                20                  25                  30

Asp Met His Trp Val Arg Gln Ala Thr Gly Lys Gly Leu Glu Trp Val
            35                  40                  45

Ser Gly Ile Gly Thr Arg Gly Asp Thr Tyr Tyr Pro Asp Ser Val Lys
        50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                85                  90                  95

Arg Asp Lys Tyr Ser Pro Thr Gly His Tyr Tyr Gly Met Asp Val Trp
            100                 105                 110

Gly Gln Gly Thr Thr Val Thr Val Ser Ser
            115                 120

<210> SEQ ID NO 51
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Val Lys Gly Val Pro Ser Arg Phe Ser Gly
        50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Glu Ser Tyr Trp Thr
                85                  90                  95
```

Phe Gly Gln Gly Thr Lys Val Glu Ile Lys
            100                 105

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Gln Tyr Asp Thr Tyr Trp Thr
1               5

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asp Arg Tyr Ser Arg Thr Gly His Tyr Met Gly Met Asp Val
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Arg Tyr Ser Arg Thr Gly His Tyr Met Gly Met Ser Leu
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asp Asn Tyr Ser Arg Thr Gly His Tyr Met Gly Met Asp Val
1               5                   10

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Lys Gln Tyr Ala Asp Tyr Trp Thr
1               5

<210> SEQ ID NO 57
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 57

Ser His Asp Met His
1               5

<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Ile Gly Thr Ala Gly Asp Thr Tyr Tyr Pro Asp Ser Val Lys Gly
1               5                   10                  15

<210> SEQ ID NO 59
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asp Arg Tyr Ser Pro Thr Gly His Tyr Tyr Gly Met Asp Val
1               5                   10

<210> SEQ ID NO 60
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asp Asn Tyr Ser Pro Thr Gly Gly Tyr Tyr Gly Met Asp Val
1               5                   10

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Lys Ala Ser Ser Leu Lys Ser
1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Gln Tyr Glu Ser Tyr Trp Thr
1               5
```

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Ile Gly Thr Arg Gly Asp Thr Tyr Tyr Pro Asp Ser Val Lys Gly
1               5                   10                  15

<210> SEQ ID NO 64
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asp Lys Tyr Ser Pro Thr Gly His Tyr Tyr Gly Met Asp Val
1               5                   10

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Lys Ala Ser Ser Leu Val Lys
1               5

<210> SEQ ID NO 66
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asp Arg Tyr Ser Pro Thr Gly His Tyr Met Gly Met Ser Leu
1               5                   10

<210> SEQ ID NO 67
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Asp Ser Val Lys
    50                  55                  60

```
Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                 85                  90                  95

Arg Asp Arg Tyr Ser Pro Thr Gly His Tyr Tyr Gly Met Asp Val Trp
            100                 105                 110

Gly Gln Gly Thr Thr Val Thr Val Ser Ser
        115                 120

<210> SEQ ID NO 68
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser His
             20                  25                  30

Asp Met His Trp Val Arg Gln Ala Thr Gly Lys Gly Leu Glu Trp Val
         35                  40                  45

Ser Gly Ile Gly Thr Ala Gly Asp Thr Tyr Tyr Pro Asp Ser Val Lys
 50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                 85                  90                  95

Arg Asp Arg Tyr Ser Pro Thr Gly His Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Tyr Ile Thr Arg Glu Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300
```

```
Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 69
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Lys Gln Tyr Ala Asp Tyr Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
```

Asn Arg Gly Glu
    210

<210> SEQ ID NO 70
<211> LENGTH: 293
<212> TYPE: PRT
<213> ORGANISM: Staphylococcus aureus

<400> SEQUENCE: 70

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65              70                  75                  80

Pro Ser Ala Phe Lys Val Gln Leu Gln Leu Pro Asp Asn Glu Val Ala
            85                  90                  95

Gln Ile Ser Asp Tyr Tyr Pro Arg Asn Ser Ile Asp Thr Lys Glu Tyr
        100                 105                 110

Met Ser Thr Leu Thr Tyr Gly Phe Asn Gly Asn Val Thr Gly Asp Asp
    115                 120                 125

Thr Gly Lys Ile Gly Gly Leu Ile Gly Ala Asn Val Ser Ile Gly His
130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
            165                 170                 175

Gln Asn Trp Gly Pro Tyr Asp Arg Asp Ser Trp Asn Pro Val Tyr Gly
        180                 185                 190

Asn Gln Leu Phe Met Lys Thr Arg Asn Gly Ser Met Lys Ala Ala Asp
    195                 200                 205

Asn Phe Leu Asp Pro Asn Lys Ala Ser Ser Leu Leu Ser Ser Gly Phe
210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
            245                 250                 255

Gln Leu His Trp Thr Ser Thr Asn Trp Lys Gly Thr Asn Thr Lys Asp
        260                 265                 270

Lys Trp Thr Asp Arg Ser Ser Glu Arg Tyr Lys Ile Asp Trp Glu Lys
    275                 280                 285

Glu Glu Met Thr Asn
    290

<210> SEQ ID NO 71
<211> LENGTH: 119
<212> TYPE: PRT
<213> ORGANISM: Artificial
<220> FEATURE:
<223> OTHER INFORMATION: WapR-004 VH

<400> SEQUENCE: 71

```
Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65              70                  75                  80

His Val Ser Ser Val Thr Ala Ala Asp Thr Ala Val Tyr Phe Cys Ala
                85                  90                  95

Arg Gly Asp Trp Asp Leu Leu His Ala Leu Asp Ile Trp Gly Gln Gly
            100                 105                 110

Thr Leu Val Thr Val Ser Ser
            115
```

```
<210> SEQ ID NO 72
<211> LENGTH: 107
<212> TYPE: PRT
<213> ORGANISM: Artificial
<220> FEATURE:
<223> OTHER INFORMATION: WapR-004 & WarR-004RAD VL

<400> SEQUENCE: 72

Glu Ile Val Leu Thr Gln Ser Pro Ser Ser Leu Ser Thr Ser Val Gly
1               5                   10                  15

Asp Arg Val Thr Ile Thr Cys Arg Ala Ser Gln Ser Ile Arg Ser His
            20                  25                  30

Leu Asn Trp Tyr Gln Gln Lys Pro Gly Lys Ala Pro Lys Leu Leu Ile
        35                  40                  45

Tyr Gly Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Ser Tyr Ser Phe Pro Leu
                85                  90                  95

Thr Phe Gly Gly Gly Thr Lys Leu Glu Ile Lys
            100                 105
```

```
<210> SEQ ID NO 73
<211> LENGTH: 5
<212> TYPE: PRT
<213> ORGANISM: Artificial
<220> FEATURE:
<223> OTHER INFORMATION: WapR-004 & WapR-004RAD VHCDR1

<400> SEQUENCE: 73

Pro Tyr Tyr Trp Thr
1               5
```

```
<210> SEQ ID NO 74
<211> LENGTH: 16
<212> TYPE: PRT
<213> ORGANISM: Artificial
<220> FEATURE:
<223> OTHER INFORMATION: WapR-004 & WapR-004RAD VHCDR2

<400> SEQUENCE: 74
```

```
Tyr Ile His Ser Ser Gly Tyr Thr Asp Tyr Asn Pro Ser Leu Lys Ser
1               5                   10                  15
```

<210> SEQ ID NO 75
<211> LENGTH: 11
<212> TYPE: PRT
<213> ORGANISM: Artificial
<220> FEATURE:
<223> OTHER INFORMATION: WapR-004 VHCDR3

<400> SEQUENCE: 75

```
Gly Asp Trp Asp Leu Leu His Ala Leu Asp Ile
1               5                   10
```

<210> SEQ ID NO 76
<211> LENGTH: 11
<212> TYPE: PRT
<213> ORGANISM: Artificial
<220> FEATURE:
<223> OTHER INFORMATION: WapR-004 & WapR-004RAD VLCDR1

<400> SEQUENCE: 76

```
Arg Ala Ser Gln Ser Ile Arg Ser His Leu Asn
1               5                   10
```

<210> SEQ ID NO 77
<211> LENGTH: 7
<212> TYPE: PRT
<213> ORGANISM: Artificial
<220> FEATURE:
<223> OTHER INFORMATION: WapR-004 & WapR-004RAD VLCDR2

<400> SEQUENCE: 77

```
Gly Ala Ser Asn Leu Gln Ser
1               5
```

<210> SEQ ID NO 78
<211> LENGTH: 6
<212> TYPE: PRT
<213> ORGANISM: Artificial
<220> FEATURE:
<223> OTHER INFORMATION: WapR-004 & WapR-004RAD VLCDR3

<400> SEQUENCE: 78

```
Tyr Ser Phe Pro Leu Thr
1               5
```

<210> SEQ ID NO 79
<211> LENGTH: 119
<212> TYPE: PRT
<213> ORGANISM: Artificial
<220> FEATURE:
<223> OTHER INFORMATION: WapR-004RAD VH

<400> SEQUENCE: 79

```
Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80
```

```
His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser
        115

<210> SEQ ID NO 80
<211> LENGTH: 11
<212> TYPE: PRT
<213> ORGANISM: Artificial
<220> FEATURE:
<223> OTHER INFORMATION: WapR-004RAD VHCDR3

<400> SEQUENCE: 80

Ala Asp Trp Asp Leu Leu His Ala Leu Asp Ile
1               5                   10

<210> SEQ ID NO 81
<211> LENGTH: 124
<212> TYPE: PRT
<213> ORGANISM: Artificial
<220> FEATURE:
<223> OTHER INFORMATION: V2L2 VH

<400> SEQUENCE: 81

Glu Met Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Glu Gly Leu Glu Trp Val
        35                  40                  45

Ser Ala Ile Thr Ile Ser Gly Ile Thr Ala Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Gly Asp Thr Ala Val Tyr Tyr Cys
                85                  90                  95

Ala Lys Glu Glu Phe Leu Pro Gly Thr His Tyr Tyr Tyr Gly Met Asp
            100                 105                 110

Val Trp Gly Gln Gly Thr Thr Val Thr Val Ser Ser
        115                 120

<210> SEQ ID NO 82
<211> LENGTH: 107
<212> TYPE: PRT
<213> ORGANISM: Artificial
<220> FEATURE:
<223> OTHER INFORMATION: V2L2 VL

<400> SEQUENCE: 82

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Val Ile
        35                  40                  45

Tyr Ser Ala Ser Thr Leu Gln Ser Gly Val Pro Ser Arg Phe Ser Gly
    50                  55                  60
```

Ser Gly Ser Gly Thr Asp Phe Thr Leu Ser Ile Ser Ser Leu Gln Pro
65                  70                  75                  80

Asp Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys
            100                 105

<210> SEQ ID NO 83
<211> LENGTH: 5
<212> TYPE: PRT
<213> ORGANISM: Artificial
<220> FEATURE:
<223> OTHER INFORMATION: V2L2 VHCDR1

<400> SEQUENCE: 83

Ser Tyr Ala Met Asn
1               5

<210> SEQ ID NO 84
<211> LENGTH: 17
<212> TYPE: PRT
<213> ORGANISM: Artificial
<220> FEATURE:
<223> OTHER INFORMATION: V2L2 VHCDR2

<400> SEQUENCE: 84

Ala Ile Thr Ile Ser Gly Ile Thr Ala Tyr Tyr Thr Asp Ser Val Lys
1               5                   10                  15

Gly

<210> SEQ ID NO 85
<211> LENGTH: 15
<212> TYPE: PRT
<213> ORGANISM: Artificial
<220> FEATURE:
<223> OTHER INFORMATION: V2L2 VHCDR3

<400> SEQUENCE: 85

Glu Glu Phe Leu Pro Gly Thr His Tyr Tyr Tyr Gly Met Asp Val
1               5                   10                  15

<210> SEQ ID NO 86
<211> LENGTH: 11
<212> TYPE: PRT
<213> ORGANISM: Artificial
<220> FEATURE:
<223> OTHER INFORMATION: V2L2 VLCDR1

<400> SEQUENCE: 86

Arg Ala Ser Gln Gly Ile Arg Asn Asp Leu Gly
1               5                   10

<210> SEQ ID NO 87
<211> LENGTH: 7
<212> TYPE: PRT
<213> ORGANISM: Artificial
<220> FEATURE:
<223> OTHER INFORMATION: V2LC VLCDR2

<400> SEQUENCE: 87

Ser Ala Ser Thr Leu Gln Ser
1               5

<210> SEQ ID NO 88
<211> LENGTH: 9

```
<212> TYPE: PRT
<213> ORGANISM: Artificial
<220> FEATURE:
<223> OTHER INFORMATION: V2L2 VLCDR3

<400> SEQUENCE: 88

Leu Gln Asp Tyr Asn Tyr Pro Trp Thr
1               5

<210> SEQ ID NO 89
<211> LENGTH: 256
<212> TYPE: PRT
<213> ORGANISM: Artificial
<220> FEATURE:
<223> OTHER INFORMATION: W4-RAD scFv sequence in BS3 vector

<400> SEQUENCE: 89

Gly Gly Gly Gly Ser Gly Gly Gly Ser Glu Val Gln Leu Leu Glu
1               5                   10                  15

Ser Gly Pro Gly Leu Val Lys Pro Ser Glu Thr Leu Ser Leu Thr Cys
            20                  25                  30

Asn Val Ala Gly Gly Ser Ile Ser Pro Tyr Tyr Trp Thr Trp Ile Arg
        35                  40                  45

Gln Pro Pro Gly Lys Cys Leu Glu Leu Ile Gly Tyr Ile His Ser Ser
    50                  55                  60

Gly Tyr Thr Asp Tyr Asn Pro Ser Leu Lys Ser Arg Val Thr Ile Ser
65                  70                  75                  80

Gly Asp Thr Ser Lys Lys Gln Phe Ser Leu His Val Ser Ser Val Thr
                85                  90                  95

Ala Ala Asp Thr Ala Val Tyr Phe Cys Ala Arg Ala Asp Trp Asp Leu
            100                 105                 110

Leu His Ala Leu Asp Ile Trp Gly Gln Gly Thr Leu Val Thr Val Ser
        115                 120                 125

Ser Gly Gly Gly Ser Gly Gly Gly Gly Ser Gly Gly Gly Gly Ser
    130                 135                 140

Gly Gly Gly Gly Ser Glu Ile Val Leu Thr Gln Ser Pro Ser Ser Leu
145                 150                 155                 160

Ser Thr Ser Val Gly Asp Arg Val Thr Ile Thr Cys Arg Ala Ser Gln
                165                 170                 175

Ser Ile Arg Ser His Leu Asn Trp Tyr Gln Gln Lys Pro Gly Lys Ala
            180                 185                 190

Pro Lys Leu Leu Ile Tyr Gly Ala Ser Asn Leu Gln Ser Gly Val Pro
        195                 200                 205

Ser Arg Phe Ser Gly Ser Gly Ser Gly Thr Asp Phe Thr Leu Thr Ile
    210                 215                 220

Ser Ser Leu Gln Pro Glu Asp Phe Ala Thr Tyr Tyr Cys Gln Gln Ser
225                 230                 235                 240

Tyr Ser Phe Pro Leu Thr Phe Gly Cys Gly Thr Lys Leu Glu Ile Lys
                245                 250                 255

<210> SEQ ID NO 90
<211> LENGTH: 380
<212> TYPE: PRT
<213> ORGANISM: Artificial
<220> FEATURE:
<223> OTHER INFORMATION: W4-RAD scFv-V2L2 VH sequences in Bs2 vector

<400> SEQUENCE: 90

Glu Val Gln Leu Leu Glu Ser Gly Pro Gly Leu Val Lys Pro Ser Glu
```

```
              1               5                  10                 15
            Thr Leu Ser Leu Thr Cys Asn Val Ala Gly Gly Ser Ile Ser Pro Tyr
                        20                  25                  30

Tyr Trp Thr Trp Ile Arg Gln Pro Pro Gly Lys Cys Leu Glu Leu Ile
                        35                  40                  45

Gly Tyr Ile His Ser Ser Gly Tyr Thr Asp Tyr Asn Pro Ser Leu Lys
                        50                  55                  60

Ser Arg Val Thr Ile Ser Gly Asp Thr Ser Lys Lys Gln Phe Ser Leu
             65                  70                  75                  80

His Val Ser Ser Val Thr Ala Ala Asp Thr Ala Val Tyr Phe Cys Ala
                        85                  90                  95

Arg Ala Asp Trp Asp Leu Leu His Ala Leu Asp Ile Trp Gly Gln Gly
                       100                 105                 110

Thr Leu Val Thr Val Ser Gly Gly Gly Gly Ser Gly Gly Gly
                       115                 120                 125

Ser Gly Gly Gly Gly Ser Gly Gly Gly Gly Ser Glu Ile Val Leu Thr
                       130                 135                 140

Gln Ser Pro Ser Ser Leu Ser Thr Ser Val Gly Asp Arg Val Thr Ile
            145                 150                 155                 160

Thr Cys Arg Ala Ser Gln Ser Ile Arg Ser His Leu Asn Trp Tyr Gln
                       165                 170                 175

Gln Lys Pro Gly Lys Ala Pro Lys Leu Leu Ile Tyr Gly Ala Ser Asn
                       180                 185                 190

Leu Gln Ser Gly Val Pro Ser Arg Phe Ser Gly Ser Gly Ser Gly Thr
                       195                 200                 205

Asp Phe Thr Leu Thr Ile Ser Ser Leu Gln Pro Glu Asp Phe Ala Thr
                       210                 215                 220

Tyr Tyr Cys Gln Gln Ser Tyr Ser Phe Pro Leu Thr Phe Gly Cys Gly
            225                 230                 235                 240

Thr Lys Leu Glu Ile Lys Gly Gly Gly Ser Gly Gly Gly Gly Ser
                       245                 250                 255

Glu Met Gln Leu Leu Glu Ser Gly Gly Leu Val Gln Pro Gly Gly
                       260                 265                 270

Ser Leu Arg Leu Ser Cys Ala Ala Ser Gly Phe Thr Phe Ser Ser Tyr
                       275                 280                 285

Ala Met Asn Trp Val Arg Gln Ala Pro Gly Glu Gly Leu Glu Trp Val
                       290                 295                 300

Ser Ala Ile Thr Ile Ser Gly Ile Thr Ala Tyr Tyr Thr Asp Ser Val
            305                 310                 315                 320

Lys Gly Arg Phe Thr Ile Ser Arg Asp Asn Ser Lys Asn Thr Leu Tyr
                       325                 330                 335

Leu Gln Met Asn Ser Leu Arg Ala Gly Asp Thr Ala Val Tyr Tyr Cys
                       340                 345                 350

Ala Lys Glu Glu Phe Leu Pro Gly Thr His Tyr Tyr Tyr Gly Met Asp
                       355                 360                 365

Val Trp Gly Gln Gly Thr Thr Val Thr Val Ser Ser
                       370                 375                 380

<210> SEQ ID NO 91
<211> LENGTH: 292
<212> TYPE: PRT
<213> ORGANISM: Artificial
<220> FEATURE:
<223> OTHER INFORMATION: W4-RAD scFv in Bs4 vector
```

<400> SEQUENCE: 91

Lys Val Asp Lys Arg Val Glu Pro Lys Ser Cys Gly Gly Gly Ser
1               5                   10                  15

Gly Gly Gly Gly Ser Glu Val Gln Leu Leu Glu Ser Gly Pro Gly Leu
            20                  25                  30

Val Lys Pro Ser Glu Thr Leu Ser Leu Thr Cys Asn Val Ala Gly Gly
        35                  40                  45

Ser Ile Ser Pro Tyr Tyr Trp Thr Trp Ile Arg Gln Pro Pro Gly Lys
    50                  55                  60

Cys Leu Glu Leu Ile Gly Tyr Ile His Ser Ser Gly Tyr Thr Asp Tyr
65                  70                  75                  80

Asn Pro Ser Leu Lys Ser Arg Val Thr Ile Ser Gly Asp Thr Ser Lys
                85                  90                  95

Lys Gln Phe Ser Leu His Val Ser Val Thr Ala Ala Asp Thr Ala
            100                 105                 110

Val Tyr Phe Cys Ala Arg Ala Asp Trp Asp Leu Leu His Ala Leu Asp
        115                 120                 125

Ile Trp Gly Gln Gly Thr Leu Val Thr Val Ser Ser Gly Gly Gly Gly
    130                 135                 140

Ser Gly Gly Gly Gly Ser Gly Gly Gly Gly Ser Gly Gly Gly Gly Ser
145                 150                 155                 160

Glu Ile Val Leu Thr Gln Ser Pro Ser Ser Leu Ser Thr Ser Val Gly
                165                 170                 175

Asp Arg Val Thr Ile Thr Cys Arg Ala Ser Gln Ser Ile Arg Ser His
            180                 185                 190

Leu Asn Trp Tyr Gln Gln Lys Pro Gly Lys Ala Pro Lys Leu Leu Ile
        195                 200                 205

Tyr Gly Ala Ser Asn Leu Gln Ser Gly Val Pro Ser Arg Phe Ser Gly
    210                 215                 220

Ser Gly Ser Gly Thr Asp Phe Thr Leu Thr Ile Ser Ser Leu Gln Pro
225                 230                 235                 240

Glu Asp Phe Ala Thr Tyr Tyr Cys Gln Gln Ser Tyr Ser Phe Pro Leu
                245                 250                 255

Thr Phe Gly Cys Gly Thr Lys Leu Glu Ile Lys Gly Gly Gly Gly Ser
            260                 265                 270

Gly Gly Gly Gly Ser Asp Lys Thr His Thr Cys Pro Pro Cys Pro Ala
        275                 280                 285

Pro Glu Leu Leu
    290

<210> SEQ ID NO 92
<211> LENGTH: 214
<212> TYPE: PRT
<213> ORGANISM: Artificial
<220> FEATURE:
<223> OTHER INFORMATION: Bs4-V2L2-C2 light

<400> SEQUENCE: 92

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Val Ile
        35                  40                  45

Tyr Ser Ala Ser Thr Leu Gln Ser Gly Val Pro Ser Arg Phe Ser Gly

```
             50                  55                  60
Ser Gly Ser Gly Thr Asp Phe Thr Leu Ser Ile Ser Ser Leu Gln Pro
 65                  70                  75                  80

Asp Asp Phe Ala Thr Tyr Tyr Cys Leu Gln Asp Tyr Asn Tyr Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 93
<211> LENGTH: 720
<212> TYPE: PRT
<213> ORGANISM: Artificial
<220> FEATURE:
<223> OTHER INFORMATION: Bs4-V2L2-C2 heavy

<400> SEQUENCE: 93

Glu Met Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Asn Trp Val Arg Gln Ala Pro Gly Glu Gly Leu Glu Trp Val
         35                  40                  45

Ser Ala Ile Thr Ile Ser Gly Ile Thr Ala Tyr Tyr Thr Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Gly Asp Thr Ala Val Tyr Tyr Cys
                 85                  90                  95

Ala Lys Glu Glu Phe Leu Pro Gly Thr His Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
```

```
            195                 200                 205
Val Asn His Lys Pro Ser Asn Thr Lys Val Asp Lys Arg Val Glu Pro
210                 215                 220

Lys Ser Cys Gly Gly Gly Ser Gly Gly Gly Ser Glu Val Gln
225                 230                 235                 240

Leu Leu Glu Ser Gly Pro Gly Leu Val Lys Pro Ser Glu Thr Leu Ser
                    245                 250                 255

Leu Thr Cys Asn Val Ala Gly Gly Ser Ile Ser Pro Tyr Tyr Trp Thr
                260                 265                 270

Trp Ile Arg Gln Pro Pro Gly Lys Cys Leu Glu Leu Ile Gly Tyr Ile
            275                 280                 285

His Ser Ser Gly Tyr Thr Asp Tyr Asn Pro Ser Leu Lys Ser Arg Val
290                 295                 300

Thr Ile Ser Gly Asp Thr Ser Lys Lys Gln Phe Ser Leu His Val Ser
305                 310                 315                 320

Ser Val Thr Ala Ala Asp Thr Ala Val Tyr Phe Cys Ala Arg Ala Asp
                325                 330                 335

Trp Asp Leu Leu His Ala Leu Asp Ile Trp Gly Gln Gly Thr Leu Val
                340                 345                 350

Thr Val Ser Ser Gly Gly Gly Ser Gly Gly Gly Ser Gly Gly
            355                 360                 365

Gly Gly Ser Gly Gly Gly Ser Glu Ile Val Leu Thr Gln Ser Pro
370                 375                 380

Ser Ser Leu Ser Thr Ser Val Gly Asp Arg Val Thr Ile Thr Cys Arg
385                 390                 395                 400

Ala Ser Gln Ser Ile Arg Ser His Leu Asn Trp Tyr Gln Gln Lys Pro
                405                 410                 415

Gly Lys Ala Pro Lys Leu Leu Ile Tyr Gly Ala Ser Asn Leu Gln Ser
                420                 425                 430

Gly Val Pro Ser Arg Phe Ser Gly Ser Gly Ser Gly Thr Asp Phe Thr
                435                 440                 445

Leu Thr Ile Ser Ser Leu Gln Pro Glu Asp Phe Ala Thr Tyr Tyr Cys
                450                 455                 460

Gln Gln Ser Tyr Ser Phe Pro Leu Thr Phe Gly Cys Gly Thr Lys Leu
465                 470                 475                 480

Glu Ile Lys Gly Gly Gly Gly Ser Gly Gly Gly Gly Ser Asp Lys Thr
                485                 490                 495

His Thr Cys Pro Pro Cys Pro Ala Pro Glu Leu Leu Gly Gly Pro Ser
                500                 505                 510

Val Phe Leu Phe Pro Pro Lys Pro Lys Asp Thr Leu Met Ile Ser Arg
                515                 520                 525

Thr Pro Glu Val Thr Cys Val Val Asp Val Ser His Glu Asp Pro
                530                 535                 540

Glu Val Lys Phe Asn Trp Tyr Val Asp Gly Val Glu Val His Asn Ala
545                 550                 555                 560

Lys Thr Lys Pro Arg Glu Glu Gln Tyr Asn Ser Thr Tyr Arg Val Val
                565                 570                 575

Ser Val Leu Thr Val Leu His Gln Asp Trp Leu Asn Gly Lys Glu Tyr
                580                 585                 590

Lys Cys Lys Val Ser Asn Lys Ala Leu Pro Ala Pro Ile Glu Lys Thr
            595                 600                 605

Ile Ser Lys Ala Lys Gly Gln Pro Arg Glu Pro Gln Val Tyr Thr Leu
610                 615                 620
```

-continued

Pro Pro Ser Arg Glu Glu Met Thr Lys Asn Gln Val Ser Leu Thr Cys
625                 630                 635                 640

Leu Val Lys Gly Phe Tyr Pro Ser Asp Ile Ala Val Glu Trp Glu Ser
            645                 650                 655

Asn Gly Gln Pro Glu Asn Asn Tyr Lys Thr Thr Pro Pro Val Leu Asp
        660                 665                 670

Ser Asp Gly Ser Phe Phe Leu Tyr Ser Lys Leu Thr Val Asp Lys Ser
        675                 680                 685

Arg Trp Gln Gln Gly Asn Val Phe Ser Cys Ser Val Met His Glu Ala
    690                 695                 700

Leu His Asn His Tyr Thr Gln Lys Ser Leu Ser Leu Ser Pro Gly Lys
705                 710                 715                 720

<210> SEQ ID NO 94
<211> LENGTH: 11
<212> TYPE: PRT
<213> ORGANISM: Artificial
<220> FEATURE:
<223> OTHER INFORMATION: Psl0096-Germline VHCDR3

<400> SEQUENCE: 94

Ala Asp Trp Asp Arg Leu Arg Ala Leu Asp Ile
1               5                   10

<210> SEQ ID NO 95
<211> LENGTH: 9
<212> TYPE: PRT
<213> ORGANISM: Artificial
<220> FEATURE:
<223> OTHER INFORMATION: Psl0096-Germline VLCDR3

<400> SEQUENCE: 95

Gln Gln Ser Thr Gly Ala Trp Asn Trp
1               5

<210> SEQ ID NO 96
<211> LENGTH: 119
<212> TYPE: PRT
<213> ORGANISM: Artificial
<220> FEATURE:
<223> OTHER INFORMATION: Psl0096-Germline VH
<220> FEATURE:
<221> NAME/KEY: misc_feature
<222> LOCATION: (44)..(44)
<223> OTHER INFORMATION: Xaa is Gly or Cys

<400> SEQUENCE: 96

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Pro Tyr
            20                  25                  30

Tyr Trp Thr Trp Ile Arg Gln Pro Pro Gly Lys Xaa Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

Lys Leu Ser Ser Val Thr Ala Ala Asp Thr Ala Val Tyr Tyr Cys Ala
                85                  90                  95

Arg Ala Asp Trp Asp Arg Leu Arg Ala Leu Asp Ile Trp Gly Gln Gly
            100                 105                 110

```
Thr Met Val Thr Val Ser Ser
        115

<210> SEQ ID NO 97
<211> LENGTH: 107
<212> TYPE: PRT
<213> ORGANISM: Artificial
<220> FEATURE:
<223> OTHER INFORMATION: Psl0096-Germline VL
<220> FEATURE:
<221> NAME/KEY: misc_feature
<222> LOCATION: (100)..(100)
<223> OTHER INFORMATION: Xaa can be Gly or Cys

<400> SEQUENCE: 97

Asp Ile Gln Leu Thr Gln Ser Pro Ser Leu Ser Ala Ser Val Gly
1               5                   10                  15

Asp Arg Val Thr Ile Thr Cys Arg Ala Ser Gln Ser Ile Arg Ser His
                20                  25                  30

Leu Asn Trp Tyr Gln Gln Lys Pro Gly Lys Ala Pro Lys Leu Leu Ile
            35                  40                  45

Tyr Gly Ala Ser Asn Leu Gln Ser Gly Val Pro Ser Arg Phe Ser Gly
50                      55                      60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Thr Gly Ala Trp Asn
                85                  90                  95

Trp Phe Gly Xaa Gly Thr Lys Val Glu Ile Lys
            100                 105

<210> SEQ ID NO 98
<211> LENGTH: 124
<212> TYPE: PRT
<213> ORGANISM: Artificial
<220> FEATURE:
<223> OTHER INFORMATION: V2L2-MD VH

<400> SEQUENCE: 98

Glu Met Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Asn Trp Val Arg Gln Ala Pro Gly Glu Gly Leu Glu Trp Val
            35                  40                  45

Ser Ala Ile Thr Ile Ser Gly Ile Thr Ala Tyr Tyr Thr Asp Ser Val
50                  55                      60

Lys Gly Arg Phe Thr Ile Ser Arg Asp Asn Ser Lys Asn Thr Leu Tyr
65                  70                  75                  80

Leu Gln Met Asn Ser Leu Arg Ala Gly Asp Thr Ala Val Tyr Tyr Cys
                85                  90                  95

Ala Lys Glu Glu Phe Leu Pro Gly Thr His Tyr Tyr Gly Met Asp
            100                 105                 110

Val Trp Gly Gln Gly Thr Thr Val Thr Val Ser Ser
        115                 120

<210> SEQ ID NO 99
<211> LENGTH: 107
<212> TYPE: PRT
<213> ORGANISM: Artificial
<220> FEATURE:
```

<223> OTHER INFORMATION: V2L2-MD VL

<400> SEQUENCE: 99

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Val Ile
        35                  40                  45

Tyr Ser Ala Ser Thr Leu Gln Ser Gly Val Pro Ser Arg Phe Ser Gly
50                  55                  60

Ser Gly Ser Gly Thr Asp Phe Thr Leu Ser Ile Ser Ser Leu Gln Pro
65                  70                  75                  80

Asp Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys
            100                 105

<210> SEQ ID NO 100
<211> LENGTH: 214
<212> TYPE: PRT
<213> ORGANISM: Artificial
<220> FEATURE:
<223> OTHER INFORMATION: Bs4-GLO LC

<400> SEQUENCE: 100

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ser Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 101

<211> LENGTH: 720
<212> TYPE: PRT
<213> ORGANISM: Artificial
<220> FEATURE:
<223> OTHER INFORMATION: Bs4-GLO HC

<400> SEQUENCE: 101

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Thr Met Ser Gly Ile Thr Ala Tyr Tyr Thr Asp Asp Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Glu Phe Leu Pro Gly Thr His Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Gly Gly Gly Gly Ser Gly Gly Gly Ser Gln Val Gln
225                 230                 235                 240

Leu Gln Glu Ser Gly Pro Gly Leu Val Lys Pro Ser Glu Thr Leu Ser
                245                 250                 255

Leu Thr Cys Thr Val Ser Gly Gly Ser Ile Ser Pro Tyr Tyr Trp Thr
            260                 265                 270

Trp Ile Arg Gln Pro Pro Gly Lys Cys Leu Glu Leu Ile Gly Tyr Ile
        275                 280                 285

His Ser Ser Gly Tyr Thr Asp Tyr Asn Pro Ser Leu Lys Ser Arg Val
    290                 295                 300

Thr Ile Ser Gly Asp Thr Ser Lys Lys Gln Phe Ser Leu Lys Leu Ser
305                 310                 315                 320

Ser Val Thr Ala Ala Asp Thr Ala Val Tyr Tyr Cys Ala Arg Ala Asp
                325                 330                 335

Trp Asp Arg Leu Arg Ala Leu Asp Ile Trp Gly Gln Gly Thr Met Val
            340                 345                 350

Thr Val Ser Ser Gly Gly Gly Ser Gly Gly Gly Gly Ser Gly Gly
        355                 360                 365

Gly Gly Ser Gly Gly Gly Gly Ser Asp Ile Gln Leu Thr Gln Ser Pro
    370                 375                 380

-continued

```
Ser Ser Leu Ser Ala Ser Val Gly Asp Arg Val Thr Ile Thr Cys Arg
385                 390                 395                 400

Ala Ser Gln Ser Ile Arg Ser His Leu Asn Trp Tyr Gln Gln Lys Pro
                405                 410                 415

Gly Lys Ala Pro Lys Leu Leu Ile Tyr Gly Ala Ser Asn Leu Gln Ser
            420                 425                 430

Gly Val Pro Ser Arg Phe Ser Gly Ser Gly Ser Gly Thr Asp Phe Thr
        435                 440                 445

Leu Thr Ile Ser Ser Leu Gln Pro Glu Asp Phe Ala Thr Tyr Tyr Cys
    450                 455                 460

Gln Gln Ser Thr Gly Ala Trp Asn Trp Phe Gly Cys Gly Thr Lys Val
465                 470                 475                 480

Glu Ile Lys Gly Gly Gly Gly Ser Gly Gly Gly Gly Ser Asp Lys Thr
                485                 490                 495

His Thr Cys Pro Pro Cys Pro Ala Pro Glu Leu Leu Gly Gly Pro Ser
            500                 505                 510

Val Phe Leu Phe Pro Pro Lys Pro Lys Asp Thr Leu Met Ile Ser Arg
        515                 520                 525

Thr Pro Glu Val Thr Cys Val Val Val Asp Val Ser His Glu Asp Pro
    530                 535                 540

Glu Val Lys Phe Asn Trp Tyr Val Asp Gly Val Glu Val His Asn Ala
545                 550                 555                 560

Lys Thr Lys Pro Arg Glu Glu Gln Tyr Asn Ser Thr Tyr Arg Val Val
                565                 570                 575

Ser Val Leu Thr Val Leu His Gln Asp Trp Leu Asn Gly Lys Glu Tyr
            580                 585                 590

Lys Cys Lys Val Ser Asn Lys Ala Leu Pro Ala Pro Ile Glu Lys Thr
        595                 600                 605

Ile Ser Lys Ala Lys Gly Gln Pro Arg Glu Pro Gln Val Tyr Thr Leu
    610                 615                 620

Pro Pro Ser Arg Glu Glu Met Thr Lys Asn Gln Val Ser Leu Thr Cys
625                 630                 635                 640

Leu Val Lys Gly Phe Tyr Pro Ser Asp Ile Ala Val Glu Trp Glu Ser
                645                 650                 655

Asn Gly Gln Pro Glu Asn Asn Tyr Lys Thr Thr Pro Pro Val Leu Asp
            660                 665                 670

Ser Asp Gly Ser Phe Phe Leu Tyr Ser Lys Leu Thr Val Asp Lys Ser
        675                 680                 685

Arg Trp Gln Gln Gly Asn Val Phe Ser Cys Ser Val Met His Glu Ala
    690                 695                 700

Leu His Asn His Tyr Thr Gln Lys Ser Leu Ser Leu Ser Pro Gly Lys
705                 710                 715                 720
```